(12) United States Patent
Chen et al.

(10) Patent No.: US 7,608,070 B2
(45) Date of Patent: Oct. 27, 2009

(54) FOAM-BASED FASTENERS

(75) Inventors: Fung-jou Chen, Appleton, WI (US);
Julie Marie Bednarz, Neenah, WI (US);
Nadezhda Efremova, Neenah, WI (US);
Sheng-Hsin Hu, Appleton, WI (US);
Jeffrey Dean Lindsay, Appleton, WI (US); Lisha Yu, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 882 days.

(21) Appl. No.: 10/956,613

(22) Filed: Sep. 30, 2004

(65) Prior Publication Data

US 2006/0069380 A1   Mar. 30, 2006

(51) Int. Cl.
*A61F 13/15* (2006.01)
*A61F 13/20* (2006.01)

(52) U.S. Cl. .............. 604/391; 604/390; 604/389; 604/387; 604/386; 604/385.03

(58) Field of Classification Search .......... 604/358, 604/385.01, 385.04, 386, 387, 391, 385.03, 604/385

See application file for complete search history.

(56) References Cited

U.S. PATENT DOCUMENTS

| | | | |
|---|---|---|---|
| 458,725 A | 9/1891 | Forrester | |
| 2,787,241 A | 4/1957 | Kelley | |
| 3,093,600 A | 6/1963 | Spencer et al. | |
| 3,171,820 A | 3/1965 | Volz | |
| 3,214,816 A | 11/1965 | Mathison | |
| 3,266,927 A | 8/1966 | Lorenz et al. | |
| 3,338,992 A | 8/1967 | Kinney | |
| 3,341,394 A | 9/1967 | Kinney | |
| 3,397,697 A | 8/1968 | Rickard | |
| 3,485,706 A | 12/1969 | Evans | |
| 3,502,763 A | 3/1970 | Hartman | |
| 3,522,196 A | 7/1970 | Dorier et al. | |
| 3,542,615 A | 11/1970 | Dobo et al. | |
| 3,661,674 A | 5/1972 | Higgs et al. | |
| 3,692,618 A | 9/1972 | Dorschner et al. | |
| 3,708,382 A | 1/1973 | Erb | |
| 3,708,833 A | 1/1973 | Ribich et al. | |

(Continued)

FOREIGN PATENT DOCUMENTS

CA      1 188 101      6/1985

(Continued)

*Primary Examiner*—Tatyana Zalukaeva
*Assistant Examiner*—Susan Su
(74) *Attorney, Agent, or Firm*—H. Michael Kubicki

(57) ABSTRACT

In one embodiment of the present invention, an article has a mechanical fastener and configured is to be worn by a user. The article comprises a body portion configured to be worn by a user. The body portion may include a fibrous landing layer wherein the fibrous landing layer comprises a plurality of fibers. The body portion may also include a foam layer, such that the foam layer has a first surface comprising a plurality of free-stranding struts adapted for engaging at least a portion of the plurality of fibers of the landing layer. The foam layer and fibrous landing layer are capable of being engaged with a Shear Resistance of about 100 grams of force or greater per square centimeter and a Peel Resistance of about 50 grams or less of force per square centimeter.

31 Claims, 40 Drawing Sheets

U.S. PATENT DOCUMENTS

| | | |
|---|---|---|
| 3,802,817 A | 4/1974 | Matsuki et al. |
| 3,849,241 A | 11/1974 | Butin et al. |
| 3,922,455 A | 11/1975 | Brumlik |
| 4,062,915 A | 12/1977 | Stricharczuk et al. |
| 4,100,324 A | 7/1978 | Anderson et al. |
| 4,125,664 A | 11/1978 | Giesemann |
| 4,183,984 A | 1/1980 | Browers et al. |
| 4,216,257 A | 8/1980 | Schams et al. |
| 4,285,343 A | 8/1981 | McNair |
| 4,340,563 A | 7/1982 | Appel et al. |
| 4,366,804 A | 1/1983 | Abe |
| 4,443,513 A | 4/1984 | Meitner et al. |
| 4,540,717 A | 9/1985 | Mahnke et al. |
| RE32,026 E | 11/1985 | Yamashita et al. |
| 4,556,146 A | 12/1985 | Swanson et al. |
| 4,589,876 A | 5/1986 | Van Tilburg |
| 4,608,047 A | 8/1986 | Mattingly |
| 4,631,077 A | 12/1986 | Spicer et al. |
| 4,649,895 A | 3/1987 | Yasuki et al. |
| 4,652,487 A | 3/1987 | Morman |
| 4,655,760 A | 4/1987 | Morman et al. |
| 4,656,196 A | 4/1987 | Kelly et al. |
| 4,657,802 A | 4/1987 | Morman |
| 4,666,948 A | 5/1987 | Woerner et al. |
| 4,687,478 A | 8/1987 | Van Tilburg |
| 4,707,398 A | 11/1987 | Boggs |
| 4,720,415 A | 1/1988 | Vander Wielen et al. |
| 4,741,949 A | 5/1988 | Morman et al. |
| 4,753,649 A | 6/1988 | Pazdernik |
| 4,781,966 A | 11/1988 | Taylor |
| 4,789,699 A | 12/1988 | Kieffer et al. |
| 4,805,275 A | 2/1989 | Suzuki et al. |
| 4,818,464 A | 4/1989 | Lau |
| 4,834,739 A | 5/1989 | Linker, III et al. |
| 4,881,997 A | 11/1989 | Hatch |
| 4,894,060 A | 1/1990 | Nestegard |
| 4,906,263 A | 3/1990 | Von Blucher et al. |
| 4,917,697 A | 4/1990 | Osborn, III et al. |
| 4,965,122 A | 10/1990 | Morman |
| 4,981,747 A | 1/1991 | Morman |
| 4,984,339 A | 1/1991 | Provost et al. |
| 5,005,242 A | 4/1991 | Kennedy et al. |
| 5,011,480 A | 4/1991 | Gossens et al. |
| 5,046,479 A | 9/1991 | Usui |
| 5,053,028 A | 10/1991 | Zoia et al. |
| 5,058,247 A | 10/1991 | Thomas et al. |
| 5,094,559 A | 3/1992 | Rivera et al. |
| 5,100,400 A | 3/1992 | Mody et al. |
| 5,110,649 A | 5/1992 | Morse et al. |
| 5,114,781 A | 5/1992 | Morman |
| 5,190,985 A | 3/1993 | Mäder |
| 5,226,992 A | 7/1993 | Morman |
| 5,234,969 A | 8/1993 | Clark et al. |
| 5,242,436 A * | 9/1993 | Weil et al. ............ 604/385.29 |
| 5,244,482 A | 9/1993 | Hassenboehler, Jr. et al. |
| 5,284,703 A | 2/1994 | Everhart et al. |
| 5,336,545 A | 8/1994 | Morman |
| 5,369,858 A | 12/1994 | Gilmore et al. |
| H1420 H * | 2/1995 | Richardson ............ 604/385.29 |
| 5,389,202 A | 2/1995 | Everhart et al. |
| 5,397,316 A | 3/1995 | Lavon et al. |
| 5,399,219 A | 3/1995 | Roessler et al. |
| 5,413,853 A | 5/1995 | Imashiro et al. |
| 5,419,015 A | 5/1995 | Garcia |
| 5,436,278 A | 7/1995 | Imashiro et al. |
| 5,482,755 A | 1/1996 | Manning |
| 5,518,795 A | 5/1996 | Kennedy et al. |
| 5,520,980 A | 5/1996 | Morgan et al. |
| 5,611,789 A | 3/1997 | Seth |
| 5,622,578 A | 4/1997 | Thomas |
| 5,670,101 A | 9/1997 | Nathoo et al. |
| 5,674,270 A | 10/1997 | Viltro et al. |
| 5,676,652 A | 10/1997 | Hunter et al. |
| 5,681,303 A | 10/1997 | Mills et al. |
| 5,720,740 A | 2/1998 | Thomas |
| 5,728,057 A | 3/1998 | Ouellette et al. |
| 5,728,058 A | 3/1998 | Ouellette et al. |
| 5,728,146 A | 3/1998 | Burkett et al. |
| 5,735,889 A | 4/1998 | Burkett et al. |
| 5,741,318 A | 4/1998 | Ouellette et al. |
| 5,763,044 A | 6/1998 | Ahr et al. |
| 5,782,819 A | 7/1998 | Tanzer et al. |
| 5,817,704 A | 10/1998 | Shiveley et al. |
| 5,827,393 A | 10/1998 | Kinzelmann et al. |
| 5,837,005 A | 11/1998 | Viltro et al. |
| 5,858,515 A | 1/1999 | Stokes et al. |
| 5,860,945 A | 1/1999 | Cramer et al. |
| 5,904,710 A | 5/1999 | Davis et al. |
| 5,906,637 A | 5/1999 | Davis et al. |
| 5,925,072 A | 7/1999 | Cramer et al. |
| 5,968,027 A * | 10/1999 | Cole et al. ............ 604/385.01 |
| 5,979,024 A | 11/1999 | Renwick |
| 5,980,562 A | 11/1999 | Ouellette et al. |
| 6,019,782 A | 2/2000 | Davis et al. |
| 6,024,761 A | 2/2000 | Barone et al. |
| 6,048,326 A | 4/2000 | Davis et al. |
| 6,063,067 A | 5/2000 | Takizawa et al. |
| 6,074,413 A | 6/2000 | Davis et al. |
| 6,096,067 A | 8/2000 | Cramer et al. |
| 6,102,937 A | 8/2000 | Cramer et al. |
| 6,123,717 A | 9/2000 | Davis et al. |
| 6,133,332 A | 10/2000 | Ide et al. |
| 6,205,623 B1 | 3/2001 | Shepard et al. |
| 6,224,364 B1 | 5/2001 | Harvey |
| 6,245,697 B1 | 6/2001 | Conrad et al. |
| 6,248,419 B1 | 6/2001 | Kennedy et al. |
| 6,306,234 B1 | 10/2001 | Barker et al. |
| 6,314,627 B1 | 11/2001 | Ngai |
| 6,336,935 B1 | 1/2002 | Davis et al. |
| 6,343,410 B2 | 2/2002 | Greenway et al. |
| 6,406,466 B1 | 6/2002 | Pozniak et al. |
| 6,436,020 B1 | 8/2002 | Weingand |
| 6,443,525 B1 | 9/2002 | Haupt |
| 6,501,002 B1 | 12/2002 | Roe et al. |
| 6,503,615 B1 | 1/2003 | Horii et al. |
| 6,516,502 B1 | 2/2003 | Moody, III |
| 6,527,711 B1 | 3/2003 | Stivoric et al. |
| 6,541,679 B2 | 4/2003 | Betrabet et al. |
| 6,543,099 B1 | 4/2003 | Filion et al. |
| 6,561,354 B1 | 5/2003 | Fereshtehkhou et al. |
| 6,562,167 B2 | 5/2003 | Coenen et al. |
| 6,564,436 B2 | 5/2003 | Black et al. |
| 6,606,771 B2 | 8/2003 | Curtis et al. |
| 6,608,118 B2 | 8/2003 | Kosaka et al. |
| 6,610,383 B1 * | 8/2003 | Morman et al. ............ 428/152 |
| 6,613,032 B2 | 9/2003 | Ronnberg et al. |
| 6,613,113 B2 | 9/2003 | Minick et al. |
| 6,675,429 B2 | 1/2004 | Carter et al. |
| 6,720,362 B1 | 4/2004 | Park |
| 6,725,512 B2 | 4/2004 | Carter |
| 6,730,069 B2 | 5/2004 | Tanzer et al. |
| 6,735,833 B2 | 5/2004 | Putnam et al. |
| 6,743,213 B1 | 6/2004 | Minato |
| 6,828,354 B2 | 12/2004 | Hähnle et al. |
| 2002/0025753 A1 | 2/2002 | Putnam et al. |
| 2002/0146957 A1 | 10/2002 | Fuller et al. |
| 2003/0077430 A1 | 4/2003 | Grimm et al. |
| 2003/0121128 A1 | 7/2003 | Vanbenschoten et al. |
| 2003/0199844 A1 | 10/2003 | Lavon et al. |
| 2004/0024379 A1 | 2/2004 | Lavon et al. |
| 2004/0086320 A1 | 5/2004 | Policicchio et al. |
| 2004/0097856 A1 | 5/2004 | Cipra et al. |
| 2004/0157036 A1 | 8/2004 | Provost et al. |
| 2004/0161994 A1 | 8/2004 | Arora et al. |

| | | | |
|---|---|---|---|
| 2004/0229067 A1 | 11/2004 | Baggot et al. | |
| 2005/0132518 A1 | 6/2005 | Chen et al. | |
| 2005/0132519 A1 | 6/2005 | Chen et al. | |
| 2005/0136238 A1 | 6/2005 | Lindsay et al. | |
| 2005/0136781 A1 | 6/2005 | Lassig et al. | |
| 2005/0148984 A1 | 7/2005 | Lindsay et al. | |

FOREIGN PATENT DOCUMENTS

| | | |
|---|---|---|
| DE | 1 237 331 | 6/1969 |
| EP | 0 071 671 B1 | 5/1985 |
| EP | 0 191 475 A2 | 8/1986 |
| EP | 0 923 902 A2 | 6/1999 |
| EP | 1 113 518 A1 | 7/2001 |
| GB | 1 443 024 A | 7/1976 |
| JP | 2001-179684 A | 7/2001 |
| WO | WO 91/14731 A1 | 10/1991 |
| WO | WO 91/18574 A1 | 12/1991 |
| WO | WO 97/01310 A1 | 1/1997 |
| WO | WO 97/01312 A1 | 1/1997 |
| WO | WO 97/49361 A1 | 12/1997 |
| WO | WO 98/28118 A1 | 7/1998 |
| WO | WO 98/29063 A1 | 7/1998 |
| WO | WO 98/29064 A1 | 7/1998 |
| WO | WO 98/52458 A1 | 11/1998 |
| WO | WO 99/09917 A1 | 3/1999 |
| WO | WO 99/09918 A1 | 3/1999 |
| WO | WO 99/23160 A1 | 5/1999 |
| WO | WO 99/44254 A1 | 9/1999 |
| WO | WO 00/15697 A1 | 3/2000 |
| WO | WO 01/19302 A1 | 3/2001 |
| WO | WO 01/41622 A2 | 6/2001 |
| WO | WO 01/67911 A2 | 9/2001 |
| WO | WO 01/68019 A1 | 9/2001 |
| WO | WO 02/26872 A1 | 4/2002 |
| WO | WO 03/000104 | 1/2003 |
| WO | WO 2004/049992 | 6/2004 |

* cited by examiner

FOAM-BASED FASTENERS

BACKGROUND

Traditional hook and loop mechanical fasteners are widely used in numerous products and articles such as diapers, shoes, disposable gowns, etc. In spite of their prevalence, they suffer from several drawbacks. The hook material typically is stiff and impermeable, and when used in articles worn on or near the human body, may irritate the skin or be uncomfortable. The hook material typically cannot be stretched or deformed significantly. Further, for some applications, the entanglement of hooks into loop material can frequently be difficult to remove, or may adhere to unintended surfaces. The highly abrasive nature of the hook material can also damage some surfaces. The act of peeling the hooks and loops apart can also result in a loud and unpleasant noise, making it difficult to release a fastener discreetly. Further still, in some applications low peel strength but high in-plane resistance to shear is desired, whereas conventional hook and loop fasteners may offer excessively high peel strength to achieve a given level of in-plane shear resistance.

Variations of hook and loop fasteners have been proposed in which a foam layer is used to engage with hooks, but replacing low-cost, flexible loop material with thicker, generally more expensive foams does not appear to have provided significant advantages, and does not address the known limitations of hook layers. Hook and loop fasteners have also been proposed in which an added foam section provides increased friction for a fastening member in a securing zone, but such proposals have not overcome the inherent limitations of hook materials.

What is needed is an improved mechanical fastener that solves one or more of the aforementioned problems.

SUMMARY

Various features and advantages of the invention will be set forth in part in the following description, or may be obvious from the description.

The present invention provides for an improved mechanical fastener comprising a foam layer and a landing layer, each having an engaging surface, wherein the foam layer comprises an open-celled foam having free-standing struts on the engaging surface of the foam layer that serve as engaging elements that can releasably engage loops or other holes in an opposing landing layer such as a fibrous layer with elevated loop elements rising therefrom. In general, the fastening system of the present invention comprises a foam layer joined to a first surface, and a landing layer (e.g., a porous or fibrous landing layer) joined to a second surface, wherein free-standing struts on the foam layer may engage openings in the porous landing layer, such that the first surface and second surface may be releasably joined by placing the foam layer in contact with the landing layer. The two surfaces may be joined such that substantial in-plane shear force may be resisted. In some embodiments of the present invention, the first and second surfaces may be integrally connected (e.g., part of a single product or material), or may be separate components that are not joined together except through the use of the foam fastening system of the present invention. Both the landing layer and the foam layer may be joined to the first and second surfaces, respectively, by any know means such as adhesives, thermal bonding, entanglement, and so forth.

In many embodiments of the present invention, the foam layer comprises a polymeric foam that is relatively open-celled. This means a significant proportion of the individual cells of the foam are in communication with adjoining cells. The cells in such substantially open-celled foam structures have intercellular openings or "windows" that are large enough to permit ready fluid transfer from one cell to the other within the foam structure.

These substantially open-celled foam structures generally have individual cells defined by a plurality of mutually connected, three dimensionally branched webs. The strands of polymeric material making up these branched webs are referred to herein as "struts." Generally, struts are substantially rodlike elements in the solid matrix of the foam material. Multiple struts join at junctures in the foam material and help define the side or window of the cells making up the foam material.

The foam layer may be a open-celled foam with numerous interconnected struts in which most or all of the windows between cells are open, such as in a reticulated foam. An exposed surface of the foam layer may have numerous free-standing struts connected to the solid network of the foam layer but having a free end capable of engaging a loop or hole in a landing layer. A free-standing strut may be generated in a foam, for example, by severing the solid network of foam material to cut a strut that had been connected at both ends to other portions of the solid network of the foam material, yielding a strut that remains anchored to the foam material at one end, with the other end now forming a free end. Free-standing struts may also be produced by other means during foam manufacture and post-treatment of a foam material.

In one embodiment of the present invention, a surface of a relatively thin foam layer for attachment to a landing layer is prepared from a relatively thick section of foam material by mechanical separation of a relatively thin foam layer from the thick section, such as by cutting or otherwise fracturing the foam material to leave a plurality of free-standing struts with free ends available on a surface of a foam layer, wherein the free-standing struts are capable of engaging the holes or loops of a suitable landing layer. The free-standing struts may be struts that were broken by mechanical action as the relatively thin foam layer is prepared, but the free-standing struts remain attached to the foam layer (e.g., only one end of each such strut is free, with the other end being connected to the solid network of the foam layer).

As an alternative to cutting or fracturing a foam layer away from a larger section of foam material, a surface of an existing foam layer may be treated to have an increased number of free-standing struts by other mechanical actions that break some cells on or near the surface of the foam material and/or remove any skin or film on the surface of the foam material. Such mechanical actions may include physical abrasion (e.g., sanding or rubbing the foam layer and/or surface of the foam material that will become the surface of the foam layer against another surface such as a rotating cylinder), mechanical crushing, needling, picking with a roughened surface having barbs or hooks, laser ablation, flame treatment, application of high-velocity jets of a fluid such as water or air, and the like.

Without wishing to be bound by theory, the principle of operation for a foam layer and landing layer attachment system is believed to be analogous to known hook and loop systems, but wherein the foam layer replaces the hook layer, with the free-standing struts of the foam layer (especially those near the attaching surface of the foam layer) serving the function of hooks in the sense that the free-standing struts may engage the holes or loops of the landing layer and resist in-plane shear. However, because the free-standing struts may generally lack one or more of the geometrical or mechanical properties of conventional hooks in hook and loop fasteners, the free-standing struts may be capable of detaching from a landing layer more easily than may conventional hooks. Further, it is believed that the size and spacing of the free-standing struts of a particular foam material will work best when the landing layer has loops with a compatible geometry. A first landing material that adheres well to a first foam material with very small free-standing struts might not adhere to a second foam material with larger, coarser free-standing struts, but the second foam material may adhere well to a second landing material having larger, loftier loops. While the first foam material may engage the loftier loops of the second landing material, it may only engage the highest loops that are less tightly bound to the surface, and relatively few of the free-standing struts may engage into well anchored portions of the second landing material, thus allowing the foam material to slide relative to the landing material under in-plane shear stress. In general, it is believed that a foam material with a fine structure will adhere best with a landing material having relatively small loops, while a coarser foam material will adhere best with a landing material having coarser, larger loops.

Examples of known hook and loop fasteners, and applications thereof for which the fasteners of the present invention can be adapted, include those disclosed in U.S. Pat. No. 3,708,382, issued to Erb on Jan. 2, 1973; U.S. Pat. No. 4,984,339, issued to Provost et al. on Jan. 15, 1991; U.S. Pat. No. 4,894,060, issued to Nestegard et al. on Jan. 16, 1990; U.S. Pat. No. 5,100,400, issued to Mody et al. on Mar. 31, 1992; and, U.S. Pat. No. 6,543,099, issued to Filion et al. on Apr. 8, 2003, the disclosures of which are each incorporated by reference to the extent they are non-contradictory herewith.

Conventional hook materials typically comprise an impermeable planar base from which a thermoplastic hook rises. A characteristic hook typically has a sturdy base member rising from the planar base, with the base member tapering into a top portion comprising a crook member having a free end that curves downwardly back toward but not reaching the planar base, terminating in a distal end. Many related forms are known, with hooks shaped like the letter "J", mushrooms, palm trees, the letter "T", and so forth.

In contrast to conventional hook materials, the foam layer of the present invention typically does not have an impermeable planar base from which individual free-standing struts rise, but comprises a porous network of struts, free-standing and otherwise, defining cells in the foam layer. While a foam layer may have an impermeable skin, the skin should be remote from the engaging surface of the foam layer, such that a plurality of open cells in the foam layer lie between the engaging surface of the foam layer and the skin of the foam layer. Rather than having substantially uniform hook members that are aligned in one or two directions and typically have uniform height, the free-standing struts at the exposed surface of the foam layer may extend in a wide variety directions and have a distribution of lengths. Rather than having a uniform geometry, the free-standing struts may vary in geometry, including shape and size.

In one sense, the attachment of the free-standing struts in an exposed surface of a foam layer to a landing layer may be viewed as a form of "peg and hole" attachment means, analogous to the attachment of cylindrical rods rising from a surface that can fit into holes of an opposing surface for good in-plane shear resistance without significant resistance to out-of-plane detachment (lifting) forces.

Thus, the foam layer and landing layer may be capable of attachment to one another with high shear resistance but relatively low peel resistance. An attached foam layer and landing layer may, in many embodiments of the present invention, withstand substantial in-plane shear forces without detaching, while also permitting ready detachment by peeling or applying a separation force normal to the plane of the foam and landing layers. Ready detachment during lifting or peeling may be promoted when a substantial fraction of the available free-standing struts are free of hook-like structures, as may be the case when the characteristic shape of the free-standing struts, for example, is rod-like.

Alternatively, in other embodiments of the present invention, the attachment of the foam layer to the landing layer may be characterized by relatively high peel strength or z-direction strength, particularly when the free-standing struts have relatively high stiffness and when a high proportion of the free-standing struts are non-linear (e.g., branched near the terminal (free) end of the free-standing struts or comprising crook-like elements) such that loops in an opposing landing layer may be effectively held by the non-linear free-standing struts to resist detachment during lifting or peeling.

As used herein, a material is said to-be "deformable" if the thickness of the material between parallel platens at a compressive load of 100 kPa is at least 5% greater than the thickness of the material between parallel platens at a compressive load of 1000 kPa.

As used herein, the "Zwick Flexibility" test is a measure of stiffness of a flat foam sample as it is deformed downward into a hole beneath the foam sample. For the test, the foam sample is modeled as an infinite plate with thickness t that resides on a flat surface where it is centered over a hole with radius R. A central force applied to the foam sample directly over the center of the hole deflects the foam sample down into the hole by a distance w when loaded in the center by a Force F. For a linear elastic material the deflection may be predicted by:

$$w = \frac{3F}{4\pi Et^3}(1-v)(3+v)R^2$$

where E is the effective linear elastic modulus, v is the Poisson's ratio, R is the radius of the hole, and t is the thickness of the foam sample, taken as the caliper in millimeters measured under a load of about 0.05 psi, applied by a 3-inch diameter Plexiglass platen, with the thickness measured with a Sony U60A Digital Indicator. Taking Poisson's ratio as 0.1 (the solution is not highly sensitive to this parameter, so the inaccuracy due to the assumed value is likely to be minor), we can rewrite the previous equation for w to estimate the effective modulus as a function of the flexibility test results:

$$E \approx \frac{2R^2}{3t^3}\frac{F}{w}$$

The test results are carried out using an MTS Alliance RT/1 testing machine (MTS Systems Corp., Eden Prairie, Minn.) with a 100 N load cell. As a foam sample at least 2.5-inches square sits centered over a hole of radius 17 mm on a support plate, a blunt probe of 3.15 mm radius descends at a speed of 2.54 mm/min. When the probe tip descends to 1 mm below the plane of the support plate, the test is terminated. The maximum slope in grams of force/mm over any 0.5 mm span during the test is recorded (this maximum slope generally occurs at the end of the stroke). The load cell monitors the applied force and the position of the probe tip relative to the plane of the support plate is also monitored. The peak load is recorded, and E is estimated using the above equation.

The bending stiffness per unit width may then be calculated as:

$$S = \frac{Et^3}{12}$$

The stiffness and modulus measured with the Zwick Flexibility Test are believed to provide useful information about the ability of a material to bend and flex when used on a flexible absorbent article worn on the body, or may indicate the ability of a material to be bent easily during attachment and removal (e.g., peeling off) when used in an attachment system.

The foam materials, foam layers, and composite fastening systems of the present invention may have relatively low bending stiffness (S) values according to the Zwick Flexibility test. For example, the bending stiffness may be about 0.4 Newton-meter (Nm) or less, specifically about 0.1 Nm or less, more specifically about 0.05 Nm or less, more specifically still about 0.02 Nm or less, and most specifically about 0.01 Nm or less, such as from about 0.001 Nm to about 0.1 Nm, or from about 0.002 Nm to about 0.07 Nm. The modulus (E) for the foam materials, foam layers, and composite fastening systems of the present invention may be about 60,000 kPa or less, such as about 30,000 kPa or less, more specifically about 20,000 kPa or less, and most specifically about 7,000 kPa or less.

In one embodiment of the present invention, the foam material by itself (unattached to a reinforcing layer) when provided in a layer having a thickness from about 1 millimeter to about 4 millimeters and having in-plane dimensions of at least 60 mm long in two orthogonal directions, may have a bending stiffness according to the Zwick Flexibility Test of about 0.0003 Nm or greater, such as about 0.0004 Nm or greater, about 0.0006 Nm or greater, about 0.0008 Nm or greater, or about 0.001 or greater.

Definitions:

As used herein, a foam material is "open-celled" if at least 60% of the cells in the foam structure that are at least 1 micrometer (μm) in size are in fluid communication with at least one adjacent cell. In one embodiment of the present invention, at least 80% of the cells in the foam structure that are at least 1 μm in size are in fluid communication with at least one adjacent cell.

As used herein, the term "reticulated foam", as it is commonly used among those skilled in the art, denotes solid foamed materials where substantially all intervening "window walls" or cell membranes have been removed from the cells of the foam, leaving a network consisting primarily of interconnected struts along the outlines of the cells formed during the foaming.

Reticulated foams are thus distinct from foams in which the window walls are merely broken, or foams in which only the outermost window walls or skin have been removed by physical means. Reticulated foams, by virtue of their general lack of cell membranes, are highly permeable to gas and liquid alike, offering little resistance to fluid flow, indeed much less than those foams in which the cell membranes have been retained.

Reticulation is typically achieved by known foam processing procedures applied to the foam after the cells have been formed. These procedures may involve the use of caustic treatments (e.g., see U.S. Pat. No. 3,266,927, issued to Fritz et al. on Aug. 16, 1966), attack by other reactive compounds such as ozone, or thermal treatments of the foam, removing all or substantially all of the "window walls" separating the cells throughout the foam. In some cases, other treatments such as controlled explosions are used to remove membranes around portions of cells (for example, a foam may be packed into an explosion chamber containing an explosive gaseous medium which is then exploded). An example of explosive treatment of a foam is given in U.S. Pat. No. 4,906,263, issued to von Blucher et al. on Mar. 6, 1990.

Needling may also be used to open a closed cell foam material, as described in U.S. Pat. No. 4,183,984, issued to Browers et al. on Jan. 15, 1980. Other methods for creating an open cell foam material are disclosed in U.S. Pat. No. 6,720,362, issued to Park et al. on Apr. 13, 2004.

In one embodiment of the present invention, reticulation is only present in the outer portions of a foam layer at and near the engaging surface.

Alternatively, the cellular foam material may be inherently reticular as made. According to U.S. Pat. No. 3,661,674, issued to Higgs et al. on May 9, 1972, an inherently reticular polyester polyurethane foam may be made, for example, by allowing the foam-forming ingredients to react in the presence of a viscosity-retarding substance such as a further polyester having an acid component which is the same as that of the polyester used to make the foam material but which has a hydroxyl number of between 10 and 100 and a viscosity of less than 200 poises.

As used herein, the term "Denier" refers to a weight-per-unit-length measurement of a linear material defined as the number of grams per 9000 meters. The term may refer to either an individual fiber or a bundle of fibers (yarn).

As used herein, "Decitex" (abbreviated "dtex") is a term similar to denier expect it is the weight in grams of 10,000 meters of a yarn or fiber.

As used herein, the term "hydroentangling" refers to techniques of treating a fabric by application of high-velocity jets of water delivered from high-pressure orifices, whereby the fibers or filaments in the fabric are rearranged under the influence of water impingement. By way of example, U.S. Pat. No. 3,485,706, issued to Evans on Dec. 23, 1969, the disclosure of which is incorporated by reference to the extent that it is non-contradictory herewith, discloses a hydroentanglement process for manufacture of nonwoven fabric webs. During hydroentanglement, the nonwoven fabric web is typically positioned on a foraminous forming surface as it is subjected to impingement by the water jets, whereby the fibers or filaments of the nonwoven fabric web become entangled, thus creating a nonwoven fabric web with coherency and integrity, while the specific features of the forming surface act to create the desired pattern in the nonwoven fabric web. Before leaving the nozzles, the water may have a pressure of up to about 60 Mpa (600 bar). The nozzles may have a diameter of 0.05 to 0.25 mm and may be spaced at 20-160 mesh. The jet hits the nonwoven fabric web surface, penetrates it and flows to the openings in the foraminous surface (the web support) and through suction slots. In this process, the fibers are entangled, which may cause compacting and bonding of the nonwoven fabric web. See also, U.S. Pat. No. 5,389,202, issued to Everhart et al. on. Feb. 14, 1995, the disclosure-of which is incorporated by reference to the extent that it is non-contradictory herewith.

The foraminous surface may be substantially planar or three-dimensional, and may be a perforated metal surface, a metal wire, a polymeric wire or fabric such as a through-drying fabric known in papermaking, or other surface. Related examples of hydroentanglement technology are found, by way of examples, in U.S. Pat. No. 4,805,275, issued to Suzuki et al. on Feb. 21, 1989, where three-dimensional foraminous surfaces are disclosed. See also U.S. Patent Application 2002/0025753, published by Putnam et al. on Feb. 28, 2002.

As used herein, the phrase "cluster of free-standing struts" refers to one or more interconnected struts that extend away from a complete cell of the foam material, wherein the struts in the cluster are connected to the same complete cell. If first and second struts from first and second cells, respectively, join at a juncture and have a third strut (a free-standing strut) extending from the juncture, the first and second struts are considered to be part of a closed cell, and the cluster of free-standing struts would consist of the third strut. If the third strut branches into two other free-standing struts at an end away form the juncture, the third strut and the two other free-standing struts are all part of a cluster of free-standing struts.

As used herein, the term "free length" of a free-standing strut or cluster of free-standing struts is the linear distance the free-standing strut or cluster of free-standing struts, respectively, extends away from the nearest portion of the first complete cell in the foam material attached to the free-standing strut or cluster of free-standing struts.

The Foam Layer

In one embodiment of the present invention, the foam layer comprises an open-celled foam such as a melamine foam, a polyurethane foam, or other known open-celled foams. Such foam materials typically comprise rod-like struts forming a reticulated network that defines cells in the foam materials.

Melamine-based foams may include the foams currently manufactured by BASF, located in Ludwigshafen, Germany, under the BASOTECT® brand name. For example, BASOTECT® 2011, with a density of about 0.01 g/cm$^3$, may be used. Blocks of melamine-based foam are marketed by Procter & Gamble, located in Cincinnati, Ohio, under the MR. CLEAN® brand name. Similar materials are marketed under the CLEENPRO™ name by LEC, Inc., located in Tokyo, Japan, (several product executions are shown at http://www.users.bigpond.com/jmc.au/CLEENPRO/CLEEN-PRO-E.htm and http://www.users.bigpond.com/jmc.au/CLEENPRO/CLEENPRO%20Family-E.htm, both printed on Nov. 13, 2003). Melamine-based foam is also marketed for acoustic and thermal insulation by many companies such as American Micro Industries, located in Chambersburg, Pa.

Examples of potentially useful reticulated foams include the polyurethane reticulated foams of Foamex, Inc., located in Linwood, Pa., such as foam SIF-60z; and, the reticulated foams of the following firms: Crest Foam Industries, Inc., located in Moonachie, N.J., including FilterCrest® reticulated foams; Scottfoam Corporation, located in Eddystone, Pennsylvania; Swisstex, Inc., located in Greenville, S.C.; Recticell, located in Chicago, Ill.; and, the foams produced at Caligen Europe BV, located in Breda, the Netherlands, a subsidiary of British Vita PLC, located in Manchester, England.

Examples of reticulated foams are also disclosed in the patent literature, including U.S. Pat. No. 3,171,820, issued to Volz et al. on Mar. 2, 1965; U.S. Pat. No. 4,631,077, issued to Spicer et al. on Dec. 23, 1986; U.S. Pat. No. 4,656,196, issued to Kelly et al. on Apr. 7, 1987; and, U.S. Pat. No. 4,540, 717 issue to Mahnke et al. on Sep. 10, 1985. Also of potential use are the open-celled foams marketed by Sydney Heath & Son, located in Burslem, Stoke on Trent, United Kingdom, including reticulated foam described as having 75 pores per inch. Reticulated foams may include polyurethane, polyester, and polyether types, as well as other known reticulated foams. Other foams that may be considered include those of U.S. Pat. No. 4,062,915, issued to Stricharczuk et al. on Dec. 13, 1977.

Pore size in commercial open-celled foams is commonly expressed as pores per inch (ppi), based on measurement of the pores along a straight path of known length, which may also be expressed in terms of pores per centimeter (ppc). According to the present invention, the foam material in the foam layer may have an characteristic pore size of any of the following: from about 1 ppc to about 200 ppc; from about 3 ppc to about 180 ppc; from about 10 ppc to about 150 ppc; from about 15 ppc to about 130 ppc; from about 15 ppc to about 100 ppc; or, from about 15 ppc to about 50 ppc.

The free-standing struts of the foam material, by way of example only, may have an effective diameter of about 0.3 microns or greater, such as about 1 micron or greater, about 3 microns or greater, or about 10 microns or greater, such as any of the following: from about 0.3 micros to about 30 microns; from about 1 micron to about 30 microns; from about 3 microns to about 30 microns; from about 1 micron to about 20 microns; and, from about 1 micron to about 10 microns. The free length of a free-standing strut, the free length of a plurality, or cluster, of free-standing struts effective in engaging a landing layer, the free length of a characteristic free-standing strut, the average free length of free-standing struts on a surface of a foam material, or the median free length of free-standing struts on a surface of a foam material, may be any of the following: greater than about 3 microns; greater than about 10 microns; greater than about 20 microns; greater than about 50 microns; greater than about 100 microns; greater than about 500 microns; greater than about 1000 microns; and, greater than about 2000 microns, such as from about 10 microns to about 2000 microns, or from about 50 microns to about 1000 microns, or from about 100 microns to about 500 microns. The ratio of free length of a free-standing strut (or related measures thereof previously discussed) to effective diameter of a free-standing strut may be about 5 microns or greater, 10 microns or greater, 20 microns or greater, 50 microns or greater, and 100 microns or greater, such as from about 5 microns to about 100 microns, or from about 10 microns to about 200 microns.

Other open-celled foam materials may also be considered, such as a layer of an aminoplast foam (e.g., foams made from urea-formaldehyde resins or melamine-formaldehyde resins), a phenolic foam such as a foam made from phenol-formaldehyde resins. Any aminoplast foam or other open-celled foam disclosed in U.S. Pat. No. 4,125,664, issued to Giesemann on Nov. 14, 1978, the disclosure of which is incorporated by reference to the extent that it is non-contradictory herewith, may be used to produce the articles of the present invention. Other foams that may be used within the scope of the present invention include those disclosed in U.S. Pat. No. 4,666,948, issued to Woerner et al. on May. 19, 1987; U.S. Pat. No. 5,234,969, issued to Clark et al. on Aug. 10,1993; U.S. Pat. No. 6,133,332, issued to Shibanuma on Oct. 17, 2000; and, World Patent Application No. WO 91/14731, published by Mäder et al. on Oct. 3, 1991, the disclosures of which are each incorporated by reference to the extent that they are non-contradictory herewith.

In one embodiment of the present invention, the foam layer comprises a thermoset foam, and the thermoset components of the foam layer may comprise over 50%, over 60%, over 80%, or over 90% of the mass of the foam layer. Alternatively, the solid polymeric components of the foam layer may consist essentially of one or more thermoset materials. In another embodiment of the present invention, the foam layer may be substantially free of thermoplastic materials. In another embodiment of the present invention, the foam layer may not comprise more than 50% of any one of a component selected from polyolefin materials, polyurethanes, silicones, and polyesters.

The foam layer may comprise more than one kind of foam. For example, heterogeneous foam layers may be considered with structures or compositions similar to any of those disclosed in U.S. Pat. No. 5,817,704, issued to Shiveley et al. on Oct. 6, 1998, the disclosure of which is incorporated by reference to the extent that it is non-contradictory herewith. Two or more kinds of foam material may be blended or joined together during foam manufacture or existing foams may be laminated or otherwise joined together.

The foam layer may be cut or sliced to any desired thickness, and may be cut to be planar, sinusoidal, or to have other geometric features. Principles for cutting and slicing a foam layer are disclosed in European Patent No. EP 191,475, published by Gotoh et al. on Aug. 20, 1986; U.S. Pat. No. 5,670,101, issued to Nathoo et al. on Sep. 23, 1997, which shows a slicer (object no. 32 in FIG. 3) that slices foam material into multiple layers at once, presumably by the action of multiple cutting blades; and, U.S. Pat. No. 6,245,697, issued to Conrad et al. on Jun. 12, 2001, which discloses the use of a sharp reciprocating saw blade to slice a foam material into thin layers, such as from about 0.5 mm to about 5 mm in thickness.

Another method for slicing foam material to thin small layers (e.g., about 1 mm in thickness or greater) is found in Japanese Patent Application No. JP 2001-179684A, published by Toshiro on Jul. 3, 2001, which discloses joining a reinforcing layer to a foam material prior to slicing to allow the thin layer to be processed more easily. The foam material with a reinforcing layer is compressed in a nip and then encounters a blade that severs a thin layer away from the main body of the foam material. By extension to the present invention, a reinforcing layer, such as a nonwoven web or paper towel, may be adhesively joined to a thick block of foam material, and then pass through a nip and encounter a knife blade oriented to slice away a thin section of foam material attached to the reinforcing layer. The remaining thicker block of foam material could then again be attached to a second reinforcing layer on one side, and the foam material adjacent to the reinforcing layer could be sliced off, as before, and the process could be repeated until the foam material had been substantially cut into a plurality of thin layers attached to a reinforcing layer. Both sides of the initial foam material block may be attached to a reinforcing layer, if desired, optionally allowing the final split to divide a foam material into two thin layers both attached to reinforcing layers.

In addition to being sliced from larger foam material blocks, the foam material may be formed directly in thin layers using methods such as those disclosed in World Patent Application No. WO 98/28118, published by Peterson et al. on Jul. 2, 1998.

The foam material may also be perforated, as may the reinforcing layer. One method for perforating foam materials is disclosed in World Patent Application No. WO 00/15697, published by Park et al. on Mar. 23, 2000. The foam material may also have a plurality of short slits or elongated perforations applied normal to the plane of the foam material, such as the slit materials in U.S. Pat. No. 5,397,316, issued to LaVon et al. on Mar. 14, 1995.

Reinforcing Layer:

The foam layer may be reinforced with an underlying reinforcing layer such as a nonwoven web, a tissue web, a woven fabric, a scrim material, and the like. In one embodiment of the present invention, the reinforcing layer may generally comprise cellulosic fibers and may comprise a paper material such as a latex-reinforced creped towel, an uncreped through-air-dried towel reinforced with wet strength resins or other binding agents, other single-ply or multi-ply tissue structures (multi-ply tissues may generally require interply bonding means such as adhesive attachment for good mechanical integrity), a coform layer comprising wood pulp fibers intermingled with thermoplastic material that has been thermally bonded (e.g., by application of heated air, heated calendering, etc.), and airlaid material comprising bicomponent binder fibers, a hydroknit comprising hydraulically entangled paper fibers on a nonwoven substrate, and the like. The reinforcing layer, such as a web, may comprise a plurality of layers bonded together.

Foam layers joined to reinforcing layers are disclosed in commonly owned U.S. patent application Ser. No. 10/744,238, filed by Chen et al. on Dec. 22, 2003, the disclosure of which is incorporated by reference to the extent that it is non-contradictory herewith. While the products of the Chen et al. application are primarily intended to serve as cleaning devices, the combinations of foam layers and reinforcing layers disclosed therein may be adapted for the present invention.

The reinforcing layer may be coextensive with the foam layer, or may extend across only a portion of the foam layer, or may extend beyond all or any of the lateral sides of the foam layer.

Attachment of the reinforcing web to the foam material may be accomplished by adhesive means suitable for maintaining good flexibility in the article. In addition, the adhesive means may also provide good strength under humid or wet conditions and the stresses typical during use of the article. In one embodiment of the present invention, the adhesive means comprises a water-insoluble hot melt adhesive material having a Shore A hardness of about 95 or less, specifically about 75 or less, more specifically about 55 or less, more specifically still about 40 or less, and most specifically about 30 or less, such as from about 10 to about 95, or from about 20 to about 55. Useful adhesive materials may include, but are not limited to those disclosed in U.S. Pat. No. 6,541,679, issued to Betrabet et al. on Apr. 1, 2003 and U.S. Pat. No. 5,827,393, issued to Kinzelmann et al. off Oct. 27, 1998, as well as the commercial HYSOL® hotmelts of Henkel Loctite Corporation, located in Rocky Hill, Conn., as well as polyolefin, urethane, and polyamide hotmelts. The adhesive material may have a glass transition temperature between about −10° C. and about +30° C. or between about 10° C. and about 25° C. The tensile strength of the adhesive material may be at least about 100 psi, at least about 300 psi, or at least about 500 psi.

In one embodiment of the present invention, the adhesive means may comprise an adhesive material with a plurality of hydrophilic groups suitable for maintaining good adhesion with cellulose material even when the cellulose material is wet. Such adhesive materials may comprise EVA (ethylene vinyl acetate), and may include, by way of example, the EVA HYSOL® hotmelts commercially available from Henkel Loctite Corporation, located in Rocky Hill, Conn., including 232 EVA HYSOL®, 236 EVA HYSOL®, 1942 EVA HYSOL®, 0420 EVA HYSOL® SPRAYPAC®, 0437 EVA HYSOL® SPRAYPAC®, CoolMelt EVA HYSOL®, QuikPac EVA HYSOL®, SuperPac EVA HYSOL®, and WaxPac EVA HYSOL®. EVA-based adhesive materials may be modified through the addition of tackifiers and other conditioners, such as Wingtack 86 tackifying resin manufactured by Goodyear Corporation, located in Akron, Ohio.

In another embodiment of the present invention, the adhesive means comprises an elastomeric adhesive material such as a rubber-based or silicone-based adhesive material, including silicone sealants and latex adhesive materials such as acrylic latex. In one embodiment of the present invention, however, the adhesive means is substantially free of natural latex or proteins associated with natural latex. In another embodiment of the present invention, the adhesive means is substantially free of any kind of latex.

The adhesive means may also comprise fibers or particulates that are either tacky or may be heated to melt a portion thereof for fusing a fibrous web to the foam layers. For example, bicomponent binder fibers may be used, in which the fibers include a sheath having a lower melting point than a core fiber (e.g., a polypropylene or polyethylene sheath around a polyester core). The binder fibers may be applied in a separated loose form, or may be provided as a prebonded fusible web. In one embodiment of the present invention, the adhesive means comprises a combination of adhesive particles or fibers such as bicomponent binder fibers and a hot-melt or reactive adhesive material. For example, bicomponent binder fibers may be present in or on a reinforcing layer prior to application of a hotmelt or other flowable or liquid adhesive (e.g., by spray, extrusions, or printing) to either the reinforcing layer or the foam, followed by joining of the reinforcing layer to the foam layer and optional application of heat or other curing means: The particulate adhesive component may already be active (e.g., partially molten) when the foam is joined to the reinforcing layer.

In general, the adhesive means may be applied by spray nozzles, glue guns, bead applicators, extruders, gravure printing, flexographic printing, ink-jet printing, coating, and the like. The adhesive means may be, but need not be, uniformly applied on either the surface of the foam layer or the surface of the reinforcing layer or both, and may be applied selectively in regions where high strength is needed such as along the perimeter of the interfacial area between the reinforcing layer and the foam layer. The adhesive means may also be applied in a pattern or in a substantially random distribution.

The foam layer may have a thickness about 1 mm to about 15 mm, from about 2 mm to about 12 mm, from about 3 mm to about 10 mm, and from about 4 mm to about 8 mm. The ratio of the thickness of the reinforcing layer to the thickness of the foam layer may be any of the following: from about 1 to about 200; from about 3 to about 10; from about 4 to about 10; from about 0.2 to about 2; from about 0.3 to about 2; from about 0.3 to about 1; less than about 1; greater than about 1; and, from about 0.5 to about 1.5.

The reinforcing layer joined to the foam layer may be a nonwoven web, a tissue web, a film, an apertured web, a laminate, and the like. Suitable nonwoven webs may include meltblown webs, spunbond webs, spunlace webs, and the like. The reinforcing layer may be elastomeric, such as the webs disclosed in U.S. Pat. No. 4,707,398, issued to Boggs on Nov. 17, 1987; U.S. Pat. No. 4,741,949, issued to Morman et al. on May 3, 1988; and, U.S. Pat. No. 5,520,980, issued to Morgan et al. on May 28, 1996. The reinforcing layer may be a neck-bonded laminate or other stretchable laminate.

Alternatively, a foam layer may be produced such that a reinforcing layer is unitary with the foam material itself. For example, a single layer of foam material may be produced with a skin on one side that may reinforce the foam material. Similarly, a foam layer may have substantially closed cells on one side and substantially open cells on the other side. Such a foam layer may be an example of a "gradient foam material" having a gradient in the thickness direction pertaining to a material property such as pore size, openness of the pores, density, etc. Gradient foam materials comprising one side providing a reinforcing function may be produced from foams having a skin on one side or from closed-cell foam materials in which one surface is converted to an open-cell foam material through chemical or mechanical means to remove windows from the foam material and liberate free-standing struts on one surface.

Further, the foam layer may also comprise adhesive material to further enhance bonding of the foam material to a landing layer. The adhesive material may be provided on a tab or extension of a reinforcing layer such that the adhesive treated zone is not on the foam material itself but on an attached portion of another material, or the adhesive material may be present on the surface or within the body of the foam material. In one embodiment of the present invention, viscous adhesive material is present within the foam material but not necessarily on the surface of the foam material, such that adhesive attachment does not occur when the foam material contacts another material unless the foam material is loaded sufficiently to bring the internal adhesive into contact with the other material (e.g., a landing layer). Pressure sensitive adhesive material may be sprayed on the surface of a foam material, or injected or impregnated into the foam material to form spaced-apart deposits within the foam material. An adhesive section attached to a foam layer may be shielded with release paper or other means to prevent premature attachment.

In another embodiment of the present invention, the addition of adhesive means to a foam layer fastening system may help increase the peel strength of the foam layer fastening system, when higher peel is desired.

The Landing Material

The landing material for use in the landing layer of the present invention may be a loop material known in past hook and loop systems, though for best results the size of the loops or holes in the landing layer should be adjusted for effective attachment with the foam layer to be used. The loop material may be a web comprising hook-engageable, free-standing loops extending from at least one surface of the loop material.

The landing material may be a nonwoven web such as a meltspun (meltblown or spunbond web), a needled fibrous web, or a hydroentangled web (e.g., a spunlace web, particularly one with microfibers hydroentangled onto a base fabric). The landing layer may comprise fibrous loops that rise away from the plane of the fabric or lie in the plane of the fabric, making it possible for the loops to be engaged by a suitable opposing surface having free-standing struts of the foam layer.

It has been found that good results may be obtained when the landing layer has numerous loop segments rising from the surface of the fabric with a characteristic loop height greater than about 30 microns, such as about 50 microns or greater, about 80 microns or greater, about 100 microns or greater, or about 150 microns or greater, which may span characteristic ranges such as from about 30 microns to 1000 microns, or from about 50 microns to 700 microns, or from about 80 microns to about 600 microns, or from about 100 microns to about 500 microns. The linear distance on the surface of the fabric between the two ends of an elevated loop segment (or the distance between the points where the loop segments return to the plane of the fabric) may be about 80 microns or greater, such as about 150 microns or greater, about 300 microns or greater, or about 500 microns or greater, with characteristic ranges such as from about 80 microns to about 1000 microns, or from about 100 microns to about 800 microns, or from about 100 microns to about 600 microns. However, other size ranges are also within the scope of the present invention and may be considered, provided that the free-standing struts of the engaging surface of a foam layer are capable of adequate engagement with the loop segments or holes on the engaging surface of the landing layer.

In one embodiment of the present invention, the landing layer comprises loop segments comprising microfibers having an effective fiber diameter of about 30 microns or less, about 20 microns or less, about 10 microns or less, about 5 microns or less, about 2 microns or less, or about 1 micron or less. The fiber diameters of the microfibers may range from about 0.1 micron to about 30 microns, or from about 1 micron to about 30 microns, or from about 1 micron to about 20 microns, or from about 2 microns to about 20 microns. Such microfibers may be produced by known meltblown processes, for example. Bicomponent meltblown fibers, as used herein includes other multi-component conjugate fibers, may be used to obtain extremely fine fibers by splitting the fibers or removing one of the components. Splitting may be done by mechanical or chemical means. For example, a bicomponent side-by-side or pie-segment type fiber may be split using hydroentanglement using high-velocity jets of water to split the multi-component fibers. Chemical treatment to cause swelling of a component (e.g., by application with caustic or other swelling agents) or to dissolve a component may also result in splitting. Steam treatment, microwaves, mechanical straining, and other techniques may also be applied to suitable mutli-component fibers to promote splitting. The bicomponent fibers may be round in cross-section or non-round, such as multilobal fibers, and may be twisted, crimped, helical, or substantially straight. Bicomponent combinations, by way of example only, may include any of the following: polypropylene, polyethylene, polyesters, PBT (polybutyleneterephthalate), polylactic acids, polyamides, PHA, and the like. Additional details on microfiber production are found in U.S. Patent Application Publication No. 2004/0161994 A1, published by Arora et al. on Aug. 19, 2004; the microfibers of the Arora et al. document may also be used within the scope of the present invention.

A landing layers comprising microfibers may be woven textiles or nonwoven fabrics, and may comprise a single type of microfibers or a plurality of microfibers types, and may comprise fibers, webs, or other structural elements others than microfibers. Exemplary materials comprising microfibers that may be considered for use in a landing layer according to the present invention include the following:

Spunlace webs, particularly those comprising microfibers, as manufactured by Polymer Group, Inc. (located at North Charleston, S.C.). Patents and applications assigned to Polymer Group, Inc. (PGI) that involve hydroentangling include U.S. Patent Application Publication No. 2002/0025753, published by Putnam et al. on Feb. 28, 2002; U.S. Pat. No. 6,306,234, issued to Barker et al. on Oct. 23, 2001; U.S. Pat. No. 6,314,627, issued to Ngai et al. on Nov. 13, 2001; U.S. Patent Application Publication No. 2002/0146957, published by Fuller et al. on Oct. 10, 2002; U.S. Pat. No. 6,675,429, issued to Carter et al. on Jan. 13, 2004; U.S. Pat. No. 6,606,771, issued to Curtis et al. on Aug. 19, 2003; U.S. Pat. No. 6,564,436, issued to Black et al. on May 20, 2003; U.S. Pat. No. 6,516,502, issued to Moody et al. on Feb. 11, 2003; U.S. Pat. No. 6,725,512, issued to Carter et al. on Apr. 27, 2004; U.S. Pat. No. 6,735,833, issued to Putnam et al. on May 18, 2004; and, U.S. Pat. No. 6,343,410, issued to Greenway et al. on Feb. 5, 2002, the disclosures of which are each incorporated by reference to the extent that they are non-contradictory herewith. Commercial PGI products that may be used in various embodiments of the present invention include PGI's MediSoft™ fabrics, Comfortlace™ fabrics for feminine hygiene products, said to be made with PGI's Laminar Air Controlled Embossing (LACE) process that adds a 3-D image or bulky surface layer to a reticulated film, and Miratec™ fabrics or other fabrics made with PGI's Apex® hydroentanglement technology in which a 3-D image may be added to a fabric.

Looped material wherein the loops are formed in a landing layer according to U.S. Patent Application Publication No. 2004/0157036A1, published by Provost et al. on Aug. 12, 2004. The loop material is formed by needling a batt of fibers through a carrier sheet such as a plastic film, to form loops on the opposing side of the carrier sheet. A binder, such as a powder resin or plastic film, is placed over the fiber side of the product and fused to the carrier sheet to bond the fibers in place. In some cases the product is needled in only discrete areas, leaving other areas free of loops.

Apertured nonwoven webs made according to U.S. Pat. No. 5,369,858, issued to Gilmore et al. on Dec. 6, 1994. This patent document is a nonwoven fabric comprising at least one layer of textile fibers or net of polymeric filaments and at least one web of melt blown microfibers, bonded together by hydroentangling. The nonwoven fabric may be apertured by hydroentangling or may have areas of higher density and areas of lower density. The technology is assigned to Fiberweb North America located in Simpsonville, S.C.

Microfiber cloths marketed as cleaning cloths, such as Modern Magic® MicroFiber Cleaning Cloths by Modern Plastics, Inc. located in Bridgeport, Conn.; the MicroFiber Cleaning Cloths of TAP Plastics, Inc. located in Stockton, Calif.; or, the Scoth-Brite® MicroFiber Cleaning Cloths of 3M, Inc. located in St. Paul, Minn.

OFO-3 Micro Fiber made by Oimo Industrial Co., Ltd., located in Taipei, Taiwan, a cloth made of mechanically split microfiber made from a PET/nylon bicomponent fiber that is hydraulically needled, splitting the fiber into 166 parts, according to supplier information at http://www.allproducts.com/household/oimo/22-ofo-3.html (viewed on May 17, 2004).

Microfibers may be made from numerous polymers such as cellulose (e.g., lyocell solvent-spun fibers), polyolefins, polyamides, polyesters, PHA, polylactic acid, acrylic, and the like. Microfibers may also include electrospun fibers, which are also referred to as nanofibers.

Known loop materials that may be adapted for use in a landing layer of the present invention include the loop materials disclosed in U.S. Pat. No. 5,622,578, issued to Thomas on Apr. 22, 1997. The loops, as disclosed in the patent document, are manufactured by the process of extruding liquid material through the apertures of a depositing member onto a moving substrate to form the base of the loop, stretching the liquid material in a direction parallel to the plane of the substrate, severing the stretched material to form a distal end which fuses with an adjacent amount of stretched material to form a loop.

Loop materials that may be adapted for use in a landing layer of the present invention may include laminates of nonwoven materials, such as nonwoven webs joined to films or multiple layers of fibrous nonwoven webs. Such laminated may include those disclosed in U.S. Patent Application Publication No. 2003/0077430, published by Grimm et al. on Apr. 24, 2003, the disclosure of which is incorporated by reference to the extent that it is non-contradictory herewith. The laminates disclosed in Grimm et al. document comprise at least one layer of a polyolefin endless filament nonwoven fabric, such as a polypropylene endless filament nonwoven fabric, having a maximum tensile strength in the machine running direction that is at least as great as crosswise to that direction (e.g., in a ratio of about 1:1 to about 2.5:1), and made up essentially of fibers having a titer of less than about 4.5 dtex, such as in the range of about 0.8 dtex to about 4.4 dtex, more specifically from about 1.5 dtex to about 2.8 dtex, as well as a second layer of a nonwoven fabric that is bonded to the first layer, which includes a sheet of crimped, such as two-dimensionally and/or spirally crimped, staple fibers made of polyolefins, and whose crimped fibers are coarser than the fibers of the nonwoven fabric of the first layer, and can have titer of about 3.3 dtex to about 20 dtex, more specifically about 5.0 dtex to about 12.0 dtex, whereby the at least two nonwoven fabric layers may be bonded to one another at the common interface by bonding in the form of a predetermined pattern. The second layer can act as the loop layer in the material of the Grimm et al. document.

Alternatively, the landing layer of the present invention may comprise openings (holes) that may be engaged by free-standing struts in a foam layer. The openings may be pores in the surface of the landing layer defined by surrounding fibers. Such openings may have a characteristic diameter greater than about 0.5 microns (μm), such as from about 0.5 μm to about 3 millimeters (mm), or from about 1 μm to about 2 mm, or from about 2 μm to about 1.2 mm, or from about 4 μm to about 1 mm, or less than about 1 mm. The openings may maintain an effective diameter of about 0.5 microns or greater, about 1 micron or greater, about 2 microns or greater, or about 4 microns or greater, continuously from the surface plane of the landing layer surrounding the opening to a "hole depth" in the landing layer of about any of the following or greater: 2 microns, 5 microns, 10 microns, 50 microns, 100 microns, 300 microns, 600 microns, 1 mm, 2 mm, and 3 mm. If the opening provides a continuous vertical opening adapted to receive a vertically oriented cylindrical free-standing strut of diameter D extending a maximum distance L into the landing layer, the opening may have a Cylindrical Hole Depth of L with respect to a free-standing strut diameter of D. Thus, for an example, a free-standing strut having a maximum diameter of about 50 microns and a height of about 500 microns relative to its base (the region where it connects to two or more other struts) should be able to penetrate about 300 microns into a substantially flat landing layer with openings having a Cylindrical Hole Depth of about 300 microns with respect to a free-standing strut diameter of about 50 microns.

In one embodiment of the present invention, the landing layer comprises fine microfibers that may provide loop elements to engage the free-standing struts of the foam layer. In another embodiment of the present invention, the microfibers are provided in a spunlace web in which microfibers have been hydroentangled on a nonwoven or woven backing layer.

In one alternative embodiment of the present invention, the landing layer may also comprise an open-celled foam material, such as a melamine-based foam layer. It has been found that one foam layer of melamine foam material may engage effective, under some circumstances, with another foam layer of melamine foam material, for the open cells and cell windows of a melamine foam material structure may serve as loops suitable for engaging free-standing struts from another foam layer. In such an embodiment, the foam layer or the landing layer comprising a foam layer may each further comprise a reinforcing layer.

Manufacture of Melamine Foam

Principles for manufacturing melamine-based foam are well known. Melamine-based foams are currently manufactured by BASF, located in Ludwigshafen, Germany, under the BASOTECT® brand name. Principles for production of melamine-based foam are disclosed in EP-B 071,671, published by Mahnke et al. on Dec. 17, 1979. According to Mahnke et al. document, they are produced by foaming an aqueous solution or dispersion of a melamine-formaldehyde condensation product which comprises an emulsifier (e.g., metal alkyl sulfonates and metal alkylaryl sulfonates such as sodium dodecylbenzene sulfonate), an acidic curing agent, and a blowing agent, such as a C5-C7 hydrocarbon, and curing the melamine-formaldehyde condensate at an elevated temperature. The foams are reported to have the following range of properties:

a density according to DIN 53 420 between 4 and 80 grams per liter (g/l), corresponding to a range of 0.004 g/cc to 0.08 g/cc (though for purposes of the present invention the density may also range from about 0.006 g/cc to about 0.1 g/cc, or other useful ranges);

a thermal conductivity according to DIN 52 612 smaller than 0.06 W/m ° K.;

a compression hardness according to DIN 53 577 under 60% penetration, divided by the density, yielding a quotient less than 0.3 $(N/cm^2)/(g/l)$, and preferably less than 0.2 $(N/cm^2)/(g/l)$, whereby after measurement of compression hardness the thickness of the foam recovers to at least 70% and preferably at least 90% of its original thickness;

an elasticity modulus according to DIN 53 423, divided by the density of the foam, under 0.25 $(N/mm^2)/(g/l)$ and preferably under 0.15 $(N/mm^2)/(g/l)$;

a bending path at rupture according to DIN 53 423 greater than 6 mm and preferably greater than 12 mm;

a tensile strength according to DIN 53 571 of at least 0.07 $N/mm^2$ or preferably at least 0.1 $N/mm^2$; and, by German Standard Specification DIN 4102 they show at least standard flammability resistance and preferably show low flammability.

U.S. Pat. No. 6,503,615, issued to Horii et al. on Jan. 7, 2003, discloses a wiping cleaner made from an open-celled foam such as a melamine-based foam, the wiping cleaner having a density of 5 $kg/m^3$ to 50 $kg/m^3$ in accordance with JIS K 6401, a tensile strength of 0.6 $kg/cm^2$ to 1.6 $kg/cm^2$ in accordance with JIS K 6301, an elongation at break of 8% to 20% in accordance with JIS K 6301 and a cell number of 80 cells/25 mm to 300 cells/25 mm as measured in accordance with JIS K 6402. Melamine-based foam materials having such mechanical properties may be used within the scope of the present invention.

Related foam materials are disclosed in U.S. Pat. No. 3,093,600, issued to Spencer et al. on Jun. 11, 1963. Agents are present to improve the elasticity and tear strength of the foam material. Melamine-based foam materials are also disclosed in British Patent No. GB 1,443,024, issued to Russo et al. on Jul. 21, 1976.

A foam material for use in the present invention may be heat compressed to modify its mechanical properties, as described in U.S. Pat. No. 6,608,118, issued to Kosaka et al. on Aug. 19, 2003, the disclosure of which is incorporated by reference to the extent that it is non-contradictory herewith.

Brittle foam materials may be made, as described in German publication DE-AS 12 97 331, from phenolic components, urea-based components, or melamine-based components, in aqueous solution with a blowing agent and a hardening catalyst.

The brittle foam material may comprise organic or inorganic filler particles, such as from about 5% to about 30% by weight of a particulate material. Exemplary particulate materials may include clays such as kaolin, talc, calcium oxide, calcium carbonate, silica, alumina, zeolites, carbides, quartz, and the like. The fillers may also be fibrous materials, such as wood fibers, papermaking fibers, coconut fibers, milkweed fibers, flax, kenaf, sisal, bagasse, and the like. The filler particles or fibers added to the foam material may be heterogeneously distributed or may be distributed homogeneously.

The foam material or a portion thereof may also be impregnated with a material to reinforce or harden the foam material, if desired, such as impregnation with water glass or other silicate compounds, as disclosed in U.S. Pat. No. 4,125,664, issued to Giesemann on Nov. 14, 1978, the disclosure of which is incorporated by reference to the extent that it is non-contradictory herewith. Adhesive materials, hot melts, cleaning agents, bleaching agents (e.g., peroxides), antimicrobials, and other additives may be impregnated in the foam material.

The foam layer may be rectangular in plan view, but may have any other shape, such as semicircles, circles, ovals, diamonds, sinusoidal shapes, dog bone shapes, and the like. The foam layer need not be planar, but may be molded or shaped into three-dimensional topographies for aesthetic or functional purposes. For example, melamine-based foam material may be thermally molded according to the process discussed in U.S. Pat. No. 6,608,118, issued to Kosaka et al. on Aug. 19, 2003, previously incorporated by reference. The Kosaka et al. document, discussed above, discloses molding the foam at 210 to 350 C. (or, more particularly, from 230° C. to 280° C. or from 240° C. to 270° C.) for 3 minutes or longer to cause plastic deformation under load, wherein the foam is compressed to a thickness of about 1/1.2 to about 1/12 the original thickness, or from about 1/1.5 to about 1/7 of the original thickness. The molded melamine foams can be joined to a urethane sponge layer to form a composite material, according to the Kosaka et al. document.

As described by Kosaka et al. document, the melamine-based foam may be produced by blending major starting materials of melamine and formaldehyde, or a precursor thereof, with a blowing agent, a catalyst and an emulsifier, injecting the resultant mixture into a mold, and applying or generating heat (e.g., by irradiation or electromagnetic energy) to cause foaming and curing. The molar ratio of melamine to formaldehyde (i.e., melamine:formaldehyde) for producing the precursor is, according to the Kosaka et al. reference, preferably 1:1.5 to 1:4, or more particularly 1:2 to 1:3.5. The number average molecular weight of the precursor may be from about 200 to about 1,000, or from about 200 to about 400. Formalin, an aqueous solution of formaldehyde, may be used as a formaldehyde source.

Melamine is also known by the chemical name 2,4,6-triamino-1,3,5-triazine. As other monomers corresponding to melamine, there may be used C1-5 alkyl-substituted melamines such as methylolmelamine, methylmethylolmelamine and methylbutylolmelamine, urea, urethane, carbonic acid amides, dicyandiamide, guanidine, sulfurylamides, sulfonic acid amides, aliphatic amines, phenols and the derivatives thereof. As aldehydes, there may be used acetaldehyde, trimethylol acetaldehyde, acrolein, benzaldehyde, furfurol, glyoxal, phthalaldehyde, terephthalaldehyde, and the like.

As the blowing agent, there may be used pentane, trichlorofluoromethane. trichlorotrifluoroethane, and the like. As the catalyst, by way of example, formic acid may be used and, as the emulsifier, anionic surfactants such as sodium sulfonate may be used.

Other useful methods for producing melamine-based foam materials are disclosed in U.S. Pat. No. 5,413,853, issued to Imashiro et al. on May 9, 1995, the disclosure of which is incorporated by reference to the extent that it is non-contradictory herewith. According to Imashiro et al. document, a melamine resin foam of the present invention may be obtained by coating a hydrophobic component on a known melamine-formaldehyde resin foam body obtained by foaming a resin composition composed mainly of a melamine-formaldehyde condensate and a blowing agent. The components used in the present melamine resin foam material may therefore be the same as those conventionally used in production of melamine-formaldehyde resins or their foams, except for the hydrophobic component.

As an example, the Imashiro et al. document discloses a melamine-formaldehyde condensate obtained by mixing melamine, formalin and paraformaldehyde and reacting them in the presence of an alkali catalyst with heating. The mixing ratio of melamine and formaldehyde can be, for example, 1:3 in terms of molar ratio.

The melamine-formaldehyde condensate may have a viscosity of about 1,000-100,000 cP, more specifically 5,000-15,000 cP and may have a pH of 8-9.

As the blowing agent, a straight chain alkyl hydrocarbon such as pentane or hexane is disclosed.

In order to obtain a homogeneous foam material, the resin composition composed mainly of a melamine-formaldehyde condensate and a blowing agent may contain an emulsifier. Such an emulsifier may include, for example, metal alkylsulfonates and metal alkylarylsulfonates.

The resin composition may further contain a curing agent in order to cure the foamed resin composition. Such a curing agent may include, for example, acidic curing agents such as formic acid, hydrochloric acid, sulfuric acid and oxalic acid.

The foam material disclosed by Imashiro et al. document may be obtained by adding as necessary an emulsifier, a curing agent and further a filler, etc. to the resin composition composed mainly of a melamine-formaldehyde condensate and a blowing agent, heat-treating the resulting mixture at a temperature equal to or higher than the boiling point of the blowing agent to give rise to foaming, and curing the resulting foam material.

In another embodiment of the present invention, the foam material may comprise a melamine-based foam material having an isocyanate component (isocyanate-based polymers are generally understood to include polyurethanes, polyureas, polyisocyanurates and mixtures thereof). Such foam materials may be made according to U.S. Pat. No. 5,436,278, issued to Imashiro et al. on Jul. 25, 1995, the disclosure of which is incorporated by reference to the extent that it is non-contradictory herewith, which discloses a process for producing a melamine resin foam material comprising a melamine/formaldehyde condensate, a blowing agent and an isocyanate. One embodiment of the present invention includes the production of a melamine resin foam material obtained by reacting melamine and formaldehyde in the presence of a silane coupling agent. The isocyanate component used in U.S. Pat. No. 5,436,278 document may be exemplified by CR 200 (a trademark of polymeric-4,4'-diphenylmethanediisocyanate, produced by Mitsui Toatsu Chemicals, Inc.) and Sumidur E211, E212 and L (trademarks of MDI type prepolymers, produced by Sumitomo Bayer Urethane Co., Ltd). One example therein comprises 100 parts by weight of melamine/formaldehyde condensate (76% concentration), 6.3 parts sodium dodecylbenzenesulfonate (30% concentration), 7.6 parts pentane, 9.5 parts ammonium chloride, 2.7 parts formic acid, and 7.6 parts CR 200. A mixture of these components was placed in a mold and foamed at 100° C., yielding a material with a density of 26.8 kg/m$^3$ (0.0268 g/cm$^3$), a compression stress of 0.23 kgf/cm$^2$, and a compression strain of 2.7%. In general, the melamine-based foam materials discussed in U.S. Pat. No. 5,436,278 document typically had a density of 25 kg/m$^3$-100 kg/m$^3$, a compression strain by JIS K 7220 of 2.7%-4.2% (this is said to be improved by about 40%-130% over the 1.9% value of conventional fragile melamine foam materials), and a thermal conductivity measured between 10° C. to 55° C. of 0.005 kcal/m-h-° C. or less (this is far smaller than 0.01 kcal/m-h-° C. which is said to be the value of conventional fragile foam materials). Other foam materials comprising melamine and isocyanates are disclosed in the World Patent Application No. WO 99/23160, published by Sufi on May 14, 1999, the U.S. equivalent of which is U.S. patent application Ser. No. 98/23864, the disclosure of which is incorporated by reference to the extent that it is non-contradictory herewith.

In another embodiment of the present invention, a melamine-based foam material may be used that is produced according to the World Patent Application No. WO 0/226872, published by Baumgartl et al. on Apr. 4, 2002. Such foam materials have been tempered at elevated temperature to improve their suitability for use as absorbent articles in proximity to the human body. During or after the tempering process, further treatment with at least one polymer is disclosed, the polymer containing primary and/or secondary amino groups and having a molar mass of at least 300, although this polymer treatment may be skipped, if desired, when the foam materials discussed in the WO 0/226872 document are applied to the present invention. Such foam materials may have a specific surface area determined by BET of at least 0.5 m$^2$/g. Exemplary phenolic foam materials include the dry floral foam materials made by Oasis Floral Products, located in Kent, Ohio, as well as the water-absorbent open-celled brittle phenolic foam materials manufactured by Aspac Floral Foam Company Ltd., located in Kowloon, HongKong, partially described at http://www.aspachk.com/v9/aspac/why_aspac.html. Open-cell phenolic foam materials may be made from the phenolic resins of PA Resins, located in Malmö, Sweden, combined with suitable hardeners (e.g., an organic sulfonic acid) and emulsifiers with a blowing agent such as pentane. Phenolic resins may include resole resins or novolac resins, for example, such as the Bakelite® Resin 1743 PS from (Bakelite AG, located in Iserlohn-Letmathe, Germany, which is used for floral foam materials.

Self-Attachment

In several useful embodiments of the present invention, a self-attachment material is provided that comprises both a foam layer and a landing zone disposed on opposing sides of the self-attachment material (e.g., a first surface and a second surface that are integrally joined prior to attachment of the two surfaces with the foam attachment system of the present invention). In one embodiment of the present invention, the self-attachment material is a laminate of a foam layer and a landing layer such as a fibrous loop layer. The foam layer may be provided with free-standing struts rising from an exposed first outer surface of the foam layer. The landing layer serves to provide a second outer surface opposite the first outer surface. When the foam layer (the first outer surface) of the self-attachment material is brought into contact with the landing layer (the second outer surface) of the self-attachment material, effective attachment is possible.

The laminate of the foam layer and the landing layer may be produced by any known means, such as by adhesive bonding, ultrasonic bonding, thermal bonding, hydroentanglement, needling, laser bonding, and fastening by the use of mechanical fasteners such as conventional hook and loop materials. While the foam layer may be joined to the landing layer by engagement of free-standing struts into loops or holes of the landing layer alone, in other embodiments of the present invention, another attachment means may be used to provide greater z-direction bonding strength or peel resistance such that the laminate will not readily come apart under peel forces or other lifting forces (e.g., z-direction forces).

In one embodiment of the present invention, the self-attachment material is provided in roll form. When provided as a roll, a length of the self-attachment material may maintain its roll form without readily unrolling because of the attachment force between adjacent first and second outer surfaces of the self-attachment material.

In another embodiment of the present invention, the self-attachment material in a roll form may be a cleaning material comprising a cleaning foam material (e.g., a melamine-based foam material) joined to a fibrous reinforcing layer, such as the cleaning materials described in commonly owned U.S. patent application Ser. No. 10/744238, filed by Chen et al. on Dec. 22, 2003, the disclosure of which is incorporated by reference to the extent that it is non-contradictory herewith. The cleaning foam material may be placed in a paper-towel dispenser, for example, with perforated sections being removed as needed for cleaning purposes.

In another embodiment of the present invention, the self-attachment material may serve as a sponge-substitute in a roll, with an absorbent fibrous portion comprising a landing layer as a second outer surface, with an opposing foam layer. For example, a melamine foam layer laminated to an absorbent web and an outer meltblown cover (thereby forming composite material), with the meltblown cover capable of good attachment to the foam layer, may be converted into a roll form in which the rolled composite material does not readily unroll itself due to the self-attachment between adjacent layers of the composite material.

U.S. Pat. No. 5,518,795, issued to Kennedy et al. on May 21, 1996, discloses a hook-based fastener strip laminated to a second strip, which may be adapted according to the present invention. U.S. Pat. No. 6,248,419, issued to Kennedy et al. on Jun. 19, 2001, describes a hook material laminated to a loop material, where may also be adapted for the present invention by laminating a foam layer to a suitable landing layer.

Self-Regeneration

In some embodiments of the present invention, the foam layer may be repeatedly used even after abrasion, wear, or repeated usage has caused the loss or damage of the originally present free-standing struts. The self-regenerating feature of the engaging surface of the foam layer is due to the fracturing or breaking of other struts that originally defined open-cells in the foam material. Thus, the mechanical processes that may break original free-stranding struts may create new free-standing struts as the foam material is worn or fractured away in the foam layer. As long as sufficient foam material remains in the foam layer (e.g., foam material having a depth of about two or more characteristic open-cell diameters, or about four or more characteristic open-cell diameters), new free-standing struts may be created. Of course, as the foam material is worn away, tensile strength and other mechanical properties of the foam material may be altered, making failure more likely in many cases, but a sufficiently thick initial layer of foam material may, in some embodiments of the present invention, be fastened and released many times without substantial loss of its ability to engage a suitable landing layer.

Applications

The fastener systems of the present invention, such as foam layer and landing layer fasteners of the present invention, may be used for any known application of hook and loop fasteners and for many applications of other known mechanical or adhesive fasteners, particularly those in which releasable attachment means are needed that must resist in-plane shear forces to maintain a connection between two opposing surfaces. For example, foam layer fasteners may be used to replace hook and loop materials such as VELCRO® products in numerous disposable, reusable, and durable articles.

Absorbent Articles and Disposable Garments

The fasteners of the present invention may be used in absorbent articles such as diapers, incontinence pants, menstrual pants, disposable training pants and prefastened absorbent articles for children such as HUGGIES® PULL-UPS®, sanitary napkins, pantiliners, ostomy bags, sweat absorbent materials, and the like. Other disposable garments may also be considered, such as medical gowns for use by patients or physicians. When used as a releasable attachment means in absorbent articles and disposable garments, and in many other applications, the fasteners may comprise at least one of the foam layer and the landing layer disposed on a flexible member that extends away from the remaining portion of the article. For example, in diapers and other absorbent articles, the foam material may replace hook materials that are commonly disposed on a tab attached to the main body of the diaper. The tab may comprise a support layer bonded to the body of the absorbent article or comprising an extended portion of the body of the absorbent article, such as a portion of a backsheet that extends outwardly where it is bonded to the foam layer for attachment to a landing surface on the outer body of the diaper.

Tabs and other structures onto which one or more members of the fasteners of the present invention are attached may often be described in more detail with reference to geometric characteristics. In one aspect, the present invention concerns a foam layer fastener that defines a fastener longitudinal direction, a fastener lateral direction, and a third direction. The fastener longitudinal direction is the direction that is parallel to the centerline of an absorbent article when a foam layer fastener is attached to an absorbent article and generally corresponds to the "y" direction of the foam layer fastener. The fastener lateral direction is the direction that is perpendicular to the centerline of an absorbent article when a foam layer fastener is attached to an absorbent article and generally corresponds to the "x" direction of the foam layer fastener. The third direction is the direction that is perpendicular to the plane defined by both the fastener lateral direction and the fastener longitudinal direction, and generally corresponds to the "z" direction of the foam layer fastener. The foam layer fastener comprises a flexible layer and at least one discrete fastener island. The fastener island has a planar perimeter edge, a foam fastening material, and a backing material attached to the foam fastening material. The backing material is embedded within the flexible layer and the planar perimeter edge is surrounded by the flexible layer. The planar perimeter edge is the outermost edge of the fastener island along a plane defined by the lateral and longitudinal direction, and is perpendicular to the third direction. As such, the planar perimeter edge defines the edge of the fastener island at its largest cross section.

In general, principles for using hook and loop materials may be readily adapted for use with foam layer and landing layer fasteners. Examples of hook and loop materials in absorbent articles are given in U.S. Pat. No. 5,782,819, issued to Tanzer et al. on Jul. 21, 1998; U.S. Pat. No. 6,730,069, issued to Tanzer et al. on May 4, 2004; U.S. Pat. No. 5,053,028, issued to Zoia et al. on Oct. 1, 1991; U.S. Pat. No. 5,720,740, issued to Thomas on Feb. 24, 1998; and, U.S. Pat. No. 6,743,213, issued to Minato et al. on Jun. 1, 2004.

In one application, the fastening system of the present invention may be used to close a used absorbent article after it is removed, prior to discarding. Such absorbent articles may have two sections of foam material for attaching the article to the body, and another section of foam material to fasten the folded-up or rolled-up used article in place. One or more of the foam material sections may be replace by hook material. Principles for placing mechanical fasteners on a diaper to assist in disposal of the used absorbent article are disclosed in U.S. Pat. No. 6,613,032, issued to Ronnberg et al. on Sep. 2, 2003 and U.S. Pat. No. 6,063,067, issued to Takizawa et al. on May 16, 2000.

In such applications, the foam layer may be provided as spaced apart sections of foam material on a stretchable or elastomeric backing layer such that the foam layer may be joined to an elastomeric or stretchable landing layer with good integrity during use, or so that the foam layer may be stretched prior to attachment for improved fastening. The World Patent Application No. WO 01/68019, published by Provost et al. on Sep. 20, 2001 discloses stretchable fasteners in which fastener tape bands are spaced apart and attached to an elastic web. Such teachings may be adapted to provide spaced apart foam segments for purposes of the present invention. Related teachings are also found in World Patent Application No. WO 01/67911, published by Krantz et al. on Sep. 20, 2001 and in U.S. Pat. No. 5,763,044, issued to Ahr et al. on Jun. 9, 1998.

The fastener systems of the present invention may also be used in feminine care pads or pantiliners to attach the articles to undergarments, including the attachment of wings to undergarments or one to another. One example of such absorbent articles that may be adapted according to the present invention (replacing hook materials with foam layers of the present invention) is given in U.S. Patent. No. 5,676,652, issued to Hunter et al. on Oct. 14, 1997.

The foam layer fastener system of the present invention may also be used to secure removable components of an absorbent article, such as any of the absorbent article systems disclosed in U.S. patent application Ser. No. 10/308,430, filed by LaVon et al. on Dec. 3, 2002, the PCT equivalent of which published on Feb. 5, 2004 as U.S. Patent Application No. 2004/0024379A1, and on Feb. 12, 2004 as U.S. Patent Application No. 2004/0024379A1. The LaVon et al. documents, disclose an absorbent article having a chassis, a non-removable absorbent core component disposed in a crotch region of the chassis, and a replaceable absorbent core component disposed in capillary liquid communication with the non-removable absorbent core component. The replaceable absorbent core component may be removed and a like component may be substituted in place of the removed component without the removal of the absorbent article from the wearer. The replaceable absorbent core component may be disposed inside an openable chassis pocket, with access for its removal and replacement provided by an aperture in a backsheet, an openable end of an external pocket, or an openable end of an internal pocket formed at an area of a waist end edge where the backsheet and a topsheet may be separated. Additional replaceable absorbent core components may also be incorporated. As adapted for the present invention, any removable component of an absorbent article may be secured in use through the foam layer fastener systems of the present invention. For example, a removable absorbent core may comprise a nonwoven web that may engage with a foam layer attached to the chassis or other non-removable portion of the absorbent article to prevent slipping of the removable portion in use.

Thermal Wraps

In one embodiment of the present invention, for example, a foam layer fastener may replace or supplement the mechanical fasteners used in commercial thermal wrap articles such as THERMACARE® Air Activated Thermal Wraps manufactured by Procter & Gamble Corporation located in Cincinnati, Ohio or HEAT ZONE®, commercially available from AccuFitness located in Englewood, Colo., or ACE® bandage or wrap commercially available from Becton Dickenson located in Franklin Lakes, N.J. Such wrap articles may be disposable (e.g., single use wrap articles that are discarded in their entireties after use), durable, or semi-durable (e.g., a wrap articles may be durable while a detachable heating element is disposable). Such wrap articles may be used as knee wraps, neck wraps, back wraps, and menstrual pain relief compresses, for example. Some versions of such wrap articles may comprise stretchable portions joined to VEL-CRO® materials, allowing the wrap article, for example, to held in place around a member of the body by connecting a patch of VELCRO® hook material to a web layer in the wrap article comprising loops adapted for attachment to the hook material. Principles for construction of several types of wrap articles and for construction of heating components are given in U.S. Patent Application No. 2004/0097856, published by Cipra et al. on May 20, 2004.

Another related patent include U.S. Pat. No. 6,024,761, issued to Barone et al. on Feb. 15, 2000. According to the U.S. Pat. No. 6,024,761 document, the disposable elastic thermal uniaxial joint wraps disclosed therein comprise a piece of flexible material having an outer surface, a body-facing surface, a first end, a second end, a body portion, a first strap portion, a second strap portion, wherein at least one of body portion, first strap portion, and second strap portion comprise an elastic portion stretchable along a longitudinal axis of the piece of flexible material, and one or more heat cells comprising an exothermic composition, which preferably substantially fills the available cell volume within the cell.

Further, according to the U.S. Pat. No. 6,024,761 document, the elastic portion of the flexible material comprises a laminate structure having a first carrier layer, a second carrier layer, and a mesh disposed between the first and second carrier layers. The mesh is preferably elastic in at least one direction and comprises a plurality of first strands intersecting a plurality of second strands, wherein first and second strands have softening temperatures, at an applied pressure, such that at least 10% of first strands are integrally bonded to first and second carrier layers by application of a bonding pressure at the softening temperature of the first strands.

The piece of flexible material has a length great enough to encircle a user's knee and/or elbow such that the first and second ends overlap when the flexible material is in a relaxed or stretched state. (The flexible material, however, can be adapted for placement on any other part of the body or for use on animals such as horses, cows, pets, elephants, and the like.) The first and second ends comprise a reclosable fastening means, preferably a hook and loop fastening system, for attaching the first end to said piece of flexible material in order to hold said piece of flexible material around the user's knee or elbow. More preferably, according to the U.S. Pat. No. 6,024,761 document, the fastening means comprises a two-part fastening means which additionally comprises a plurality of hook members which engage loop fibers of a landing zone attached to, or part of, the piece of flexible material in order to adjust the wrap to a variety of user sizes and to attain a comfortable level of elastic tension. However, for purposes of the present invention, the hook and loop two-part fastening means may be replaced with a foam layer and landing layer fastener system. The foam material may take the place of the hook material, and the landing layer may take the place of the loop material in the landing zone. In some embodiments of the present invention, the loop material of existing thermal wraps may have suitable loops for effective engagement of the free-standing struts of the foam material, so the minimum change required to the wrap article, if adapted according to the present invention, may simply be replacing the hook material with a foam layer of the present invention. The replacement foam layer may be, for example, a foam material having similar in-plane dimensions as the hook material it replaces, or the foam material may be greater or smaller in its in-plane dimensions, and greater or smaller in thickness, though for many embodiments of the present invention, the thickness of a foam layer may be best suited for good attachment when it is somewhat thicker than typical hook materials (e.g., having a thickness of about 2 mm or greater).

The loop material of a thermal wrap article according to the present invention may comprise a facing material attached to an elastic web, or may be an inherently elastic loop material.

The thermal wrap article may comprise one or more thermal packs, which may be embedded in the piece of flexible material, to apply thermal energy to a targeted site on the user's body. The thermal pack or packs may comprise a unified structure comprising at least one continuous layer of a coextruded film, optionally comprising a first side of polypropylene and a second side comprising a low melt temperature polymer, which has different stiffness characteristics over a range of temperatures. The thermal pack or packs further may comprise a plurality of individual heat cells which provide a controlled and sustained temperature and which may be adapted to reach their operating temperature range quickly. The heat cells may be spaced apart and fixedly attached within each thermal pack. Each thermal pack may be adapted to provide good drapability while maintaining sufficient rigidity to maintain structural support of the heat cells and to prevent unacceptable stretching of the continuous layer or layers during processing or use. The heat cells may comprise a mixture of powdered iron, powdered carbon, water, and metal salt, which when exposed to oxygen, may provide heat for several hours.

Other heating sources may also be considered, including other exothermic chemical reactions, battery-powered heating, fuel cells, and the like. In some cases, the heat source may be turned on or off, or have its heat flux or temperature adjusted by the user. For example, adding on-off functionality to a thermal wrap article may be achieved by using a flexible source of electrical power that may be turned on or off, and optionally, may be adjusted to deliver a desired temperature or heat flux within a specified range. Fuel cells have been developed by NEC of Japan (see http://www.computerworld.com/mobiletopics/mobile/laptops/story/0,10801,82632, 00.html) for providing up to 40 hours of power to laptop computers by oxidation of methanol, and it is proposed that such fuel cells may be adapted to have a thin, flexible or body-conforming encasement to deliver power upon demand to heat resistive elements in a thermal wrap article, or to deliver heat directly via controlled methanol reaction. One possibility for a more flexible flue cell design is disclosed in World Patent Application No. WO 99/44254, published by Ketcham et al. on Sep. 2, 1999, which relies on thin, flexible ceramic layers in a fuel cell. See also European Patent No. EP 1,113,518, issued to Helfinstine et al. on Jul. 4, 2001. Other flexible sources of electrical power include the laminated film batteries of PowerPaper, Ltd. Located in Einat, Israel (see PowerPaper.com). Other suitable thin-film batteries for RFID sensors and other sensors of the present invention include those of Infinite Power Solutions located in Golden, Colo. Batteries may be recharged, if desired, and may be recharged while in use. Recharging methods may include wireless methods such as collecting energy from an RF power source.

The thermal wrap article may comprise resistive heating elements embedded in a deformable gel. The gel may be conformed against the body for comfort and effective thermal therapy. In one embodiment of the present invention, the gel may be initially cooled or heated before application, and then electric heating or cooling systems may be applied during use to maintain or modify the temperature or heat flux, as desired.

By using electrical power, thermal wrap articles need not be limited to heating, but may also incorporate thermoelectric cooling devices such as commercially available devices based on the Peltier effect. In one embodiment of the present invention, a single wrap article may comprise both cooling and heating capability, using, for example, a combination of resistive or thermoelectric heaters and thermoelectric coolers. The user may then select whether heating or cooling was desired, or may program some of the coolers and some of the heaters to be active simultaneously, or may specify a transition from heating to cooling or visa versa over time according to pre-programmed commands or by manually adjusting the system in use.

The wrap article may further comprise temperature sensors, heat flux sensors, and other sensors such as those used in the wearable sensors marketed by BodyMedia, located in Pittsburgh, Pa., and described in U.S. Pat. No. 6,527,711, issued to Stivoric et al. on Mar. 4, 2003. Such sensors, operatively associated with a control system, may be used to prevent excessive heat from being applied to the body of the user and may allow the user to ensure that effective heat treatment is applied. A control system may also regulate the applied heat over time according to a predetermined or user-specified sequence, such as a periodic cycle of elevated temperatures, or a gradual ramp up to a fixed temperature or heat flux.

Other examples of thermal wrap articles incorporating typical hook and loop fasteners, each of which may be adapted according to the present invention to employ foam layer and landing layer fastener systems, are disclosed in the following: U.S. Pat. No. 6,123,717, issued to Davis et al. on Sep. 26, 2000; U.S. Pat. No. 5,925,072, issued to Cramer et al. on Jul. 20, 1999; and, U.S. Pat. No. 5,904,710, issued to Davis et al. on May 18, 1999. Other thermal wrap articles are disclosed in U.S. Pat. No. 6,436,020, issued to Weingand on Aug. 20, 2002.

Disposable heat packs based on iron oxidation are described in U.S. Pat. Nos. 4,366,804; 4,649,895; 5,046,479; and, U.S. Reissue Pat. No. 32,026. Other disposable body wrap articles have been described in such references as U.S. Pat. Nos. 5,728,057; 5,728,058; 5,860,945; 6,048,326; 5,728,146; 5,735,889; 6,102,937; 6,123,717; 5,925,072; 6,074,413; 5,741,318; 5,980,562; 5,674,270; 5,837,005; 6,096,067; 6,019,782; 5,906,637; 6,024,761; 5,904,710; and, 6,336,935; as well as World Patent Application No. WO 98/29064; World Patent Application No. WO 97/01312; World Patent Application No. WO 97/01310; World Patent Application No. WO 97/49361; World Patent Application No. WO 98/29063; World Patent Application No. WO 99/09917; World Patent Application No. WO 99/09918; and, World Patent Application No. WO 01/19302. These references disclose disposable body wrap articles comprising a plurality of heat cells for warming an afflicted area of the body. In each of these and other previously cited references pertaining to thermal wrap articles, the attachment means of the present invention may be adapted for holding the wrap articles in place and/or for releasably holding a heating element in place in the wrap article.

Other Applications

The fastening systems of the present invention may also be adapted to join components of upholstery together, following principles disclosed in U.S. Pat. No. 5,005,242, issued to Kennedy et al. on Apr. 9, 1991. Foam layer and landing layer fastener systems may also be used to join automotive components known to be suitable for the use of hook and loop fasteners, such as attaching floor mats to a floor or garage door openers to a surface of the automobile.

Foam layer fastener systems may be used to improve the attachment of wipes to cleaning tools such as dry wipes or wet wipes that are attached to the SWIFFER® brand dry mops or wet mops, manufactured by Procter and Gamble located in Cincinnati, Ohio. Principles for the construction of such mops and related mops with disposable elements that may be adapted for fastening according to the present invention are disclosed in U.S. Patent Application No. 2004/0086320, published by Policicchio et al. on May 6, 2004; U.S. Pat. No. 5,419,015, issued to Garcia et al. on May 30, 1995; and, U.S. Pat. No. 5,094,559, issued to Rivera et al. on Mar. 10, 1992. The Garcia et al. document, for example, discloses a mop having a head attached to a handle and a rectangular work pad removably attached to a rectangular flat surface of the head by fabric hook fasteners. The hook fasteners are located in recessed areas of the corners so that the hooks extend downwardly slightly below the lower surface of the head so that the work pad is substantially parallel and juxtaposed with the lower surface of the head throughout contact therebetween. As adapted according to the present invention, such a mop would comprise a head attached to a handle and a cleaning pad removably attachable to the head via a foam layer fastener. A foam layer attached to the mop head may be capable of attaching to an engagement side of a fibrous cleaning wipe having a plurality of loop members. When attached, the cleaning wipe would remain attached to the mop head during use, resisting the levels of in-plane shear typical for mopping, but could readily be detached when peel or lifted away from the mop head.

Improved mop systems with mechanical fasteners for joining mop components are disclosed in commonly owned U.S. patent application Ser. No. 10/739530, filed by Chen et al. on Dec. 18, 2003 and in commonly owned U.S. patent application Ser. No. 10/743261, filed by Chen et al. on Dec. 22, 2003, the disclosures of which are each incorporated by reference to the extent that they are non-contradictory herewith and both of which may be modified according to the present invention by replacing one or more of the mechanical fastening elements therein with the foam layer fastening system of the present invention. Applications for gecko-like mechanical fasteners for mops and other devices are disclosed in commonly owned U.S. patent application Ser. No. 10/747923, filed by Lindsay et al. on Dec. 29, 2003, the disclosure of which is incorporated by reference to the extent that it is non-contradictory herewith; such applications of gecko-like fasteners for mops and other articles disclosed therein may be adapted according to the present invention by using foam layers with opposing landing layers instead of gecko-like fasteners.

A variety of additional applications are disclosed in U.S. Pat. No. 6,205,623, issued to Shepard et al. on Mar. 27, 2001. In the Shepard et al. document, a composite hook and loop fastener is used to form a wrap article tie said to be suitable for many products. The fastener is in the form of an elongated strip having an elongated loop component, a hook component permanently affixed to the loop component, and a backing layer disposed on a face of the wrap article tie in a discrete region. The backing layer is used for permanent attachment of the wrap tie to a supporting surface. One end of the loop component is available for encircling an object to be wrapped and engaging the fastener elements of the hook component. The loop component has a self-supporting web of entangled fibers, the fibers forming both a sheet-form body and hook-engageable, free-standing loops extending from at least one surface of the body, and the hook component has fastener elements extending from a common base. In accordance with the present invention, the hook component may be replaced with a foam layer having free-standing struts attached to the foam material and available at an engaging surface of the foam layer. The backing layer may be a pressure sensitive adhesive or a synthetic resin.

Wrap article ties adapted according to the Shepard et al. document or other wrap article ties comprising foam-based fasteners according to the present invention may be used for re-usable bag closures, closures for umbrellas, labels that may attach to a handle or other component of an article such as a suitcase.

Joining Fasteners to the Articles

Any known method may be used to join the fasteners of the present invention to various articles (i.e., to join a landing layer to one surface and a foam layer to another surface), including the use of adhesives, thermal bonding, ultrasonic bonding, entanglement, mechanical fasteners in general including hook and loop or foam and loop materials, and so forth. In one embodiment of the present invention, an article may be molded (e.g., injection molded) with a foam layer fastener in place. Principles for foaming foam objects with mechanical fasteners in place are disclosed in U.S. Pat. No. 4,881,997, issued to Hatch et al. on Nov. 21, 1989, the disclosure of which is incorporated by reference to the extent that it is non-contradictory herewith. Principles for injection molding articles to incorporate mechanical fasteners are disclosed in U.S. Pat. No. 6,224,364, issued to Harvey et al. on May 1, 2001, the disclosure of which is incorporated by reference to the extent that it is non-contradictory herewith.

BRIEF DESCRIPTION OF THE DRAWINGS

FIG. 30 shows the geometry of a side view of a curved section of the apparatus of FIG. 29.

DETAILED DESCRIPTION

Figure 1:
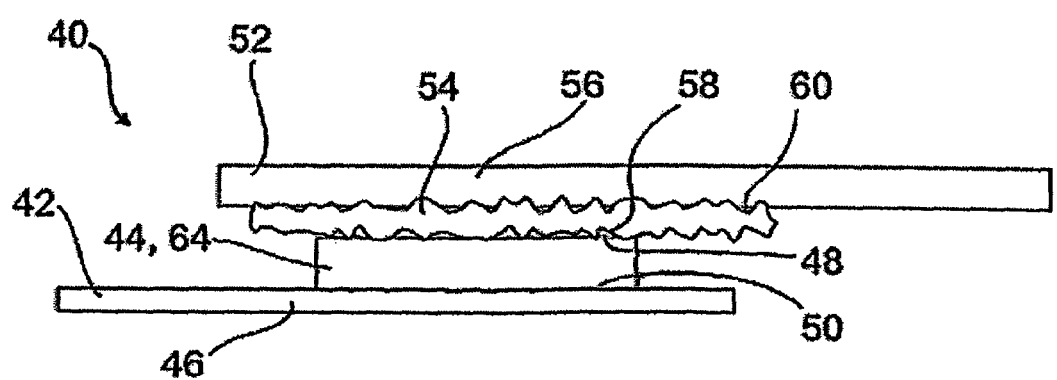
FIG. 1 depicts a cross-sectional view of a foam layer fastening system according to the present invention.

Reference will now be made in detail to embodiments of the present invention, one or more examples of which are illustrated in the drawings. Each example is provided by way of explanation of the present invention, and not meant as a limitation of the present invention. For example, features illustrated or described as part of one embodiment of the present invention may be used with another embodiment of the present invention to yield still a third embodiment. It is intended that the present invention include these and other modifications and variations.

It is to be understood that the ranges and limits mentioned herein include all ranges located within, and also all values located under or above the prescribed limits. For instance, a range from about 100 to about 200 also includes ranges from 110 to 150, 170 to 190, and 153 to 162. Further, a limit of up to about 7 also includes a limit of up to about 5, up to 3, and up to about 4.5.

FIG. 1 depicts a foam layer fastening system 40 according to the present invention having a first engaging portion 42 comprising a foam layer 44 joined to a first member 46, shown attached to a second engaging portion 52 comprising a landing layer 54 joined to a second member 56. The foam layer 44 has an engaging surface 48 and a remote surface 50 joined to the first member 46. Likewise, the landing layer 54 has an engaging surface 58 and a remote surface 60. The foam layer 44 is depicted as a simple layer of foam material 64 alone, but could also comprise an integral reinforcing layer 66 (not shown) on the remote surface 50 of the foam material 64.

The first and second members 46 and 56, respectively, could be any two surfaces that are desirable to join by mechanical fasteners, and could comprise, for example, fabrics, films, composite articles, wood, glass, metal, medical devices, automotive components, nonwoven webs, paper, tissue, and the like.

Figure 2:
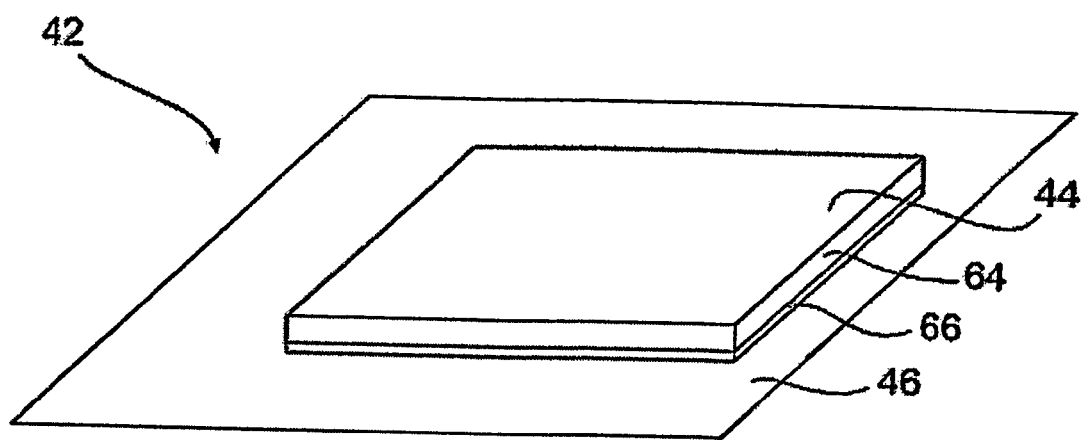
FIG. 2 depicts a perspective view of a foam layer fastening system according to the present invention.

FIG. 2 depicts another embodiment of the first engaging portion 42 of a foam layer fastening system 40 in which the foam material 64 of the foam layer 44 is joined to a reinforcing layer 66.

Figure 3:
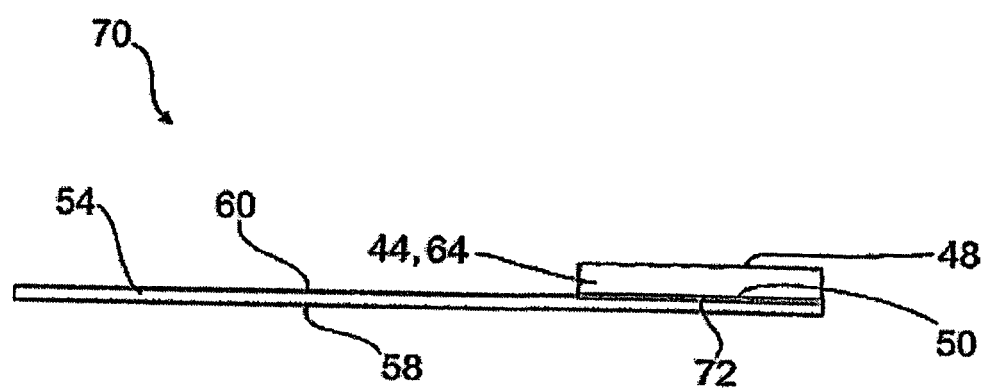
FIG. 3 depicts a self-adhesive strip of the present invention comprising a foam layer joined to a length of landing layer.

FIG. 3 depicts a self-adhesive strip 70 of the present invention comprising a foam layer 44 joined to a length of landing layer 54 by attachment means 72, which comprise adhesive, ultrasonic bonds, a thermal weld involving fused thermoplastic material, and so forth. The engaging surface 58 of the landing layer 54 is depicted as remote from the engaging surface 48 of the foam layer 44 (i.e., the two engaging surfaces 48 and 58 are on opposing sides of the self-adhesive strip 70), but the engaging surface 58 of the landing layer 54 may also be on the same side of the self-adhesive strip 70 as the foam layer 44, or both surfaces of the landing layer 54 may be adapted to engage with foam material 64 of the foam layer 44.

Such a self-adhesive strip 70 may serve as a stand-alone product, such as a tie for vegetables or other products or a wristband also comprising indicia or a label attached to the landing layer 54, or the self-adhesive strip 70 may be attached to articles such as umbrellas, absorbent articles, medical gowns, coats, garbage bags, and other items for which fastening means may be desirable.

Figure 4:
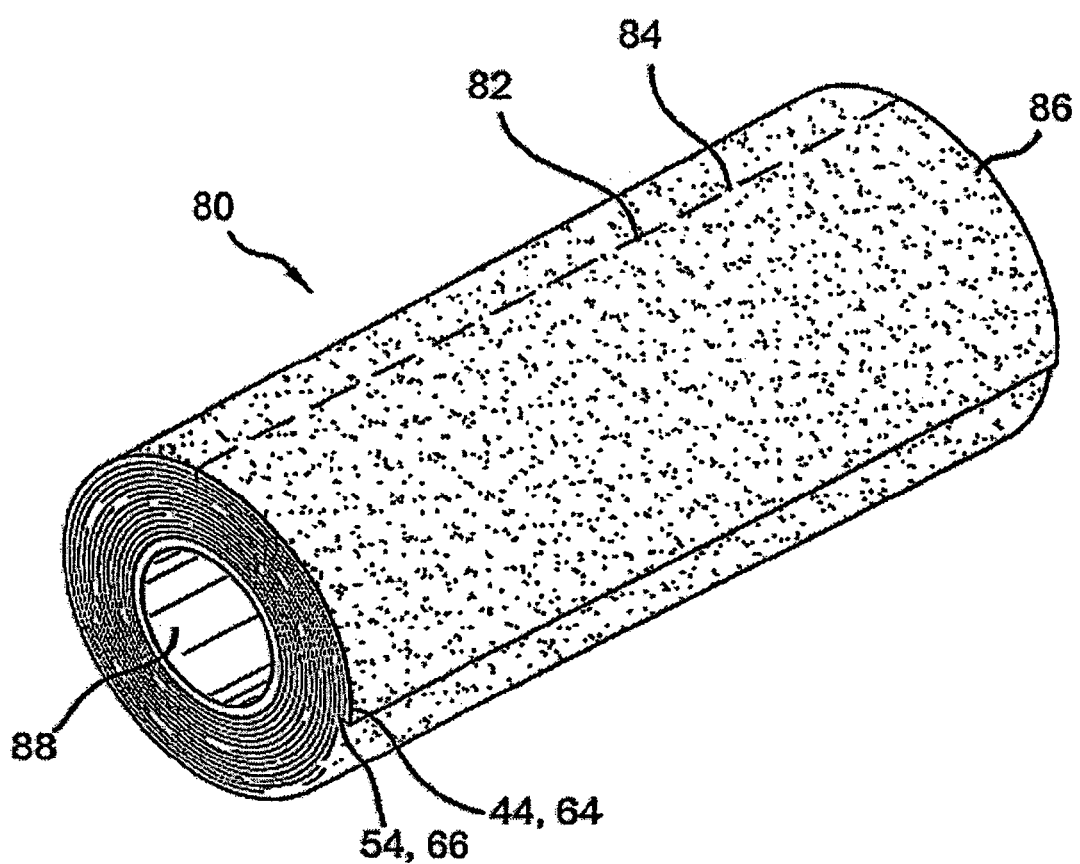
FIG. 4 depicts a roll of cleaning wipe articles having self-attaching properties.

FIG. 4 depicts a roll 80 of cleaning wipe articles 86 having self-attaching properties. The cleaning wipe articles 86 comprise a foam layer 44 joined to a landing layer 54, which also serves as a reinforcing layer 66 according to the principles of U.S. patent application Ser. No. 10/744,238, filed by Chen et al. on Dec. 22, 2003, previously incorporated by reference. In this embodiment of the present invention, the cleaning wipe articles 86 may be provided in a roll 80 without the roll 80 rapidly becoming unwound when removed from any packaging (not shown) because the upper foam layer 44 of each wipe may attach to the lower reinforcing layer 66 between adjacent layers in the roll 80. The same principle applies whether the foam layer 44 is outward or inward in the roll 80 (as depicted, the foam layer 44 is outward). Because neighboring layers in the roll 80 may adhere to one another, the roll 80 has high integrity and does not come unwound, but requires a degree of force to unpeel a cleaning wipe article 86 from the roll 80. Individual cleaning wipe articles 86 may be separated from the remainder of the roll 80 by virtue of perforations 82 between continuous portions 84 of the cleaning wipe articles 86. The roll 80 may be provided with a core 88 that optionally may be adapted for insertion onto spindles or into dispensers for paper towels or customized dispensers for foam-based wipes in roll form. As described in U.S. patent application Ser. No. 10/744,238 document, wipes comprising melamine foam material or other cleaning foam materials joined to a reinforcing layer 66 may be effective in cleaning a variety of surfaces, in part due to the abrasive nature of the cleaning foam material.

Figure 5:
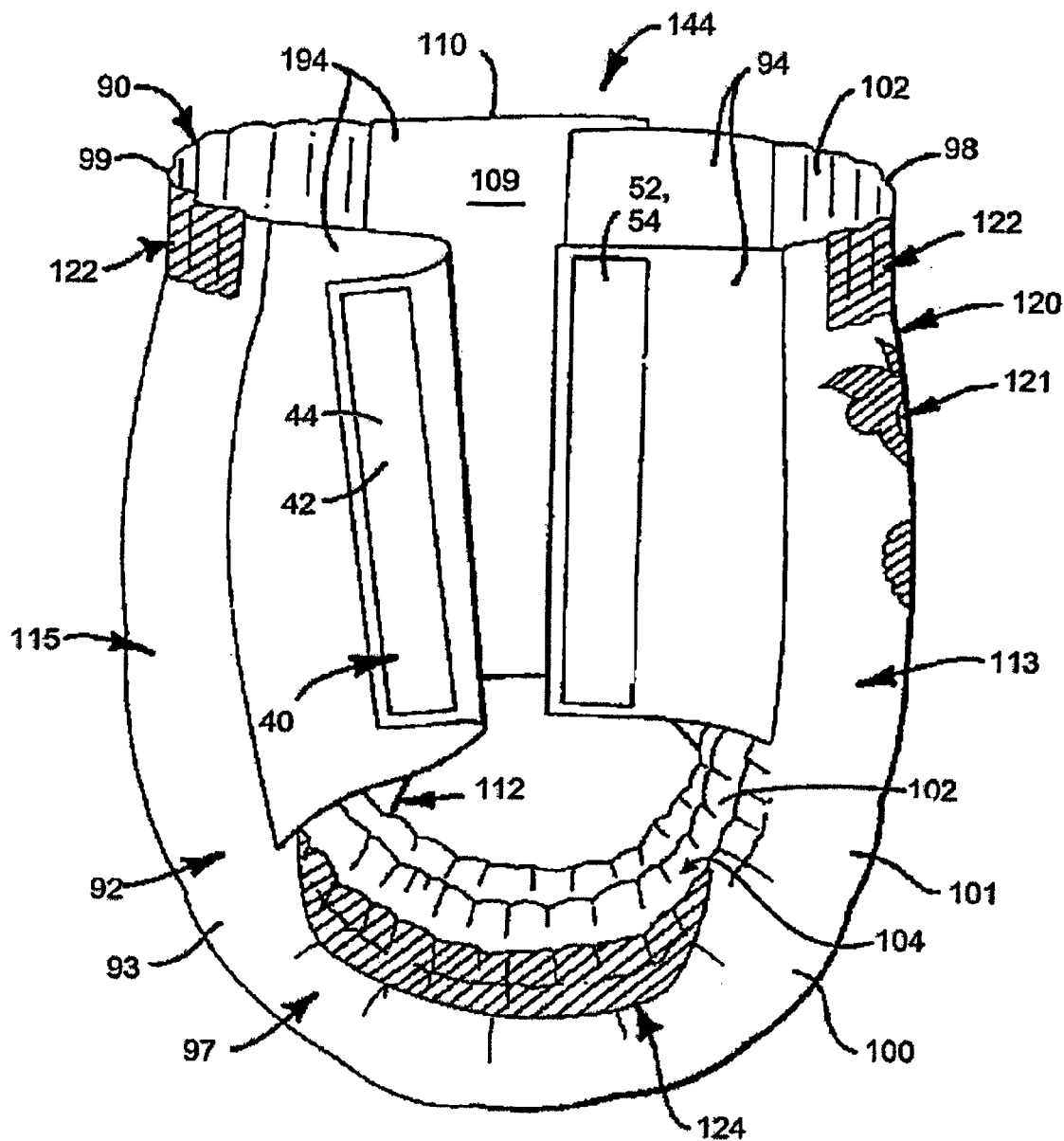
FIG. 5 depicts an absorbent article in a partially fastened state comprising a foam layer fastening system of the present invention.
Figure 6:
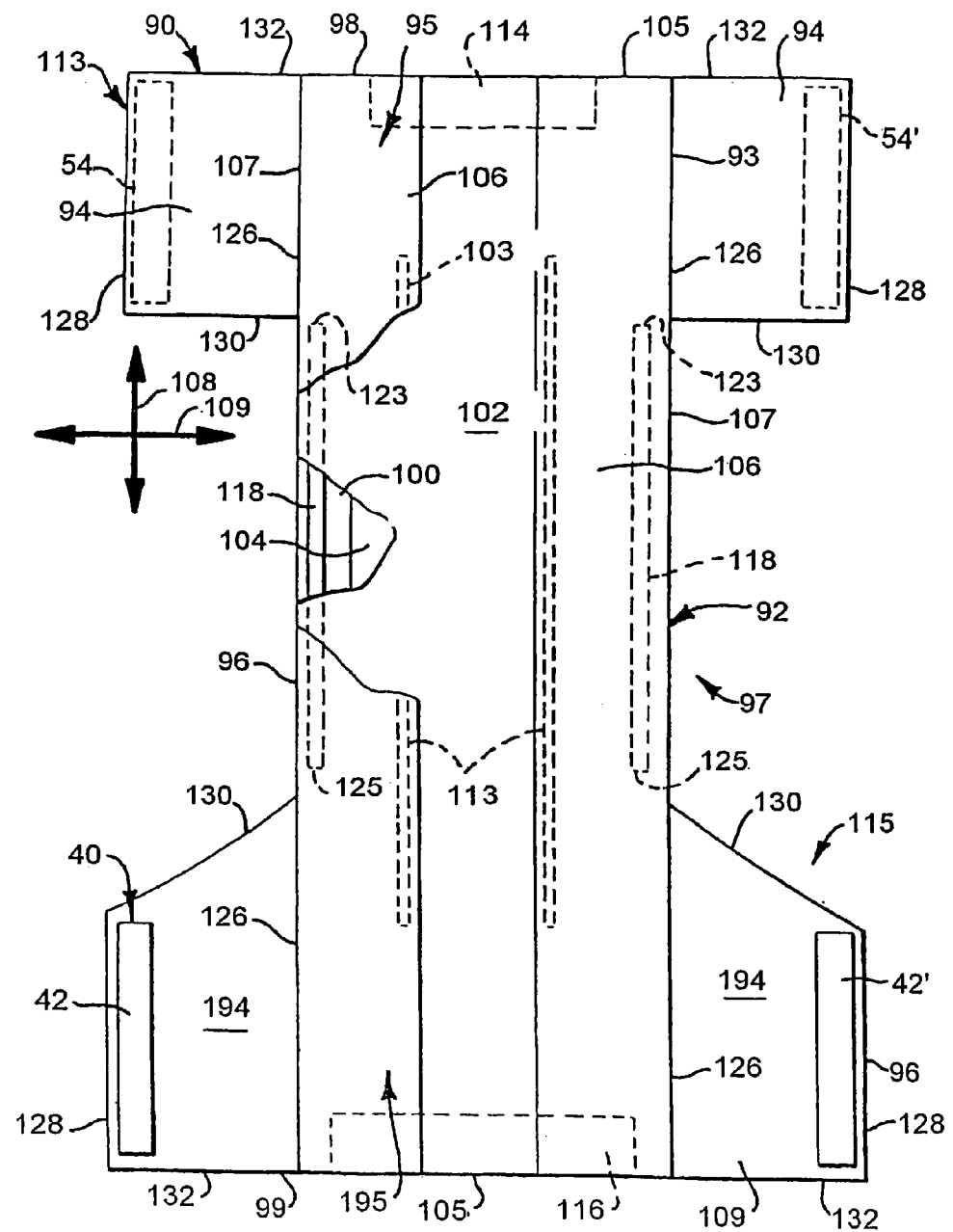
FIG. 6 depicts an unfastened absorbent article comprising a foam layer fastening system of the present invention.
Figure 7:
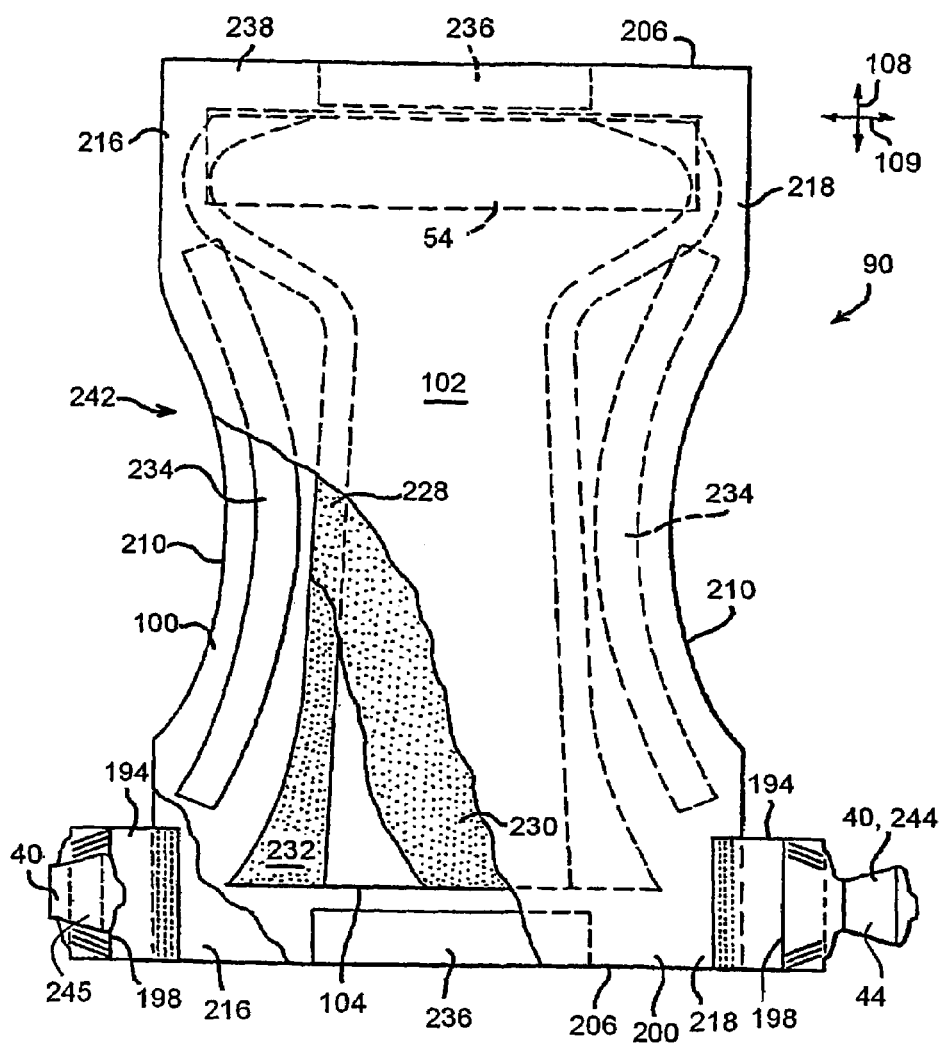
FIG. 7 depicts another disposable article comprising a foam layer fastening system.

In one embodiment of the present invention, the materials and methods may be employed to produce a plurality of selected panel-and-fastener components for various articles, as illustrated in FIGS. 5 to 7.

As shown in FIGS. 5 and 6, a disposable absorbent article 90, here depicted as a training pant, may comprise the foam layer fastening system 40 of the present invention. The absorbent article 90 is related to the training pant disclosed in U.S. Pat. No. 6,562,167, issued to Coenen et al. on May 13, 2003. It is illustrated in a partially fastened mode in FIG. 5 and in an unfastened mode in FIG. 6. The absorbent article 90 comprises an absorbent chassis 92 and a foam layer fastening system 40 having a foam layer 44 of the present invention. The absorbent chassis 92 defines a front waist region 113, a back waist region 115, a crotch region 117 interconnecting the front and back waist regions 113 and 115, respectively, an inner surface 109 which is configured to contact the wearer, and an outer surface 101 opposite the inner surface 109 which is configured to contact the wearer's clothing. The absorbent chassis 92 also defines a pair of transversely opposed side edges 96 and a pair of longitudinally opposed waist edges, which are designated front waist edge 98 and back waist edge 99. The front waist region 113 is contiguous with the front waist edge 98, and the back waist region 115 is contiguous with the back waist edge 99.

The illustrated absorbent chassis 92 comprises a composite structure 93 which can be rectangular or any other desired shape, a pair of transversely opposed front side panels 94, and a pair of transversely opposed back side panels 194. The composite structure 93 and front and back side panels 94 and 194, respectively, may comprise two or more separate elements, as shown in FIG. 5, or may be integrally formed. Integrally formed front and back side panels 94 and 194, respectively, and composite structure 93 would comprise at least some common materials, such as the bodyside liner, flap composite, outer cover, other materials and/or combinations thereof, and could define a one-piece elastic, stretchable, or nonstretchable absorbent article 90, which may further comprise segments of foam layers (not shown) disposed on the outer surface thereof.

The absorbent article 90 and in particular the outer cover 100 may comprise one or more appearance-related components such as printed graphics 121 on the front surface 120, a colored stretchable waist band 122, etc. Examples of appearance-related components include, but are not limited to:

graphics; highlighting or emphasizing leg and waist openings in order to make product shaping more evident or visible to the user (e.g., a printed leg opening region 124); highlighting or emphasizing areas of the absorbent article 90 to simulate functional components such as elastic leg bands, elastic waistbands, simulated "fly openings" for boys, ruffles for girls; highlighting areas of the absorbent article 90 to change the appearance of the size of the absorbent article 90; registering wetness indicators, temperature indicators, and the like in the absorbent article 90; registering a back label, or a front label, in the absorbent article 90; and, registering written instructions at a desired location in the absorbent article 90.

The illustrated absorbent article 90 includes a foam layer fastening system 40 for refastenably securing the training pant about the waist of the wearer. The illustrated fastening system 40 includes a first engaging portion 42 that is adapted to refastenably connect to a second engaging portion 52. When the first engaging portions 42 comprise a foam layer 44, as shown, the second fastening portion 52 may comprise a landing layer 54 joined to the front side panels 94 or may simply be the outer cover 100 itself or any existing functional component of the absorbent article 90, in which case the second fastening portion 52 may simply be regions of other materials onto which the first engaging portions 42 may be attached.

The first and second engaging portions 42 and 52, respectively, may be supplemented with conventional hook and loop materials, if desired. Suitable loop materials are available from Guilford Mills, Inc., located in Greensboro, N.C., under the trade designation No. 36549. Another suitable loop material may comprise a pattern un-bonded web as disclosed in U.S. Pat. No. 5,858,515, issued to Stokes et al. on Jan. 12, 1999. Suitable hook material may be molded or extruded of nylon, polypropylene or another suitable material. Suitable single-sided hook materials are available from commercial vendors such as Velcro Industries B.V., located in Amsterdam, Netherlands, or affiliates thereof, and are identified as Velcro HTH-829 with a uni-directional hook pattern and having a thickness of about 0.9 millimeters (35 mils) and HTH-851 with a unidirectional hook pattern and having a thickness of about 0.5 millimeters (20 mils); and Minnesota Mining & Manufacturing Co:, located in St. Paul, Minn., including specific materials identified as CS-600.

With particular reference to FIG. 6, the first engaging portions 42 and 42' are desirably although not necessarily disposed on the inner surface 109 of the absorbent article 90 in the back waist region 115. The first engaging portions 42 and 42' are desirably positioned along the distal edges 128 of the back side panels 194, and abutting or adjacent to the back waist edge 99. In certain embodiments of the present invention, for example, the first engaging portions 42 and 42' may be located within about 2 centimeters, and more particularly within about 1 centimeter, of the distal edges 128, the back waist edges 99, and the leg end edges 130.

FIG. 7 depicts another example of an absorbent article 90, in this case a disposable diaper comprising a foam layer fastening system 40. Apart from the new use of the foam layer fastening system 40, much of the design of the chassis and other components of the absorbent article 90 is disclosed in U.S. Pat. No. 5,399,219, issued to Roessler et al. on Mar. 21, 1995, the disclosure of which is incorporated by reference to the extent that it is non-contradictory herewith.

The absorbent article 90 comprises an absorbent core 104 disposed between the bodyside liner 102 and the outer cover 100. The absorbent article 90 has a longitudinally extending length dimension 108 and a laterally extending width dimension 108'. There is also an intermediate section 42 which interconnects the first waist region 238 and a second waist region 240.

The absorbent article 90 comprises a fastening means, such as a fastening assembly 244 that is connected to each of the stress beam sections 198 and is arranged to extend laterally from each of the back side panels 194 for securing the front and back waist regions 113 and 115 of the absorbent article 90 about a wearer during the use of the absorbent article 90. In various embodiments of the invention, the fastening assembly 244 may be located at either or both of lateral end regions 216 and 218 of either or both of the front and back waist regions 113 and 115, respectively. The representatively shown embodiment has the fastening assembly 244 located at the terminal side edges of the back waist region 115. The fastening assembly 244 may be bonded to the absorbent article 90 by any known means such as by ultrasonically welded bonds, thermal welds, adhesives, and the like, and one or more layers of additional material serving as tab substrates or bonding means, which may also enhance strength, stretching properties, or other features.

The fastening assembly 244 comprises a foam layer 44. The foam layer 44 may be provided to the user in a protected form, such as covered within a folded fastening assembly 245, such that upon unfolding the folded fastening assembly 245 is opened to expose the foam layer 44 for joining to the landing layer 54 (not shown) or other portions of the absorbent article 90 (e.g., other portions of the outer cover 100).

In various embodiments of the present invention, the fastening assembly 244 may be located at either or both of lateral end regions 216 and 218 of either or both of front and back waist regions 113 and 115, respectively. The representatively shown embodiment has the foam layer 44 located at the terminal side edges of back waist region 115.

A supplemental landing layer 246 provides a target zone for receiving an attachment of fastening assembly 244 thereon. In the illustrated embodiment of the present invention, landing layer 246 may be positioned on the outward surface of the outer cover 100 and may located on the front waist region 113 of the absorbent article 90. The landing layer 246 may constructed of a suitable material, such as polypropylene, polyester, or the like, and may configured and arranged to accept a secure attachment with the foam layers 44. In addition, the landing layer 246 and the foam layers 44 may be cooperatively constructed and arranged to provide a releasable adhesion which allows the fastening assemblies 244 to be removed from the landing layer 246 for repositioning and re-adhesion without tearing or excessively deforming the material of the outer cover 100. For example, a suitable tape landing zone construction is described in U.S. Pat. No. 4,753,649, issued to Pazdernik on Jun. 28, 1988, the disclosure of which is hereby incorporated by reference to the extent that it is non-contradictory herewith.

In particular aspects of the present invention, each of the back side panels 194 may be formed from a separate piece of material which is then suitably assembled and attached to the selected front and/or back waist regions 113 and 115 of the absorbent article 90. In the illustrated embodiments of the present invention, for example, back side panels 194 are attached to the back waist region 115 of the outer cover 100, and may be operably attached to either or both of the outer cover 100 and bodyside liner 102 components of the absorbent article 90. The back side panels 194 extend laterally to form a pair of opposed waist-flap sections of the absorbent article 90, and are attached with suitable connecting means, such as adhesive bonding, thermal bonding, ultrasonic bonding, clips, staples, sewing or the like, or may be attached with removable fastening means (not shown) such as gecko-like adhesive material.

Leg elastic members 234 are located in the lateral side margins 210 of the absorbent article 90 and are arranged to draw and hold the absorbent article 90 against the legs of the wearer. The leg elastic members 234 are secured to the absorbent article 90 in an elastically contractible condition so that in a normal under strain configuration, the leg elastic members 234 effectively contract against the absorbent article 90. The leg elastic members 234 may extend essentially along the complete length of the intermediate crotch region 242 of the absorbent article 90. Alternatively, the leg elastic members 234 may extend the entire length of the absorbent article 90, or any other length suitable providing the arrangement of elastically contractible lines desired for the particular absorbent article design.

A foam layer fastening system 40 may also be used in sanitary napkins, such as those disclosed in U.S. Pat. No. 5,681,303, issued to Mills et al. on Oct. 28, 1997, the disclosure of which is incorporated by reference to the extent it is non-contradictory herewith. Particular attention is called to FIGS. 2, 3, and 4 of U.S. Pat. No. 5,681,303 document, in which central pad adhesives or flap adhesives or both may be replaced with a foam layer 44 to provide improved attachment to undergarments. Protective release paper or film may also be provided, if desired, to protect the foam layer 44 when not in use. Release liners that also serve as an individual package for a sanitary napkin are described in U.S. Pat. No. 4,556,146, issued to Swanson, et al. on Dec. 3, 1985 and in World Patent Application Publication No. WO 91/18574, published by Byrd et al. on Dec. 12, 1991.

Another configuration of feminine care products which may benefit from the use of a foam-based fastening system is shown in U.S. Pat. No. 4,917,697, issued to Osborn, III et al. on Apr. 17, 1990. The adaptation of foam layer fastening systems 40 to such an absorbent article 90 is illustrated in FIG. 8.

Figure 8:
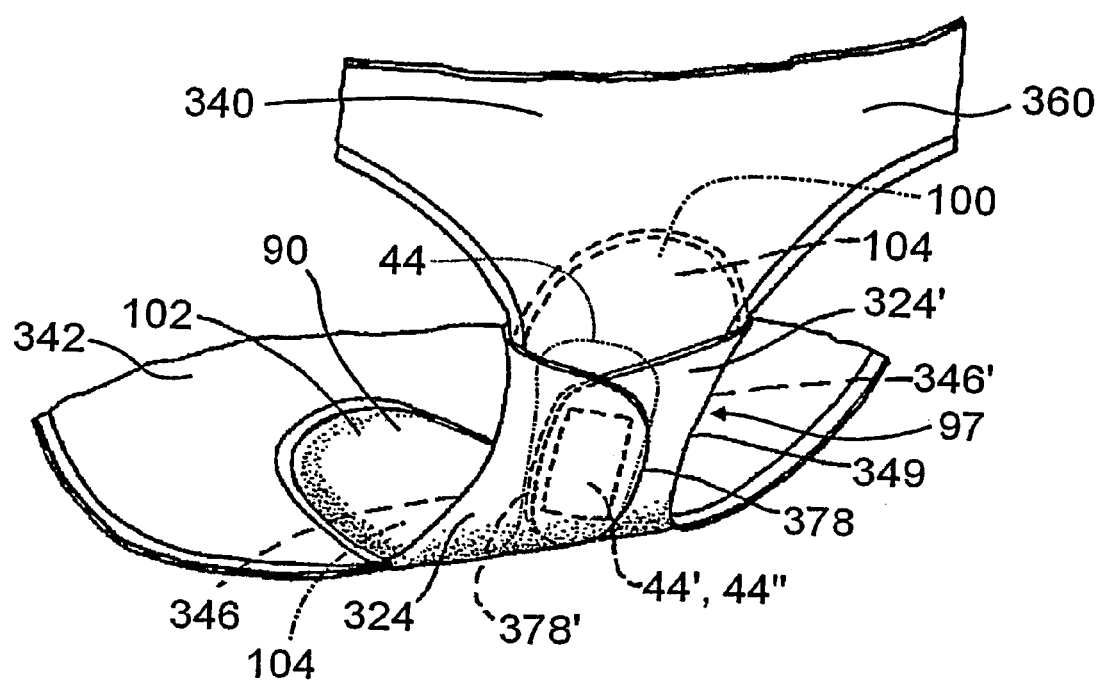
FIG. 8 depicts a feminine care article comprising a foam layer fastening system.

The absorbent article 90 (here a sanitary napkin) is utilized by removing any release liners (if present) and thereafter placing the absorbent article 90 in a panty 360 as shown in FIG. 8. The center of absorbent core 104, which lies between the outer cover 100 and the bodyside liner 102 of the absorbent article 90, is placed in crotch portion 117 of the panty 360 with one end of the absorbent core 104 extending towards the front section 340 of the panty 360 and the other end towards the back section 342 of the panty 360 and with the outer cover 100 in contact with the inner surface of center crotch portion 117 of the panty 360. A centrally positioned foam layer 44 maintains the absorbent core 104 in position. The distal portions of flaps 324 and 324' are folded around, respectively, side edges 346 and 346'. Patches of foam layers 44' and 44" serve as flap fasteners to secure flaps 324 and 324' in such position. Thus, flaps 324 and 324' are each folded over themselves with a portion of the panty 360, including side edges 346 and 346', interposed therebetween. The flaps 324 and 324' are folded over a fold line 349 defined by the edge of the panty 360 in the crotch region 117. As shown, the foam layer 44 is disposed between the outer cover 100 of the absorbent article 90 beneath the absorbent core 104 and the bodyside surface of the panty 360, while the patches of foam layer 44' and 44" on the flaps 324 and 324' are the garment side of the panty 360, with one patch of foam layer 44' being against the panty 360 itself, joining it to a flap 324', and the other patch of foam layer 44" joining one flap 324 to the other flap 324'. The foam layers 44' and 44" may extend up to or near the distal edges 378 and 378' of the flaps 324 and 324', if desired.

Numerous other sanitary napkin embodiments having flaps are available and are disclosed in the literature. For example, sanitary napkins having flaps are disclosed in U.S. Pat. No. 4,687,478, issued to van Tilburg on Aug. 18, 1987; U.S. Pat. No. 4,608,047, issued to Mattingly on Aug. 26, 1986; U.S. Pat. No. 4,589,876, issued to Van Tilburg on May 20, 1986; U.S. Pat. No. 4,285,343, issued to McNair on Aug. 25, 1981; U.S. Pat. No. 3,397,697, issued to Rickard on Aug. 20, 1968; and, U.S. Pat. No. 2,787,241, issued to Clark on Apr. 2, 1957.

Foam layer attachment means, adhesive materials, or any attachment means suitable for fastening to the textile materials of an undergarment or attaching to another suitable surface may also be used to attach flapless absorbent articles such as sanitary napkins and pantiliners to the undergarments. In such cases, pressure-sensitive adhesives or non-skid material usually applied to a side of the absorbent article may be replaced or supplemented with a foam layer 44. Examples of flapless sanitary napkins and pantiliners are presented in U.S. Pat. No. 4,834,739, issued to Linker, III et al. on May 30, 1989; and, U.S. Pat. No. 5,011,480, issued to Gossens et al. on Apr. 30, 1991.

Figure 28:
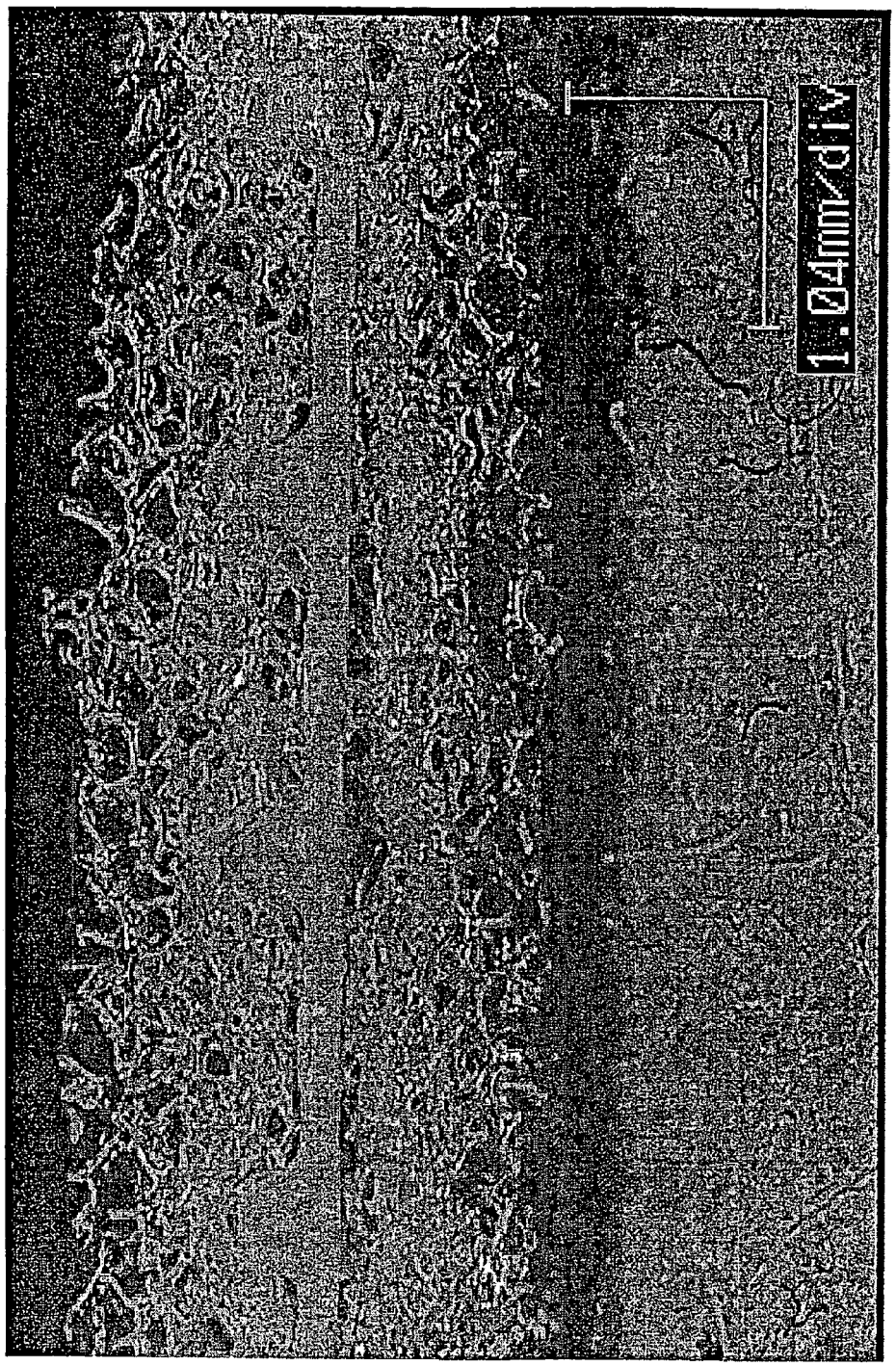
FIG. 28 is a photograph of a cross-section of a foam material comprising an internal scrim layer.

The foam layer 44 may also be reinforced by incorporating or attaching a high tensile strength material 68, e.g. scrim (see FIG. 28). This may be accomplished by any means know in the art, but more particularly by adhesive lamination of a high tensile strength material 68 to a foam material 64 or by formation of the foam material 64 about a high tensile strength material 68. In some embodiments of the present invention, the foam material 64 may be formed by dipping the high tensile strength material 68 into a liquid which is curable to form the foam material 64, and then subjecting the foam material 64 into which the high tensile strength material 68 has been incorporated to a curing process. One example of such a process is discussed in U.S. Pat. No. 6,613,113, issued to Minick et al. on Sep. 2, 2003.

An example of the high tensile strength material 68 is a scrim material comprising a set of parallel or substantially parallel threads in one direction, which are interlaced and/or bonded with another set of parallel or substantially parallel threads in a different direction. The diameter of the threads comprising scrim material may be from about 0.1 mm to about 1.0 mm. The threads of the scrim material may be spaced at intervals of about 2 mm to about 10 mm. The scrim material may be made of a polyolefin selected from the group consisting of polyethylene, polypropylene, copolymers polyethylene, copolymers of polypropylene, polyesters, Nylon 6, Nylon 66, and mixtures thereof. Scrim materials are available from various commercial sources. An example of a scrim material that may be used with the present invention is commercially available under the trade designation of Vexor® from Conwed Plastics, located in Minneapolis, Minn.

In another embodiment of the present invention, an elastomeric high tensile strength material 68, such as a scrim material, may be used to reinforce the foam material 64. An example of an elastomeric high tensile strength material 68 is an elastomeric scrim having a set of parallel or substantially parallel threads of elastic material in one direction, interlaced and/or bonded with another set of parallel or substantially parallel threads of elastic or non-elastic materials in a different direction. The diameter of the threads comprising scrim material may be from about 0.1 mm to about 1.0 mm. The threads of the scrim material may be spaced at intervals of about 2 mm to about 10 mm. The elastomeric materials suitable for use in the high tensile strength material 68 may be independently selected from the following group of materials consisting essentially of: natural or synthetic rubber; styrene block copolymers; ethylvinynacetate (EVA); Lycra®; KRA- TON®; polyethylene (PE) including metallocene catalyst polyethylene; any other material which is capable of elongation and recovery; and, mixtures or combinations thereof. An example of an elastic scrim material that may be used with the present invention is commercially available under the trade designation of X50020 from Conwed Plastics.

Incorporation in or attachment of an elastomeric high tensile strength material 68 to the foam material 64 may not only improve tensile strength of the foam material 64, but also provide or increase the stretch properties of the foam material 64, i.e. elongation and recovery characteristics. Such properties in the foam material 64 may be applied to a number of product applications as discussed above.

Cleaning Articles

The adhesive materials of the present invention may also be used to improve the attachment of other disposable articles such as cleaning sheets for dusting devices, dry mops, and wet mops, including the SWIFFER® brand of cleaning articles of Procter and Gamble (Cincinnati, Ohio) such as SWIFFER® WetJet™ and related floor cleaning articles. Gecko-like materials may also be effective in attaching sponges, mop heads, and cleaning cloths to re-usable heads and handles.

Exemplary disposable cleaning sheets that may be combined with gecko-like adhesive materials are disclosed in U.S. Pat. No. 6,561,354, issued to Fereshtehkhou et al. on May 13, 2003; World Patent Application Publication No. WO 01/41622, published by Wong et al. on Jun. 14, 2001; World Patent Application Publication No. WO 03/00104, published by Kacher et al. on Jan. 3, 2003; World Patent Application Publication No. WO 98/52458, published by Fereshtehkhou et al. on Nov. 26, 1998; and, European Patent Application No. 923902-A2, published by Abe et al. on Jun. 23, 1999.

Figure 9A:
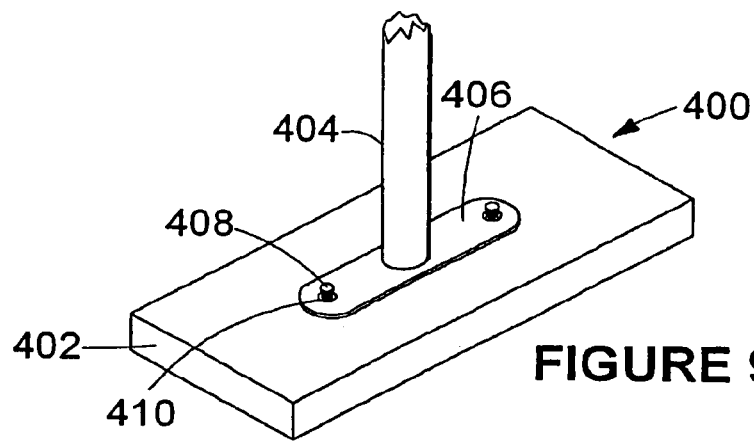
FIGS. 9A-9C depict a mop system with a mop head cover substrate which may be joined to a mop head using a foam fastening system.
Figure 9B:
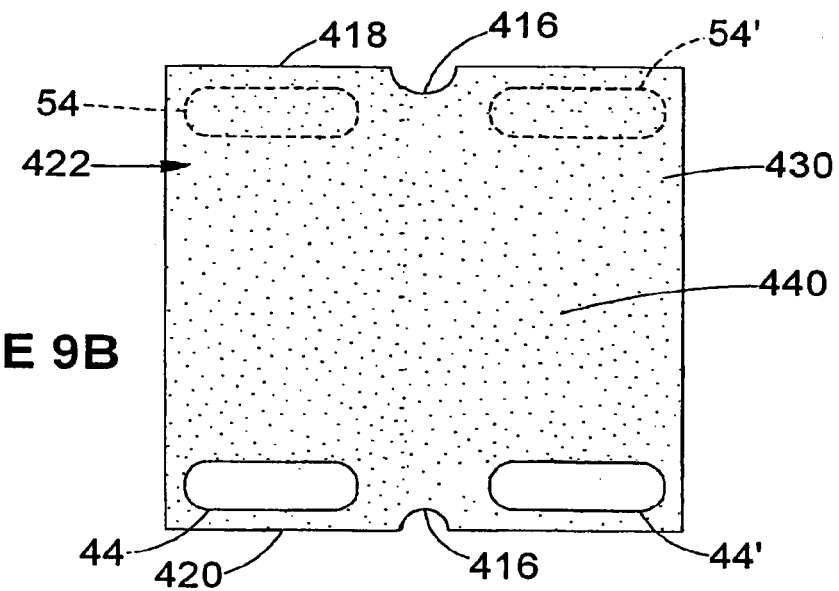
Figure 9C:
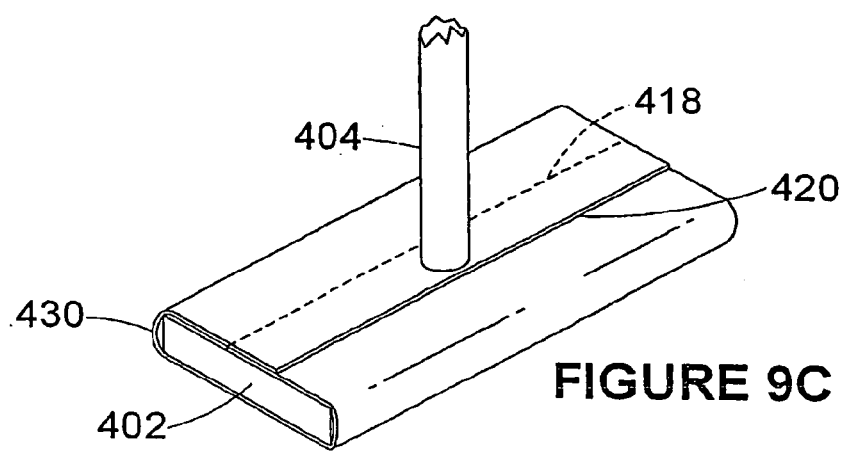

One example of a cleaning article according the present invention is shown in FIGS. 9A-9C. Here a mop 400 includes a disposable mop head cover substrate 430 which fits the mop head 402. The mop head cover substrate 430 has a first edge 418, a second edge 420, and an outward face 422. The mop head cover substrate 430 may comprise loops suitable for fastening with the foam layers 44 and 44' or may be provided with patches of a landing layer 54 and 54' having loops suitable for attachment to the foam layers 44 and 44'. The mop head cover substrate 430 may be made of a material or materials (ideally biodegradable), suitable for performing a waste contamination removal function, and are described below and previously herein.

As shown in FIG. 9C, the mop head cover substrate 430 wraps around the mop head 402 with the first edge 418 overlapping the second edge 420 and is held in place by the attachment with a foam layer 44, located near the first edge 418 on the opposite face of the mop head cover substrate 430 from the outward face 422, and which may join to patches of a landing layer 54, located near the second edge 420 on the outward face 422. The landing material may, if desired, be identical to the mop head cover substrate 430 (i.e., simply a part of the mop head cover substrate 430 with no additional material added) or may comprise an additional layer of material secured to the mop head cover substrate 430. Handle orifices 416 facilitate good fit around the handle 404 which is secured to the mop head 402 by a mounting plate 406 that is attached to the mop head 402 by screws, rivets, or other joining means 408. A waste contamination sensor 440, as described in U.S. Pat. No. 6,501,002, issued to Roe et al. on Dec. 31, 2002, may be incorporated into or onto at least part of outward face 422 of the mop head cover substrate 430.

Alternatively, the mop head 402 may comprise patches of a foam layer 44 (not shown) on the upper surface or other surfaces thereof, such that the mop head cover substrate 430 may be directly attached to the mop head 402 by pressing the mop head cover substrate 430 or landing layers 54 and 54' thereon against the foam layer 44 on the mop head 402.

Figure 10A:
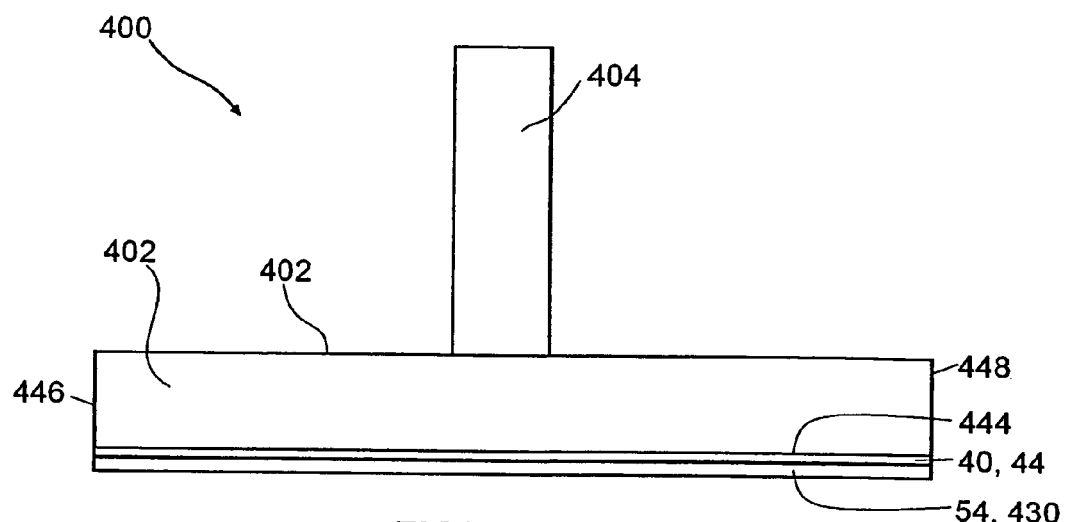
FIGS. 10A and 10B depict another embodiment of a mop system comprising foam layer fastening system.
Figure 10B:
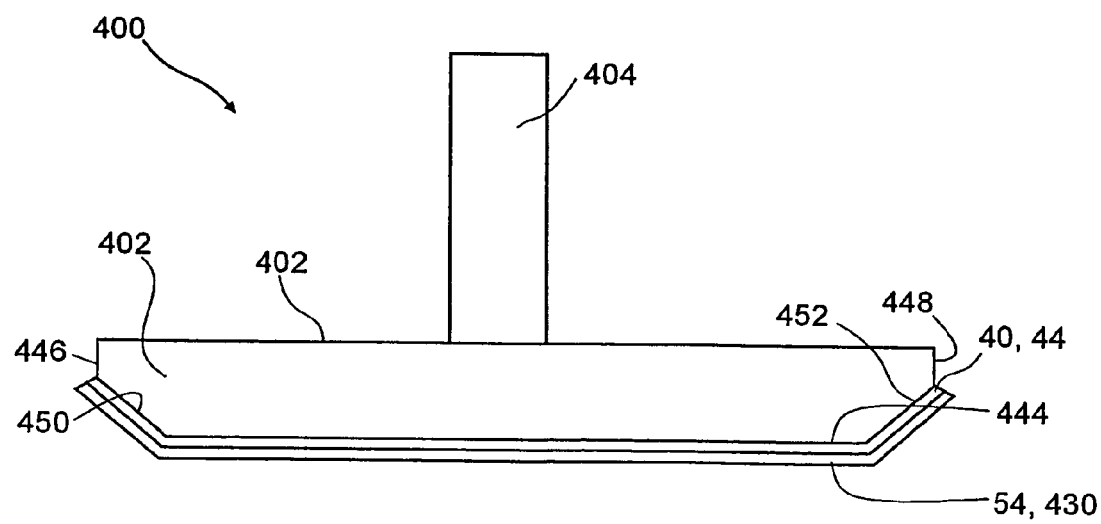

FIGS. 10A and 10B depict another example of a mop 400 similar to that of FIG. 9, but in which the disposable mop head cover substrate 430 is joined to the mop head 402 by a foam layer fastening system 40 comprising a foam layer 44 adapted for engaging a landing layer 54 on the mop head cover substrate 430, which may comprise the same material as the mop head cover substrate 430. In this manner, the mop head cover substrate 430 no longer needs to wrap a major portion of the mop head 402, and in particular does not need to wrap the upper side 442 of the mop head 402 in order to be secured, for it may be secured directly to the lower side 444 of the mop head 402. In FIG. 10A, the mop head cover substrate 430 is substantially coextensive with the lower side 444 of the mop head 402, with no material wrapping the front or rear edges 446 and 448, respectively, or the upper side 442 of the mop head 402. The strong but removable attachment means provided by the foam layer fastening system 40 allows the mop head cover substrate 430 to be used in wiping or mopping operations.

In FIG. 10B, the mop head 402 is provided with a beveled front region 450 and beveled rear region 452 onto which the mop head cover substrate 430 is secured by means of the foam layer fastening system 40. In this example, a portion of the front edge 446 and the back edge 448 of the mop head 402 is wrapped by the mop head cover substrate 430, but there is no need for the material to wrap across the upper side 442 of the mop head 402, where the material would be wasted in terms of cleaning functionality. Thus, the system of FIGS. 10A and 10B provides for improved efficiency of the cleaning material used in the mop head cover substrate 430.

Cleaning products such as cleaning wipes, sponge-like products with covers, disposable scrub pads, disposable dish wipes, and the like may also benefit from the fastening abilities of the present invention, wherein the foam layer fastening system is used to secure one portion of the cleaning product to another portion, such as securing a cleaning pad to a handle or securing a wiping element onto or around an absorbent element. In one embodiment of the present invention, the cleaning product comprises a cleaning wipe article that may be attached to a foam layer, wherein the foam layer provides an additional benefit in addition to helping secure the cleaning wipe article. The additional benefit may be, for example, providing a sponge-like interior portion of a cleaning wipe article for good conformance of the cleaning wipe article to a surface, providing a grip for improved comfort, generating suds, holding liquid, and the like. In some embodiments of the present invention, the foam layer may optionally be used for scrubbing to provide abrasive cleaning when needed, particularly when melamine foam materials and the like are used. For example, a portion of a foam layer may be exposed or exposable to allow the foam material to be used to remove scuff marks on floors, mildew on walls or shower surfaces, grease or wax or crayon from hard surfaces, and the like. Thus, a cleaning product may comprise a wiping fabric secured to or around an underling substrate by a foam layer fastening system, wherein a portion of the foam layer fastening system may also be employed to clean a surface.

Figure 11A:
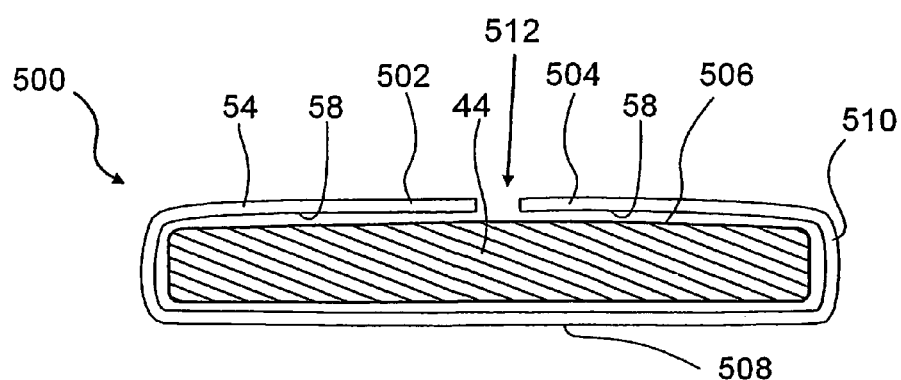
FIGS. 11A and 11B depict side views of a composite cleaning wipe according to the present invention.
Figure 11B:
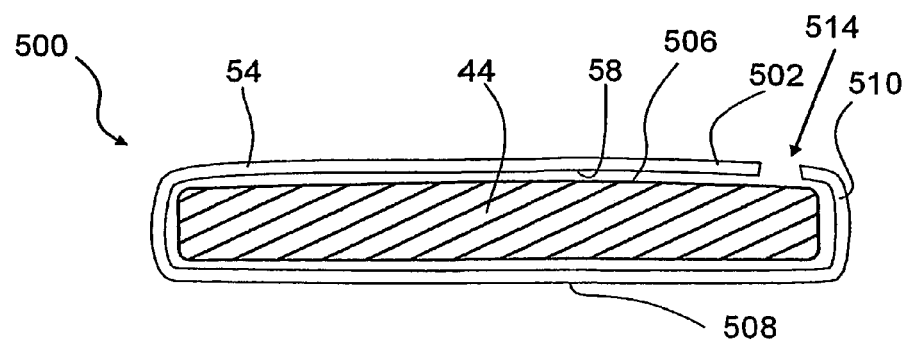

By way of example, FIGS. 11A and 11B schematically depict a cleaning wipe article 500 in cross-sectional view. The cleaning wipe article 500 comprises an internal foam layer 44 encased at least in part by an outer wrap 510 which provides a wiping surface 508. The outer wrap 510 may consist of or comprise a material that serves as a landing layer 54 with a foam-contacting surface 516 that may attach to the foam layer 44. In one embodiment of the present invention, the outer wrap 510 may be secured to the foam layer 44 primarily or solely by engagement of free-standing struts in the foam layer 44 with the outer wrap 510 (i.e., with loops in the foam-contacting surface of the outer wrap 510). In another embodiment of the present invention (not shown), adhesives or other attachment means may supplement the mechanical attachment of the foam layer 44 to the outer wrap 510.

In the embodiment of the present invention shown in FIG. 11A, the two ends of the outer wrap 510 approach each other (or, alternatively, overlap) in a mid-portion 512 of the cleaning wipe article 500, such that the ends of the outer wrap 510 form a first openable portion 502 and a second openable portion 504 of the outer wrap 510, which may be peeled back by a user to reveal the scrubbing surface 506 of the foam layer 44 within the cleaning wipe article 500. Exposing the scrubbing surface 506 of the foam layer 44 may be useful when the user wishes to apply the foam layer 44 for more abrasive cleaning, such as removing a scuff mark from a floor or stain on a wall. For such purposes, the outer wrap 510 may be held in place on one side of the foam layer 44 while the exposed scrubbing surface 506 of the foam layer 44 is used for cleaning. Alternatively, the entire outer wrap 510 may be removed to allow the foam layer 44 to be used alone or with other materials for cleaning. In yet another embodiment of the present invention, the outer wrap 510 may function as a wiping surface 508 and may be removed when soiled and replaced with a fresh outer wrap 510 to permit further cleaning to take place.

In the embodiment of the present invention shown in FIG. 11B, the two ends of the outer wrap 510 approach each other (or, alternatively, overlap) in a end-portion 514 of the cleaning wipe article 500. The portion of the outer wrap 510 over the upper surface of the foam layer 44 forms a first openable portion 502 that may be peeled back to expose the scrubbing surface 506 of the internal foam layer 44 for more abrasive cleaning or for removal and optional replacement of the outer wrap 510.

Many other embodiments of the present invention may also be considered. For example, the free-standing struts of the foam layer may be treated to have increased roughness to provide better attachment to a landing layer, such as a loop layer (e.g., higher peel strength). The free-standing struts may be roughened by attaching particles to them, such as microspheres, mineral filler, etc., wherein attachment may be by thermal bonds, adhesive bonds, electrostatic attraction, entanglement, crystal growth by chemical vapor deposition, and so forth. Alternatively, the free-standing struts may be etched or otherwise treated (chemical attack, laser ablation, electron beam treatment, etc.) to remove portions of the surface material in individual free-standing struts thereof to increase texture. Examples of textured elements that may correspond to modified free-standing struts in the present invention are disclosed in U.S. Pat. No. 3,922,455, issued to Brumlik et al. on Nov. 25, 1975.

EXAMPLE 1

Two foam material samples were tested for fastening ability with a variety of nonwoven webs produced by Guilford Technical Textiles, located in Pine Grove, Pa., a division of Guilford Mills, Inc. located in Greensboro, N.C. The foam material samples were a thin layer (about 4 mm thickness) of BASOTECT® foam material sliced from a sample of a MR. CLEAN® Magic Eraser commercially available from Procter & Gamble, located in Cincinnati, Ohio and a block of open-cell polyurethane foam material, commercially available under the trade designation of FOAMEX® SIF 60Z from Foamex, Inc., located in Linwood, Pa., having dimensions of 6 inches by 6 inches by 0.5 inches, and a dry mass of 8.76 grams. Most of the foam material samples tested did not provide significant adhesion when contacted with the BASOTECT® foam material, presumably because the loops of the nonwoven webs were not of a suitable scale for best compatibility with the foam material samples, but several of the nonwoven webs adhered well to the polyurethane foam material.

In Table 1 below, the sample numbers of various Guilford nonwoven webs are listed, followed by a rating for adhesion to the polyurethane foam material sample. A rating of "A" is best, and "D" is worst was assigned to each of the samples of the Guilford nonwoven webs. The rating is based on a simple test in which each Guilford nonwoven web was lightly pressed against a portion of the foam material square and then tested to see if the foam material block would remain attached to the Guilford nonwoven web when oriented vertically. The smaller the overlap region required, the better the rating. In conducting the test, each nonwoven web sample, having dimensions of about 6.5 inches by 9.5 inches, was oriented vertically with the longer dimension corresponding to the vertical axis, and with a cardboard backing behind the nonwoven web sample. The foam material square was oriented with a corner up, in a diamond shape, and the uppermost corner was pressed lightly by human fingers against the lower edge of the nonwoven web sample, with a total force estimated at about 0.3 pounds of force. When the foam material square could remain attached to the nonwoven web sample (i.e., the bond between the foam material square and the nonwoven sample could sustain the mass of the foam material square) and the distance from the top corner of the foam material square to the bottom edge of the nonwoven web sample was only about 0.5 inches or less, the attachment was given an "A" rating to indicate good attachment. For nonwoven web samples that received an "A" rating, the foam material square typically could be joined to the nonwoven web sample simply by placing the nonwoven web sample in contact with the foam material square. In such cases also, if the foam material square were oriented with an edge parallel to the horizon and touched against the nonwoven web sample, it could typically remain suspended with a horizontal contact region spanning the width of the foam material square having a vertical length of only about one-quarter of an inch or less. A "B" rating was given when the foam material square would not remain attached under the conditions for the "A" rating, but could remain attached if the distance from the top corner of the foam material square to the bottom edge of the nonwoven web sample was increased to be about 1 inch. A "C" rating indicates that significantly more contact area was needed than for the "B" rating, but that the foam material square could remain vertically attached to the nonwoven web sample. In stating that the foam material square remained vertically attached to the nonwoven web sample, this means that it did not fall from the nonwoven web sample during a 5 second interval. A "D" rating indicated that the foam material square would not remain attached to the nonwoven web sample.

TABLE 1

Foam Material Attachment Ratings for Various Guilford Webs

| Guilford Web | Attachment Rating |
|---|---|
| One Touch ™ Light Duty Firm Finish Polyester Loop, Style 42873, 1.5 osy, 100% polyester | B |
| Flexible Nylon Loop, Style 43639, 1.5 osy, 100% nylon | A |
| Light Duty Coated Polyester Loop, Style 33562, 100% polyester | C |
| Flexible Nylon Loop, Style 43639 | A |
| Light Duty Uncoated Polyester Loop, Style 43148 | B |
| Light Duty Coated Polyester Loop, Style 19903 | C, D (two different samples) |
| Light Duty Uncoated Polyester, Style 34922 | B |
| Light Duty Acrylic Coated Polyester Loop, Style 36133 | B |
| One Touch ™ Light Duty Uncoated Polyester Loop, Style 42145 | A |
| One Touch ™ Light Duty Firm Finish Polyester Loop, Style 42873 | C |
| One Touch ™ Light Weight Uncoated Polyester Loop, Style 42930 | C |
| Firm Finish Polyester Loop, Style 42931 | D |
| Precision Loop Light Weight Firm Finish Polyester Loop, Style 42931 | D |
| General Duty Uncoated Polyester Loop, Style 39020 | D |
| General Duty Uncoated Polyester Loop, Style 36192 | D |
| General Duty Light Coated Polyester Loop, Style 36816 | D |
| One Touch ™ Light Weight Firm Finish Polyester Loop, Style 42931 | D |

EXAMPLE 2

A spunlace web, having a trade designation of Code CLC-424, was obtained from Polymer Group, Inc. (headquartered in North Charleston, S.C.). Though attachment of this spunlace web to the melamine foam material was relatively weak, good attachment occurred with a FOAMEX® Z60B polymeric foam material having a thickness of about 0.13 inches and a pore size of 60 cells per inch. The foam material had an identification number of 75131.

Figure 12:
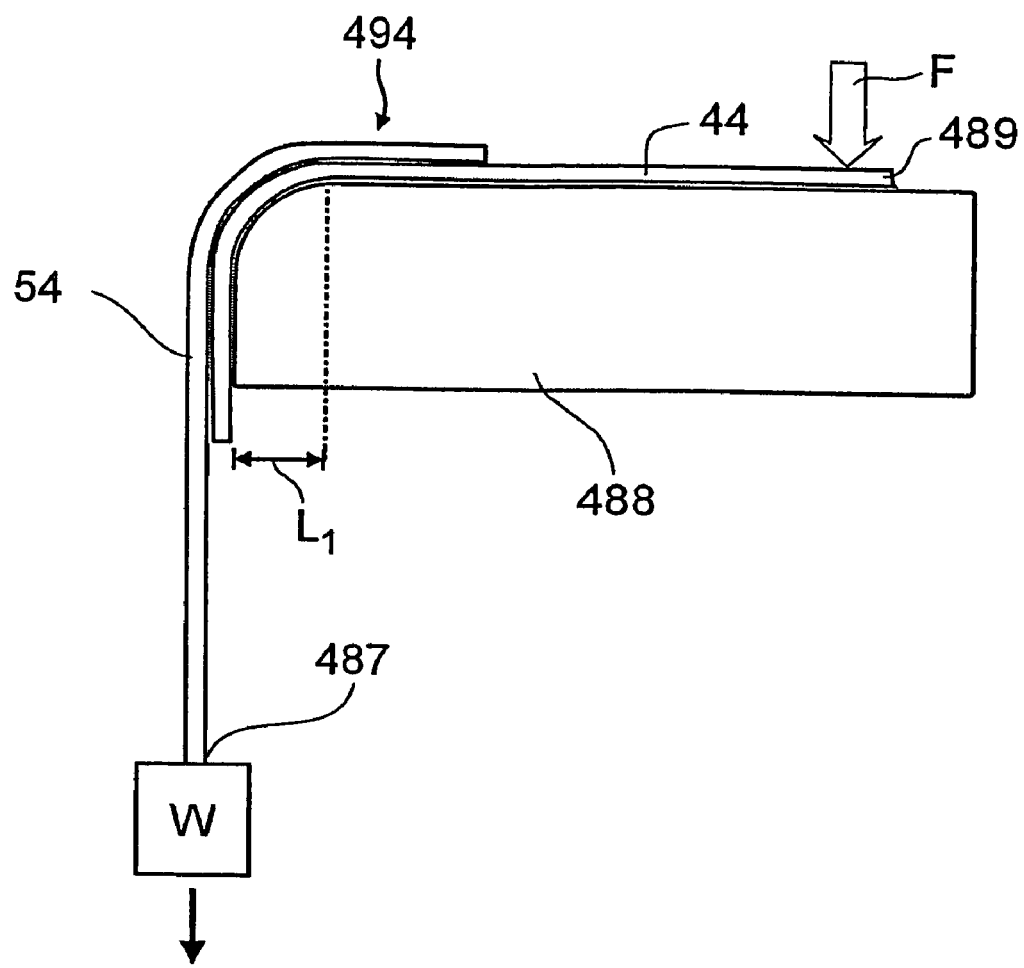
FIG. 12 depicts a test apparatus for measuring attachment strength of a foam layer to an engaging surface.

FIG. 12 depicts apparatus for a simple test carried out as a measure of the attachment strength in this example. A 6-inch square section of the foam layer 44 was lightly pressed against the seven-inch wide length of the spunlace web (acting as the landing layer 54) to establish a three-inch long overlap region 494 covering about 50% of the surface of one side of the foam layer 44. The attached foam layer 44 and partially overlapping landing layer 54 were draped with the foam layer 44 down over the edge of a wooden table 488 about 1.25 inches thick with a beveled edge approximating a quarter section of a circle. The distance $L_1$ in FIG. 12, corresponds to the distance from the edge of the wooden table 488 to the beginning of the bevel on the top surface, is about 0.3 inches, which approximates the radius of curvature of the bevel. With a first end 489 of the foam layer 44 restrained by a downward force F, a weight W was applied across the second end 487 of the foam layer 44 by attaching clips to the second end 487 which in turn held a weight. When the mass of the weight W was about 1600 grams, the foam layer 44 had stretched but the attachment remained secure. As the mass of the weight W was increased to about 1900 grams, the attachment between the foam layer 44 and the landing layer 54 began to slowly give way. The strength of the attachment for this test may be estimated at about 1900 grams of force over the attachment area. As used herein, this test method will be called the Table Edge Test, and the attachment strength according to the Table Edge Test may be said to be about 1900 grams of force for the sample tested.

EXAMPLE 3

A spunlace web, having a trade designation of Code DE-135 obtained from Polymer Group, Inc., had a basis weight of 2.17 osy, a Matese (diamond-like) hydroentangled pattern, and a composition of 30% PET, 35% lyocel, and 35% rayon. Two versions were obtained of the spunlace web, one in which the pattern was distinct and sharp, with relatively little fuzziness (Sample A), and one which was fuzzy and in which the hydroentangled patterns was less clear (Sample B). The two versions of the spunlace web having the same code apparently experienced different degrees of hydroentangling. It is believed that less intense hydroentangling was applied to the spunlace web sample with the less defined pattern. For Sample A of the spunlace web, attachment was relatively poor to both melamine foam material and the polyurethane foam material, but excellent attachment was possible for Sample B of the spunlace web, particularly against the melamine foam material.

EXAMPLE 4

A coarse polyurethane foam material, under the trade designation of FOAMEX® Z60B polymeric foam material, was found to provide intermediate attachment to a layer of colored felt material acting as a landing layer. When the foam material and the felt material was pressed together and subjected to in-plane shear on a flat surface (no curvature), the strength was substantial less than seen in several other combinations of foam materials and landing layers (although the Table Edge Test attachment strength was about 1000 grams of force). However, when the foam material is placed between two layers of the felt material, the attachment strength against in-plane shear on a flat surface was excellent. It is believed that a reinforcing layer or second landing layer sandwiching a foam layer as it is joined to a first landing layer may greatly improve the strength of the attachment. Even when the second layer is not a landing layer, its presence may reduce buckling and peeling of the foam layer from the first landing layer. By helping to maintain contact of the foam layer to the landing layer, premature release is prevented and the overall resistance of the system to in-plane shear is greatly increased. In some cases, without the top layer, deformation of a stretchable foam layer, especially thin foam layers, may cause warping or buckling of the foam layer, allowing detachment to occur due to the mechanical instability. A protective layer on top of the foam layer may be helpful.

Likewise, when a landing layer 54 is sandwiched between two foam layers 44 and 44', better attachment may be expected.

Figure 13A:
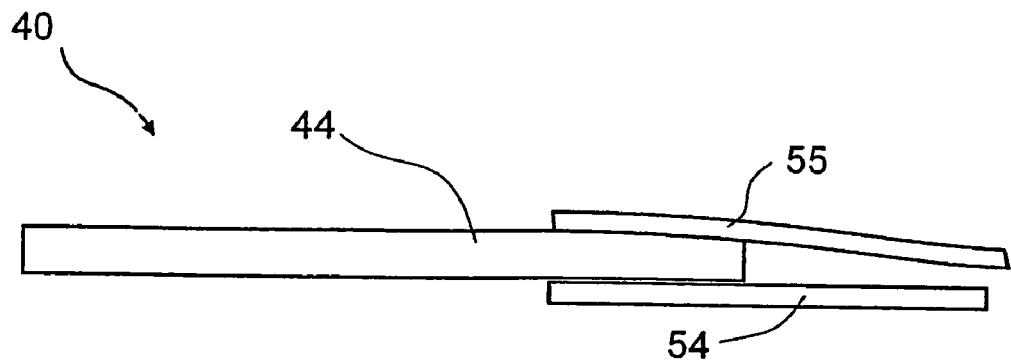
FIGS. 13A-13C depict additional embodiments of a foam-fastening system using a sandwich structure.
Figure 13B:
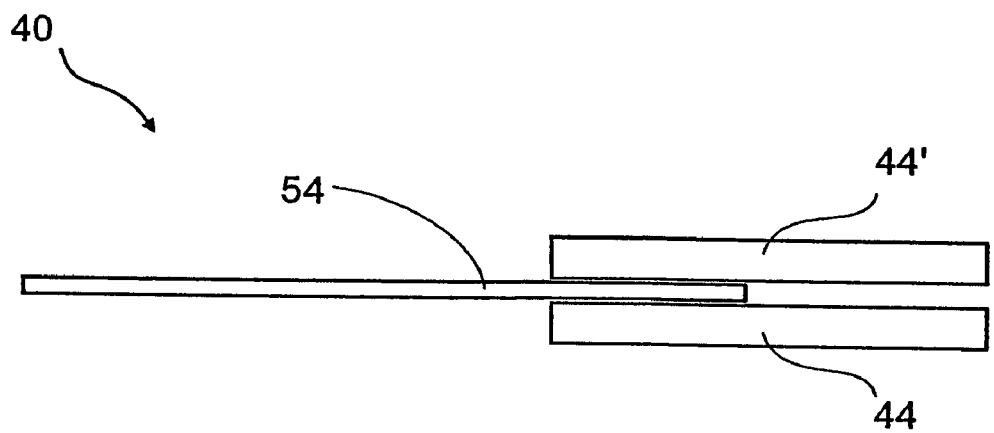
Figure 13C:
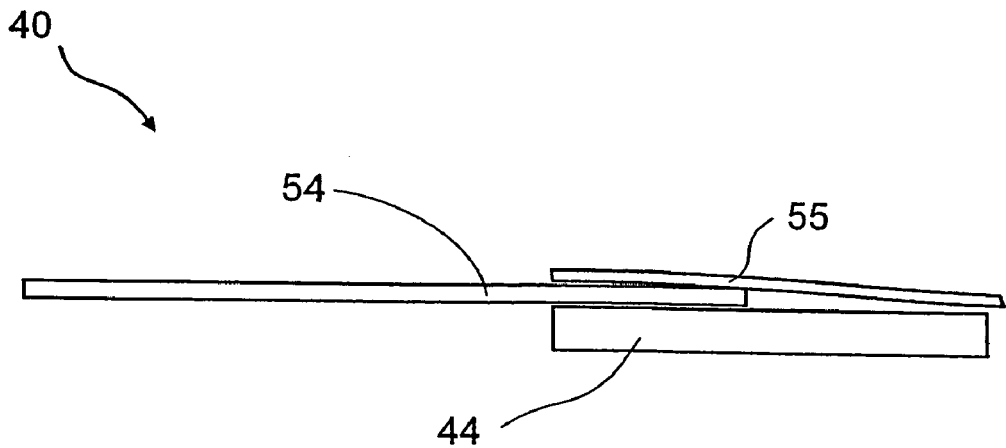
Figure 14A:
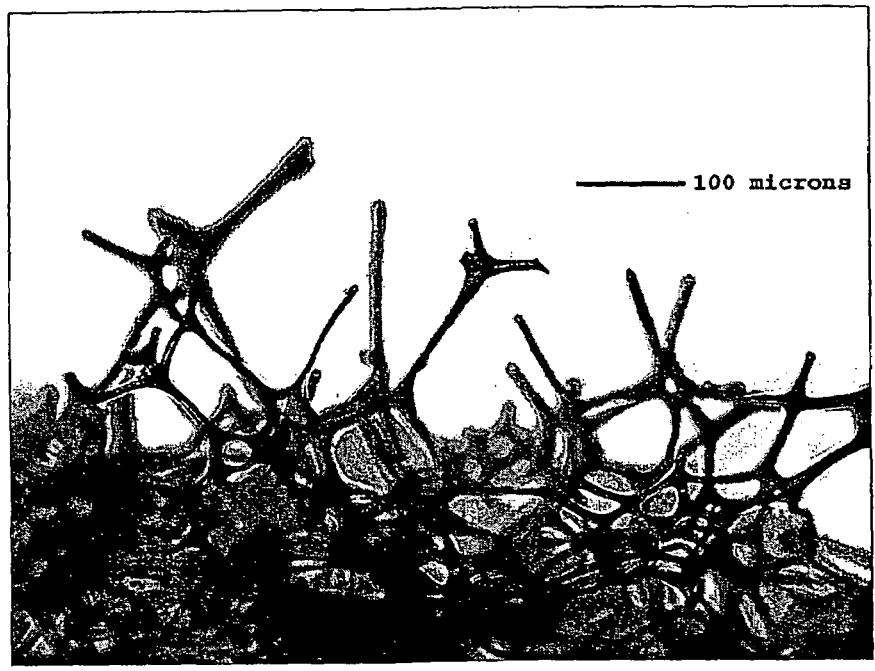
FIGS. 14A-F are photomicrographs of a commercial melamine-based foam sample in profile view with backlighting taken with a 10× objective.
Figure 14B:
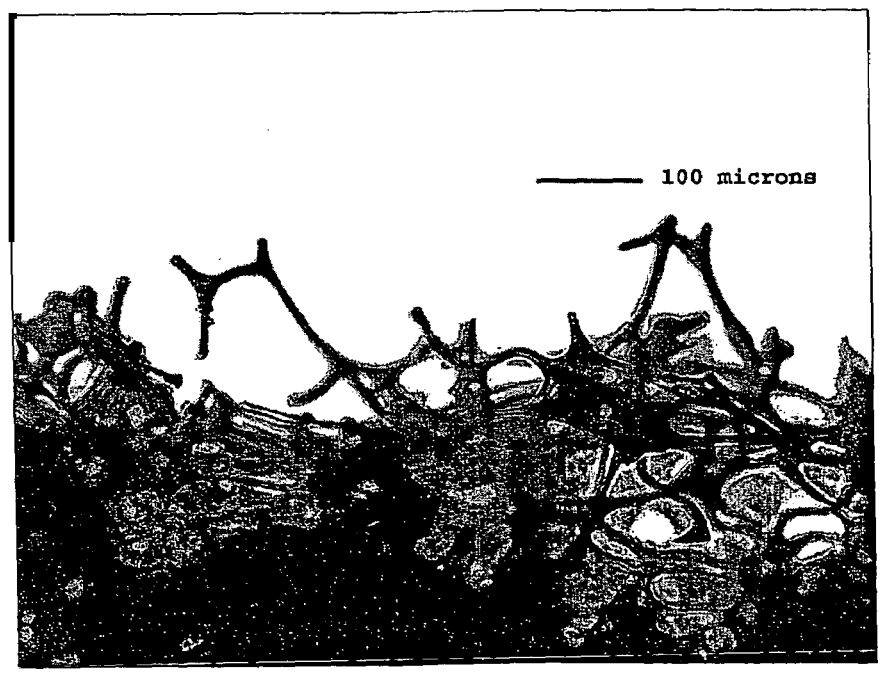
Figure 14C:
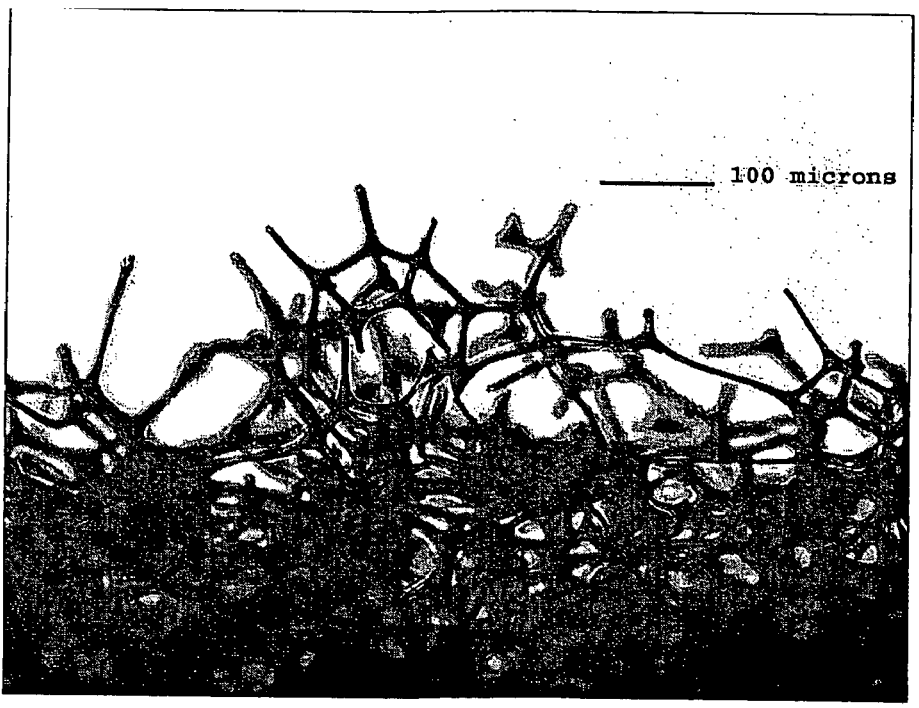
Figure 14D:
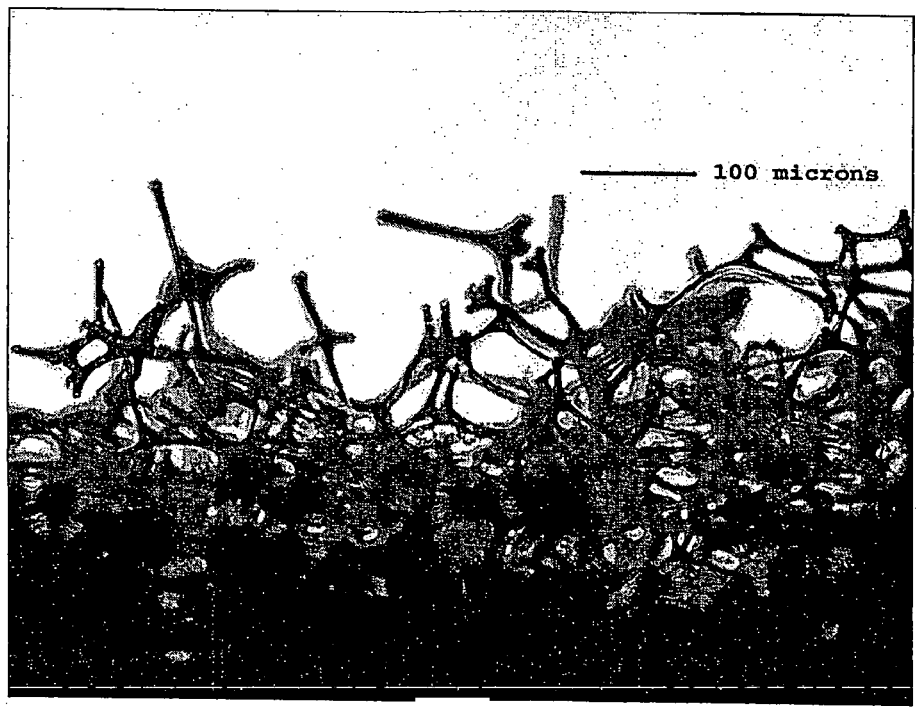
Figure 14E:
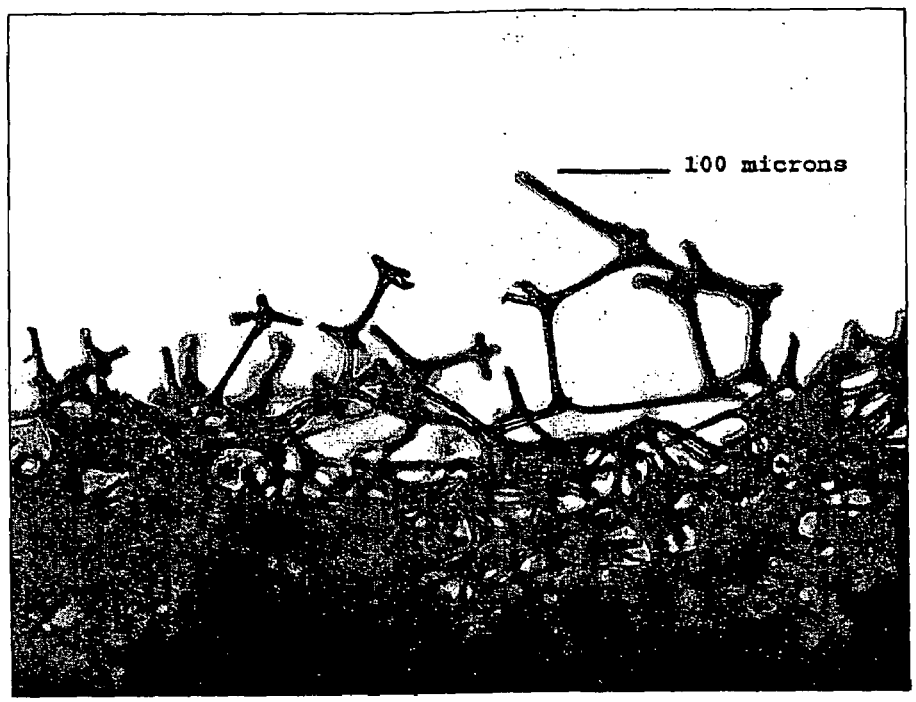
Figure 14F:
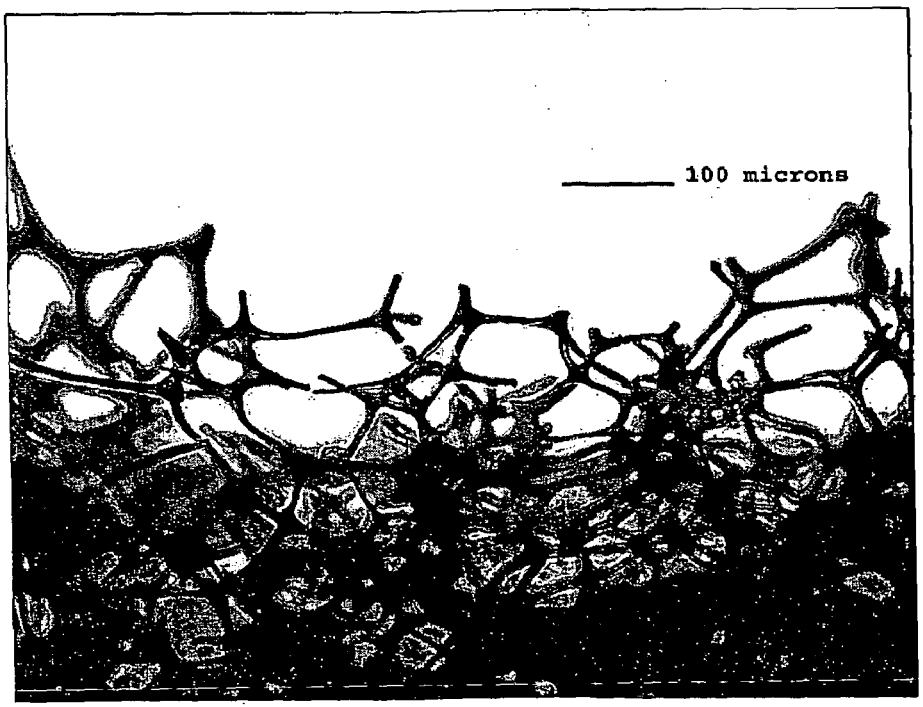
Figure 15A:
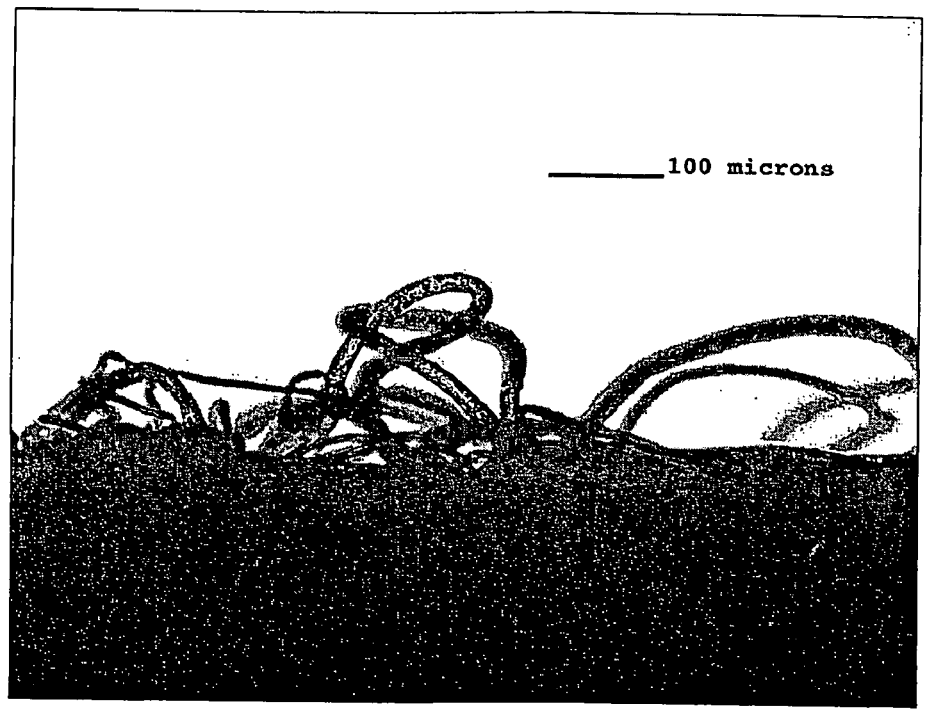
FIGS. 15A-F are photomicrographs of a spunlace web in profile view with backlighting taken with a 10× objective.
Figure 15B:
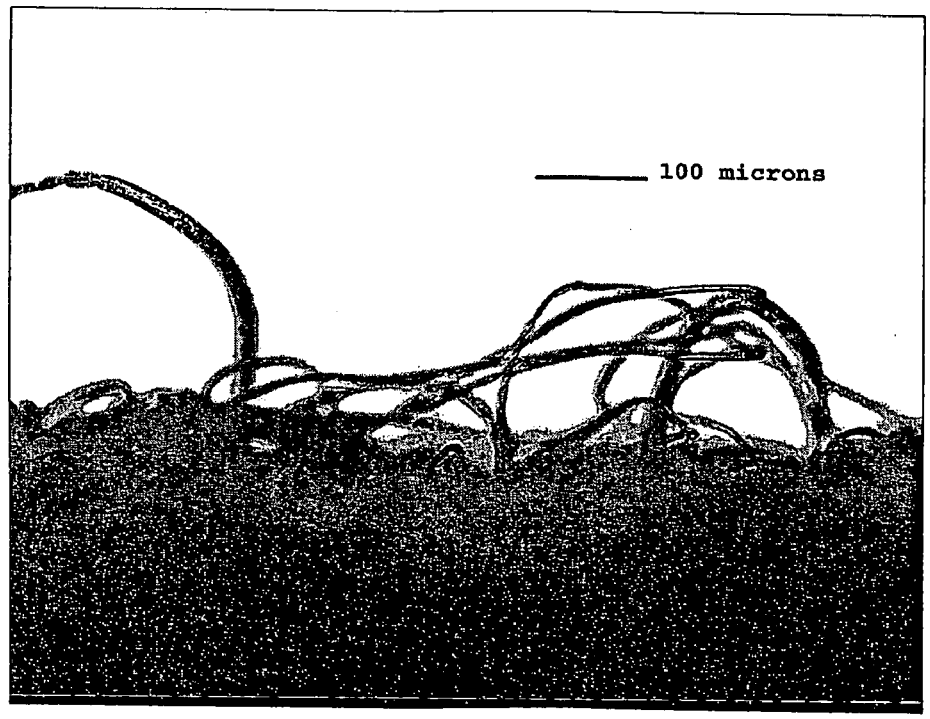
Figure 15C:
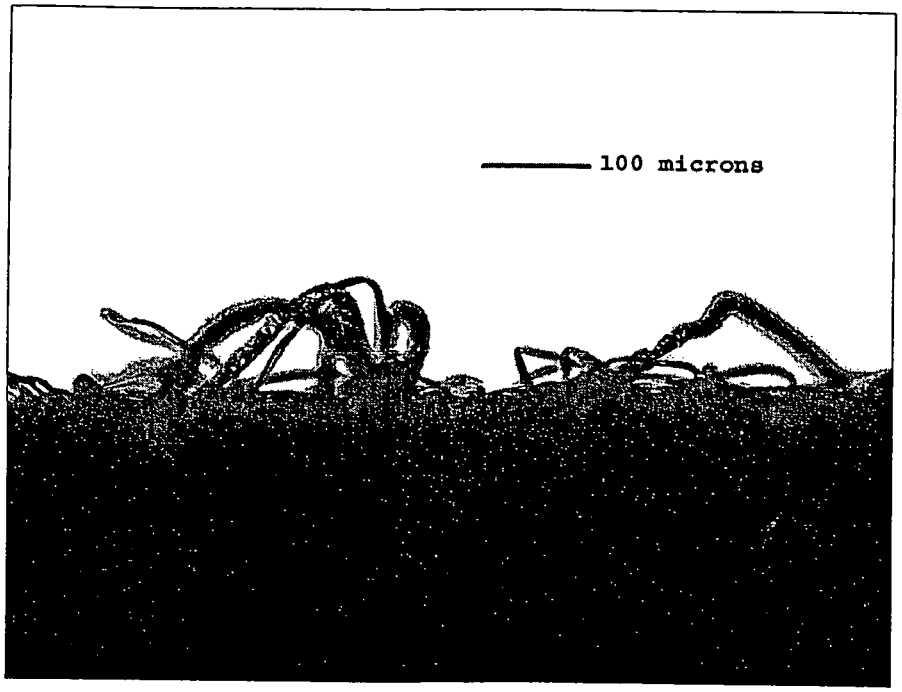
Figure 15D:
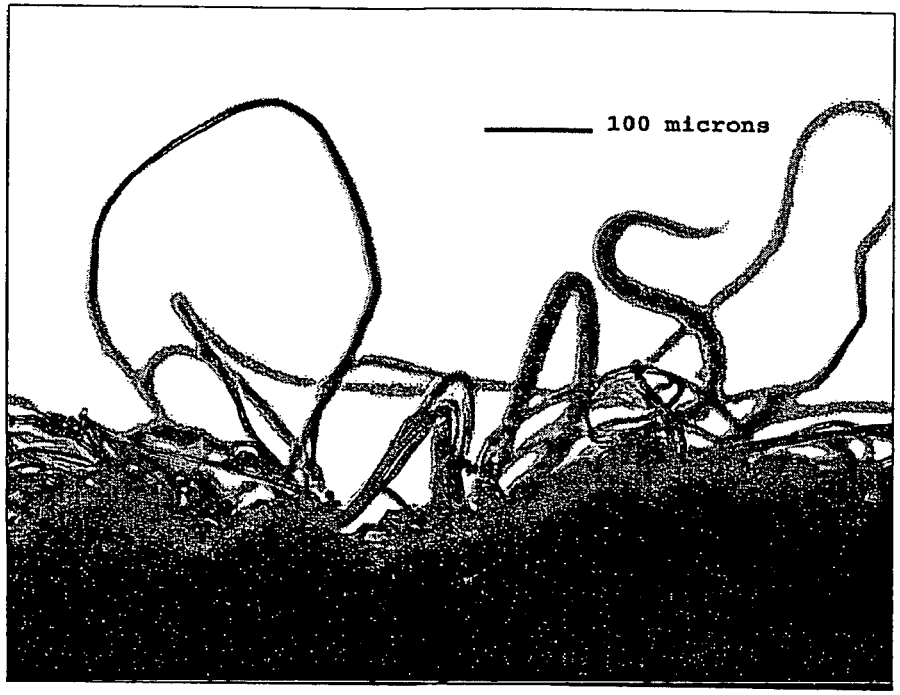
Figure 15E:
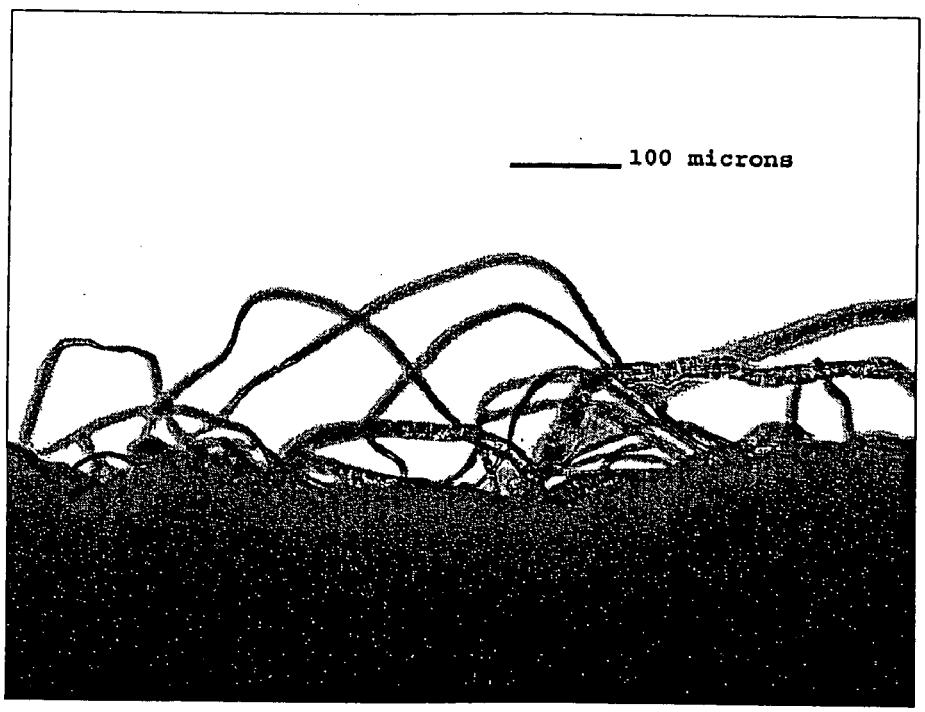
Figure 15F:
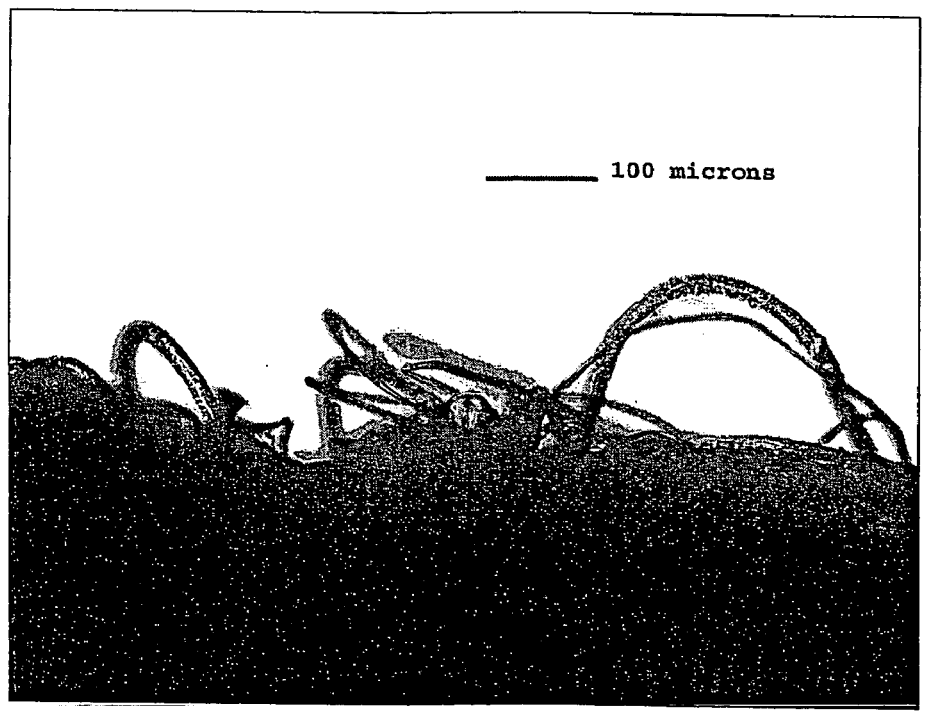
Figure 16A:
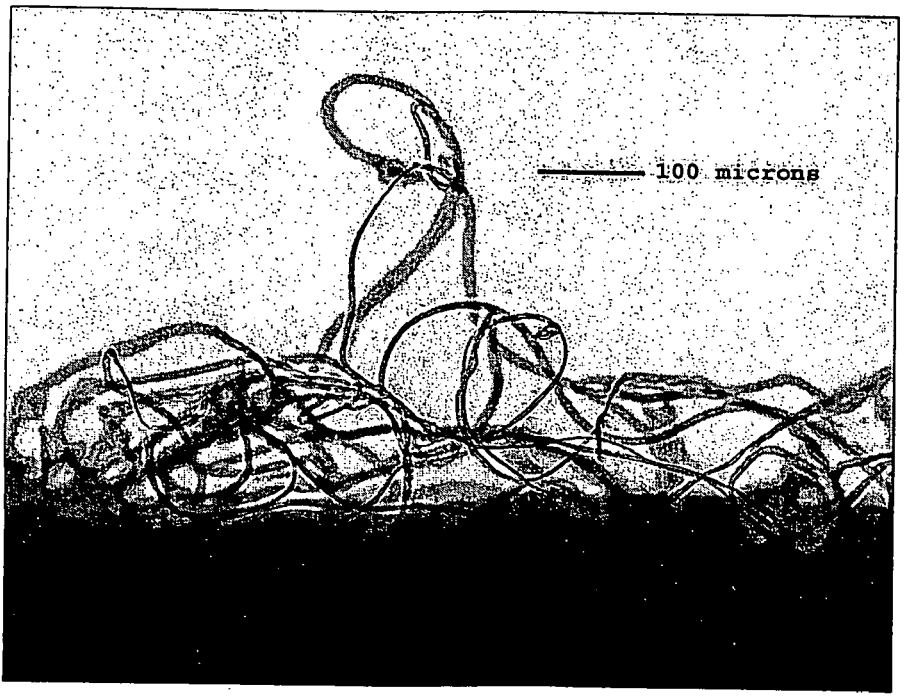
FIGS. 16A-F are photomicrographs of a polypropylene meltblown web in profile view with backlighting taken with a 10× objective.
Figure 16B:
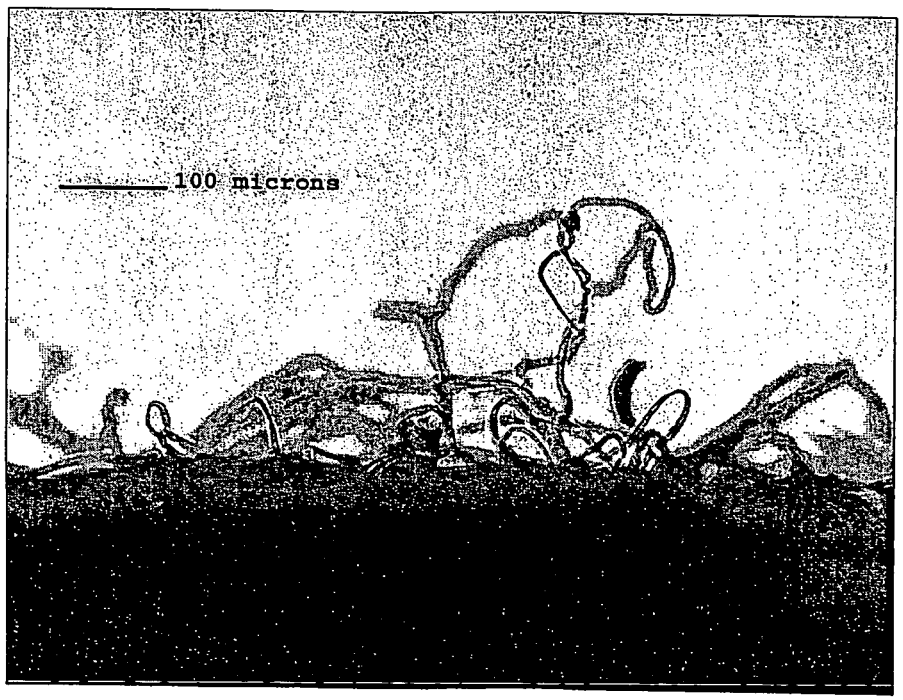
Figure 16C:
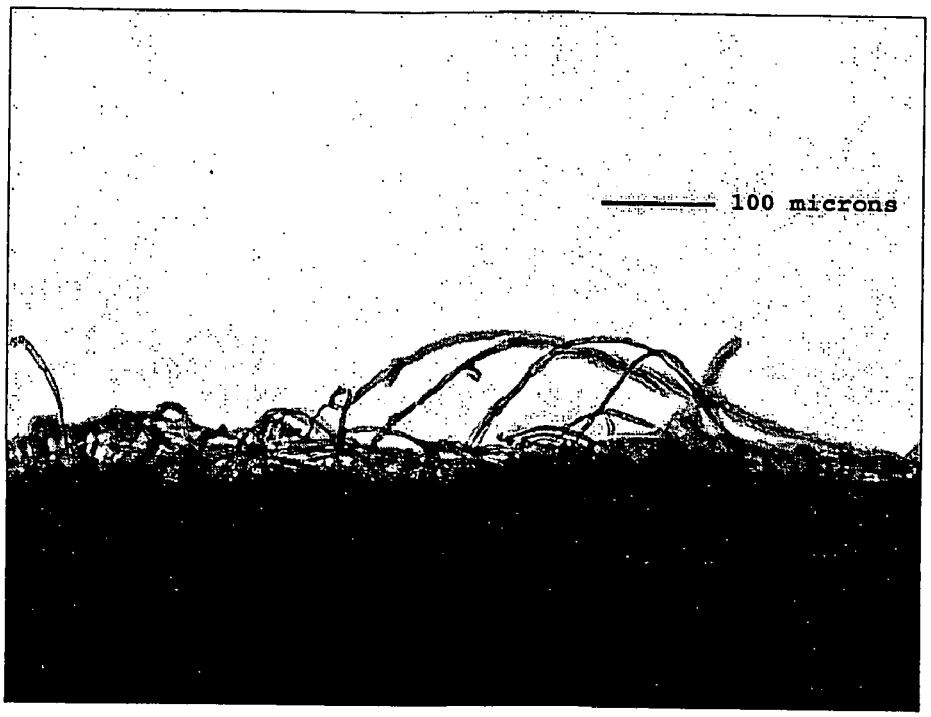
Figure 16D:
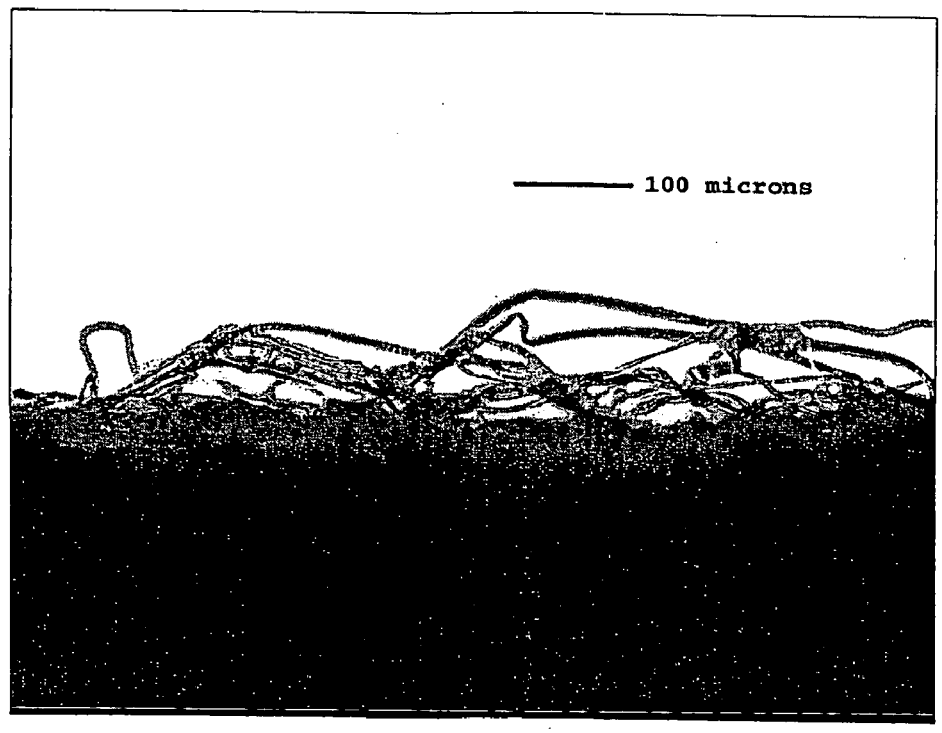
Figure 16E:
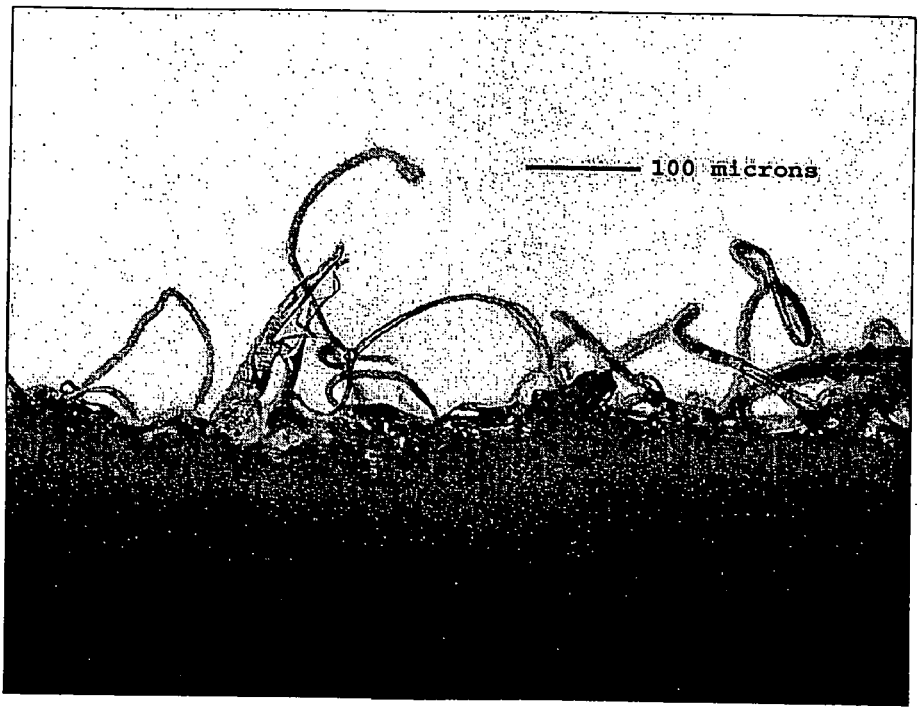
Figure 16F:
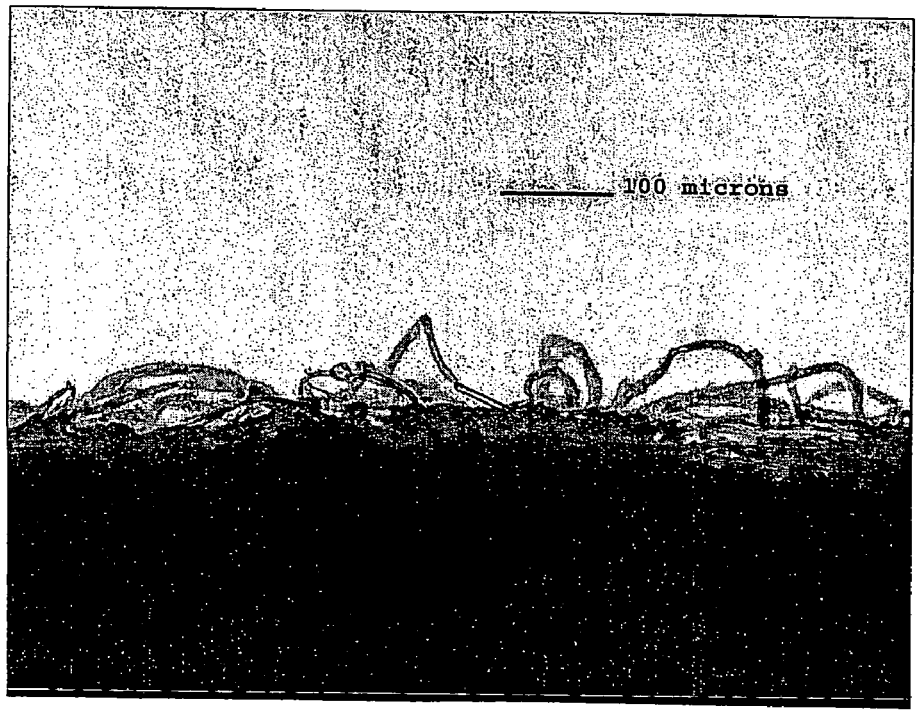
Figure 17A:
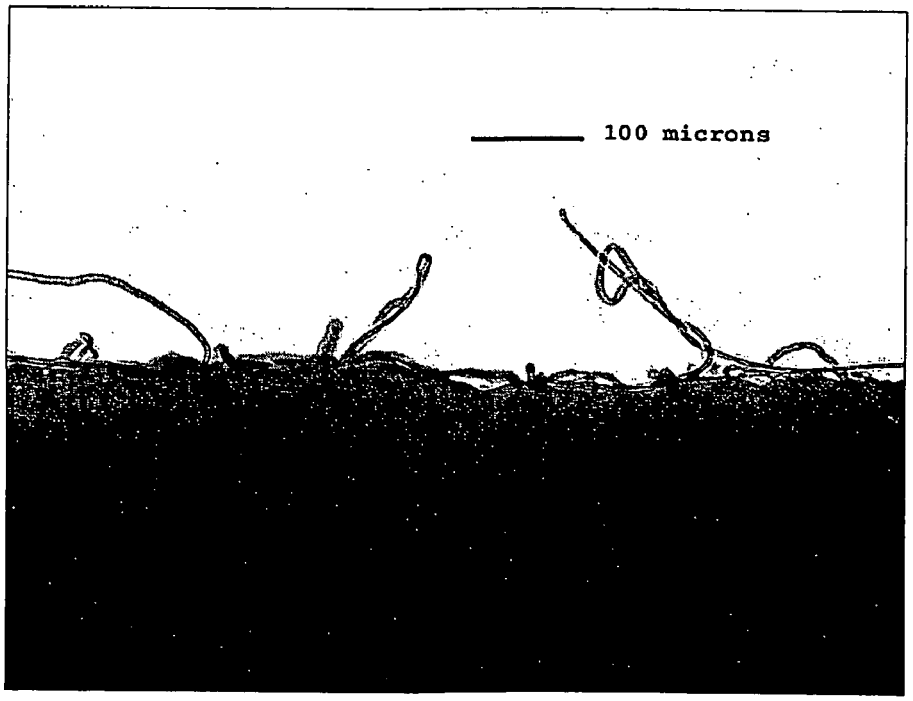
FIGS. 17A-F are photomicrographs of another polypropylene meltblown web in profile view with backlighting taken with a 10× objective.
Figure 17B:
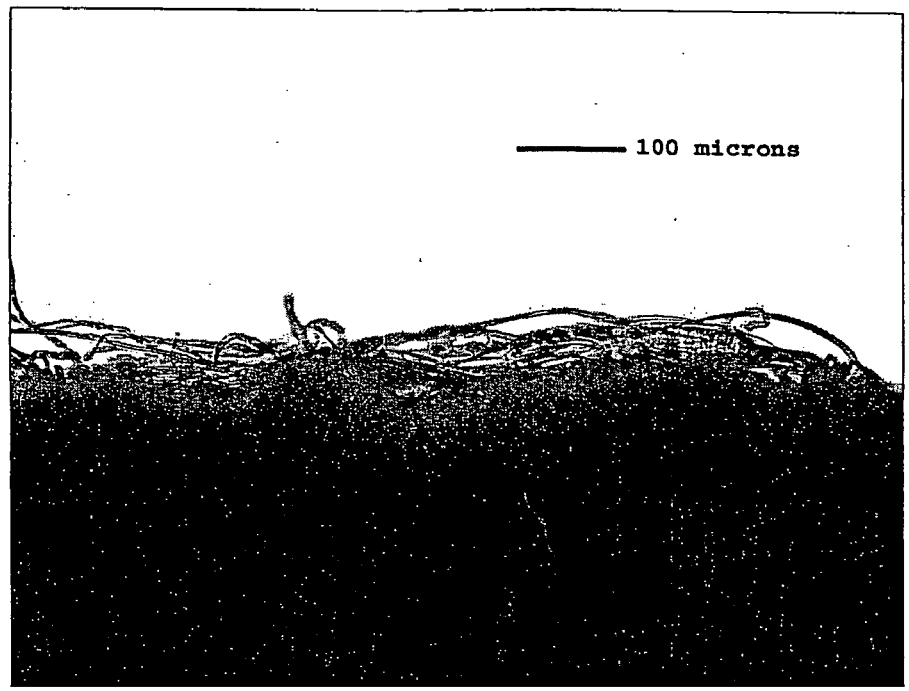
Figure 17C:
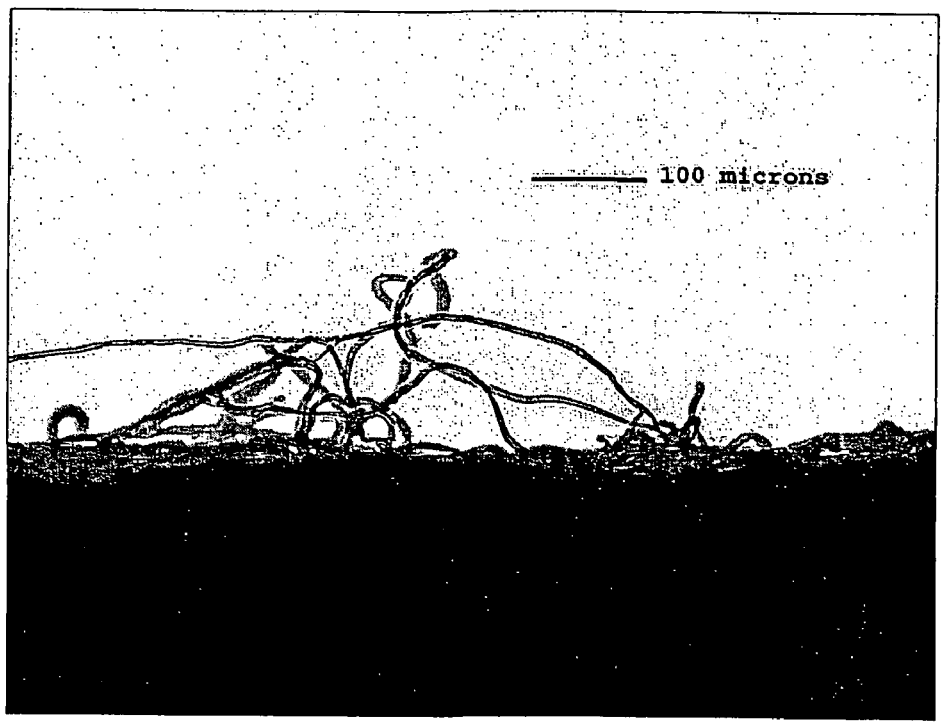
Figure 17D:
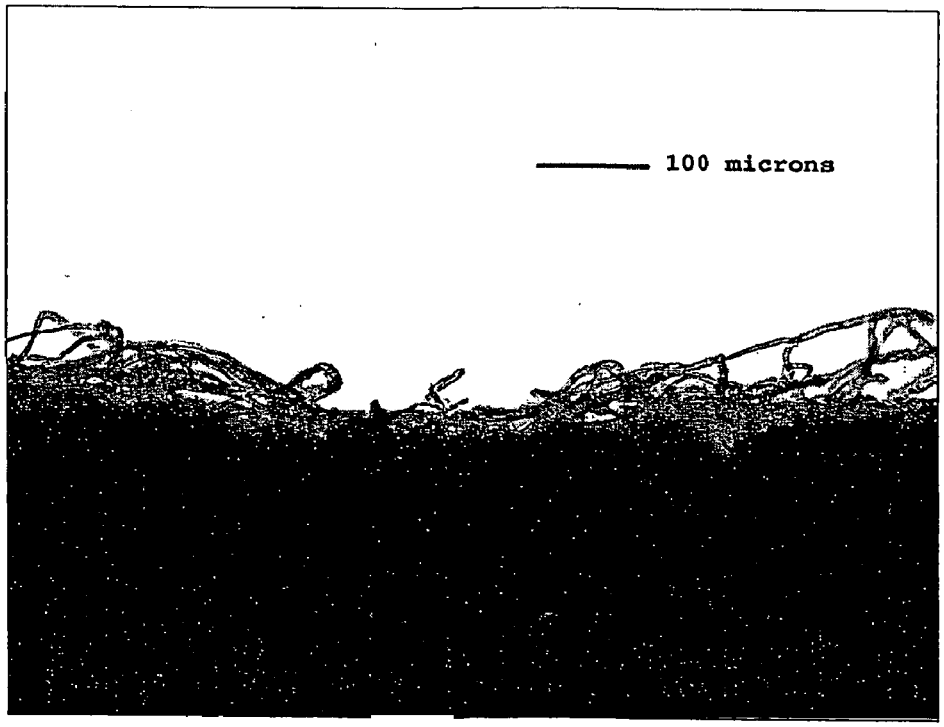
Figure 17E:
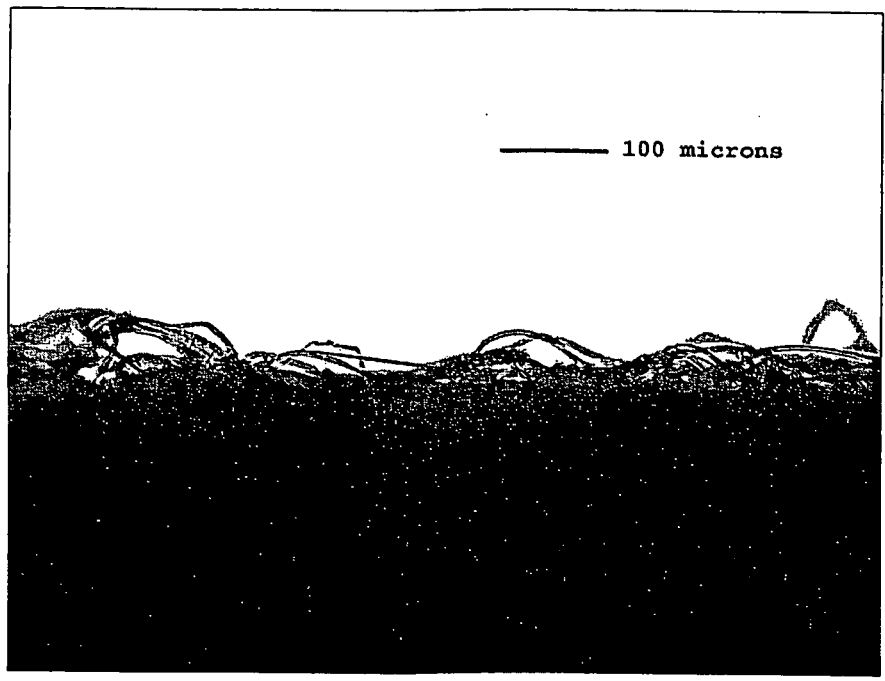
Figure 17F:
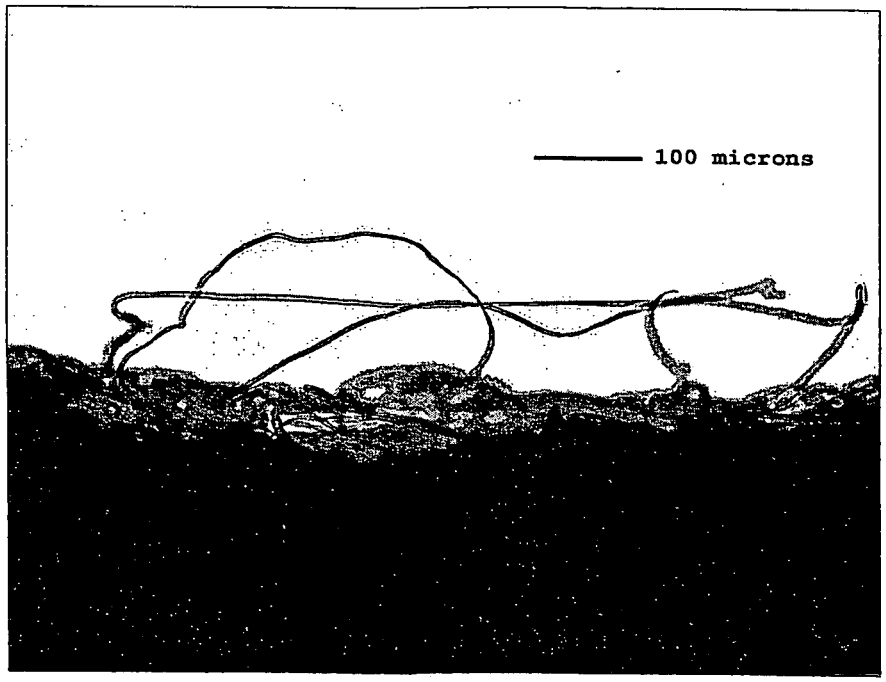
Figure 18A:
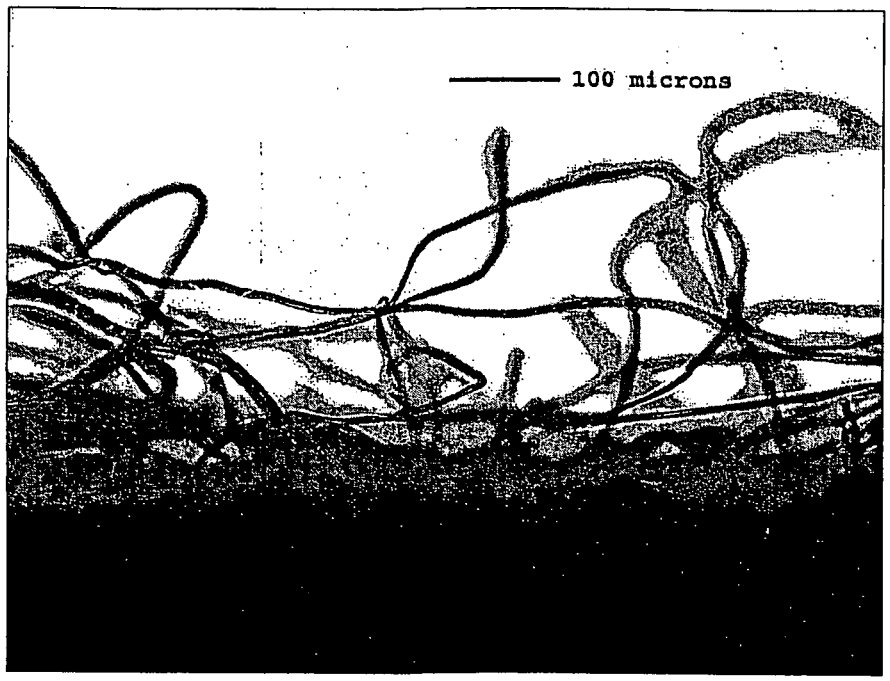
FIGS. 18A-E are photomicrographs of a spunlace web with microfibers in profile view with backlighting taken with a 10× objective.
Figure 18B:
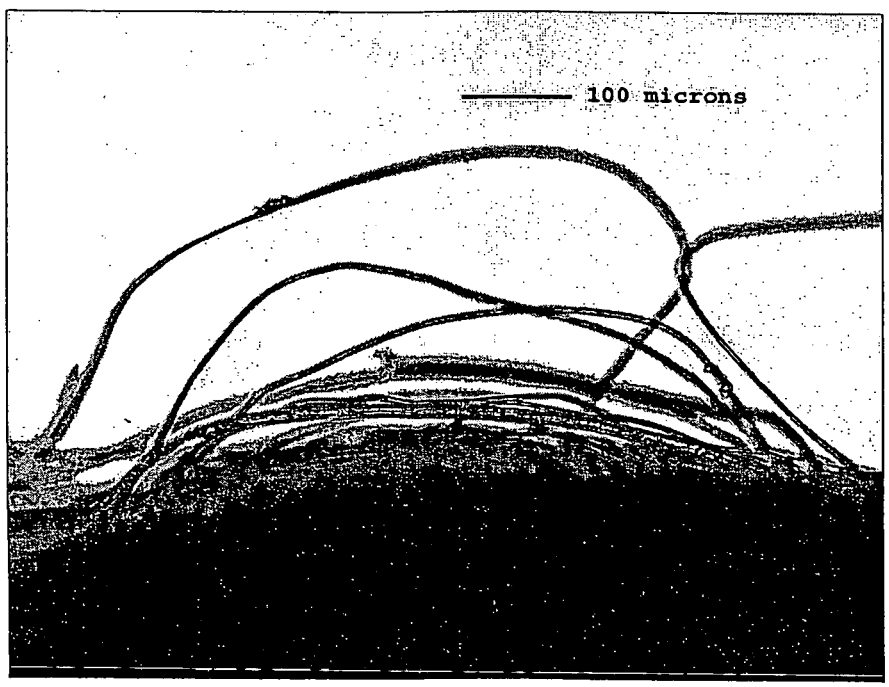
Figure 18C:
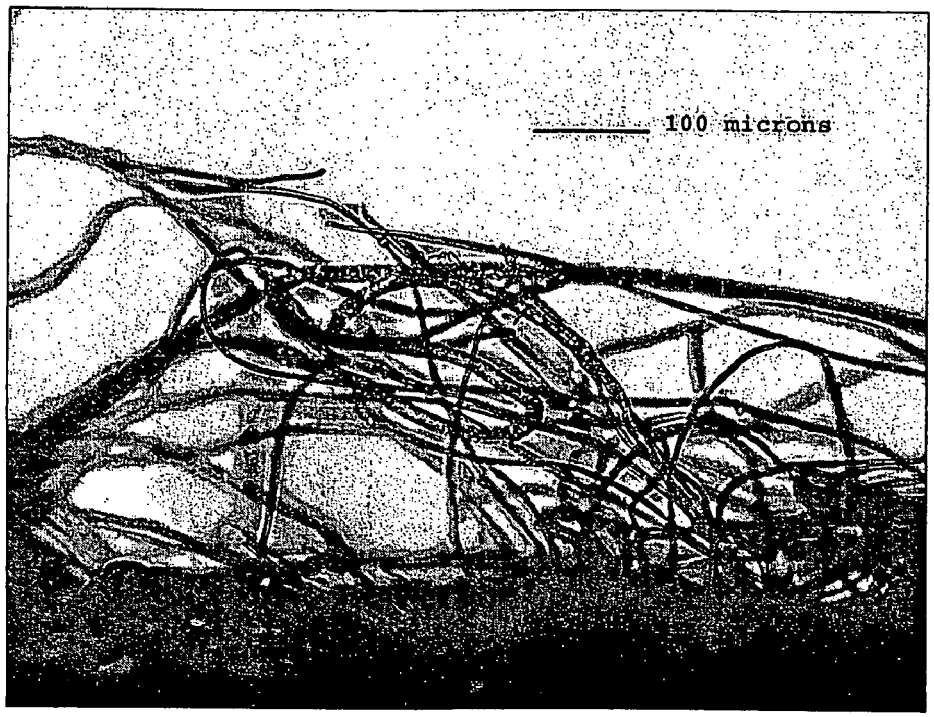
Figure 18D:
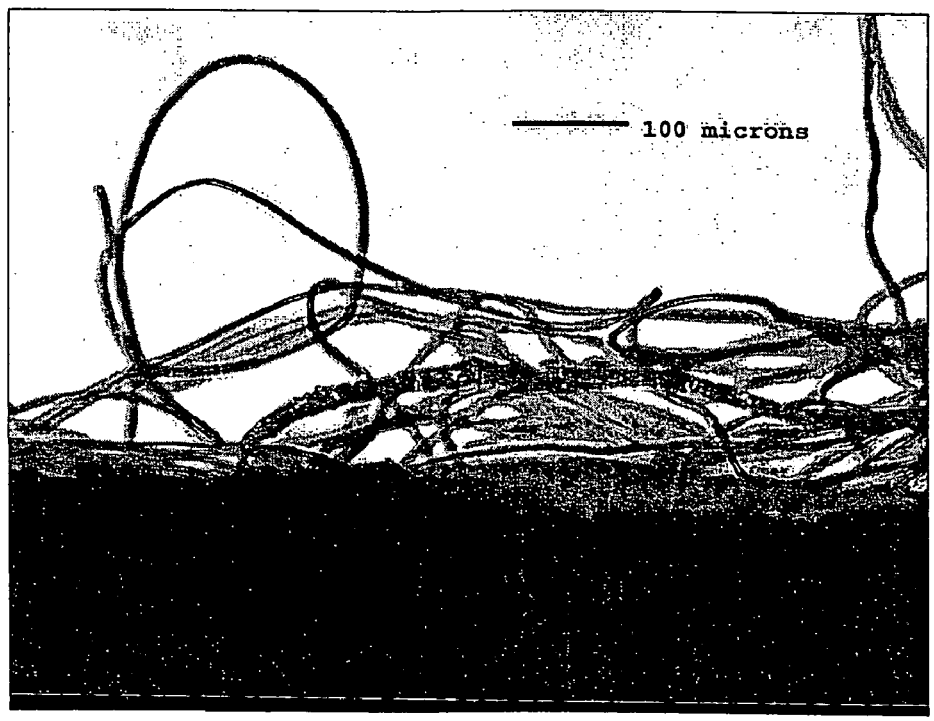
Figure 18E:
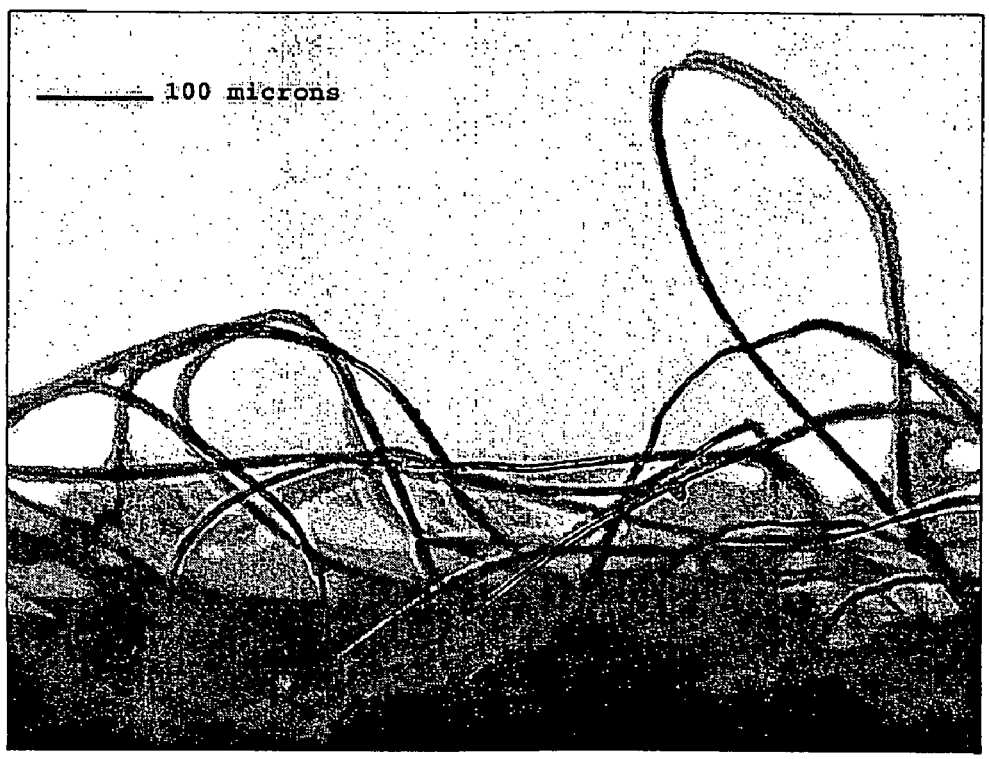
Figure 19A:
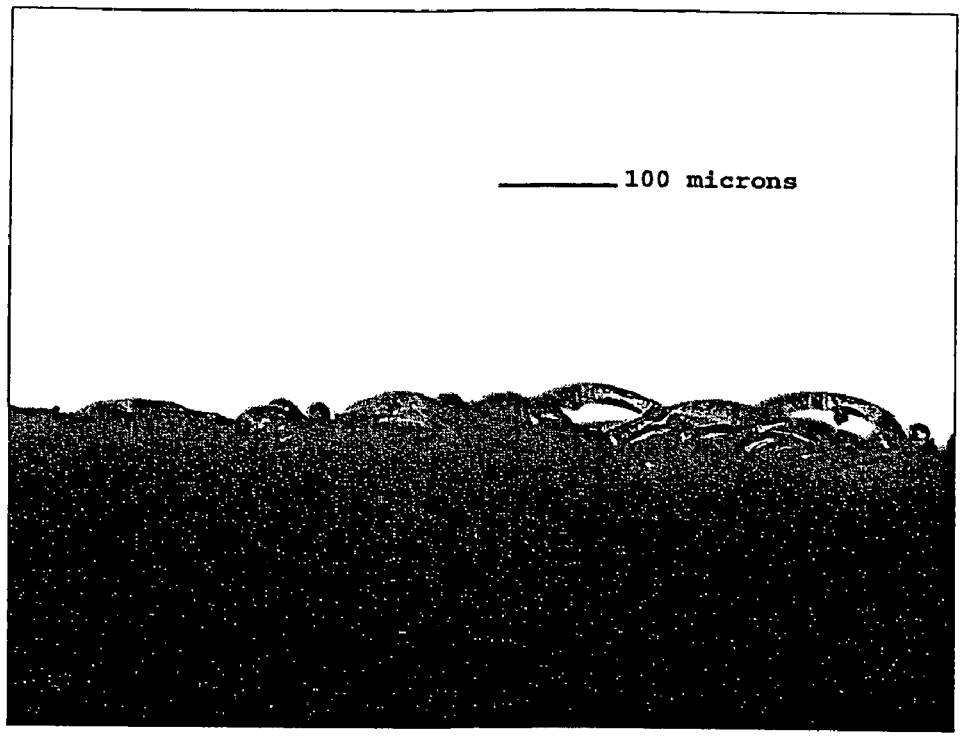
FIGS. 19A-F are photomicrographs of the spunbond landing layer in commercial HUGGIES® diapers in profile view with backlighting taken with a 10× objective.
Figure 19B:
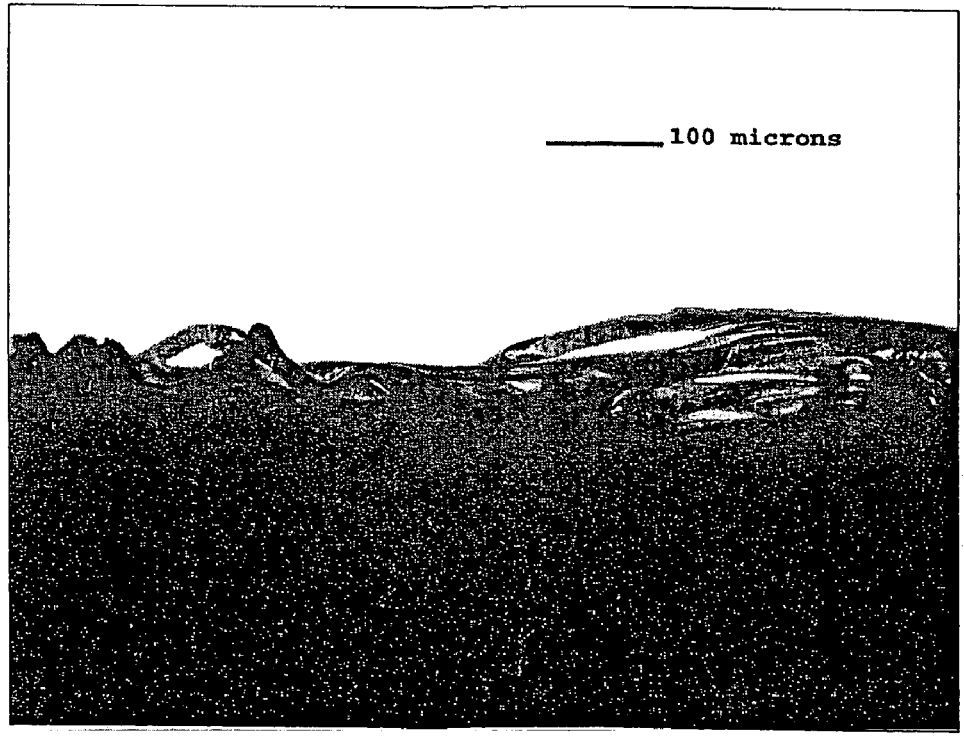
Figure 19C:
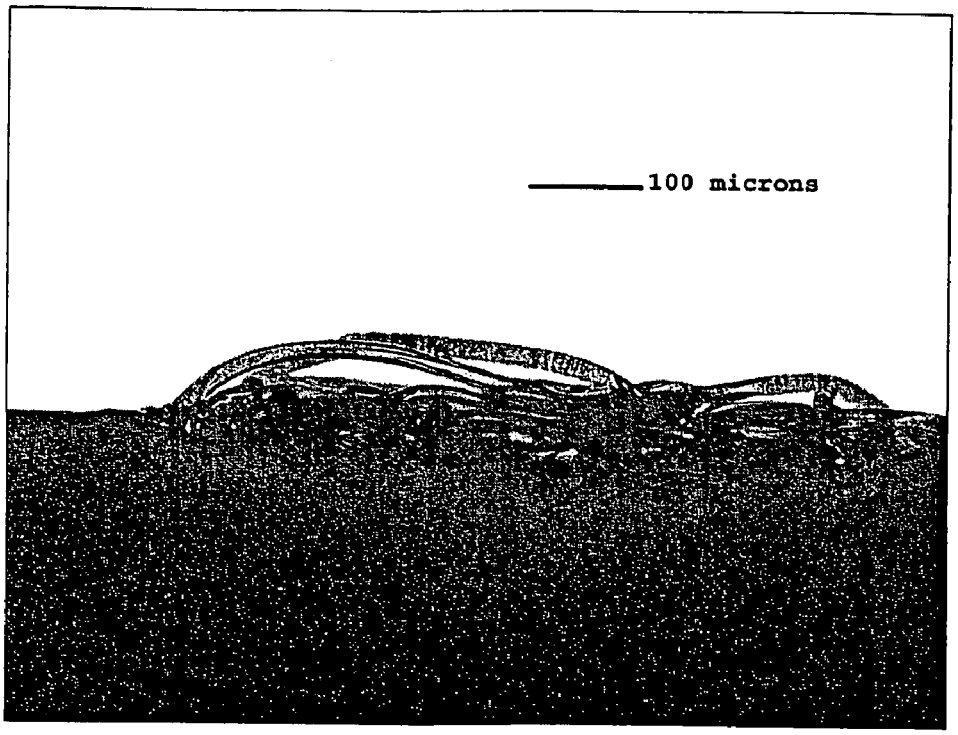
Figure 19D:
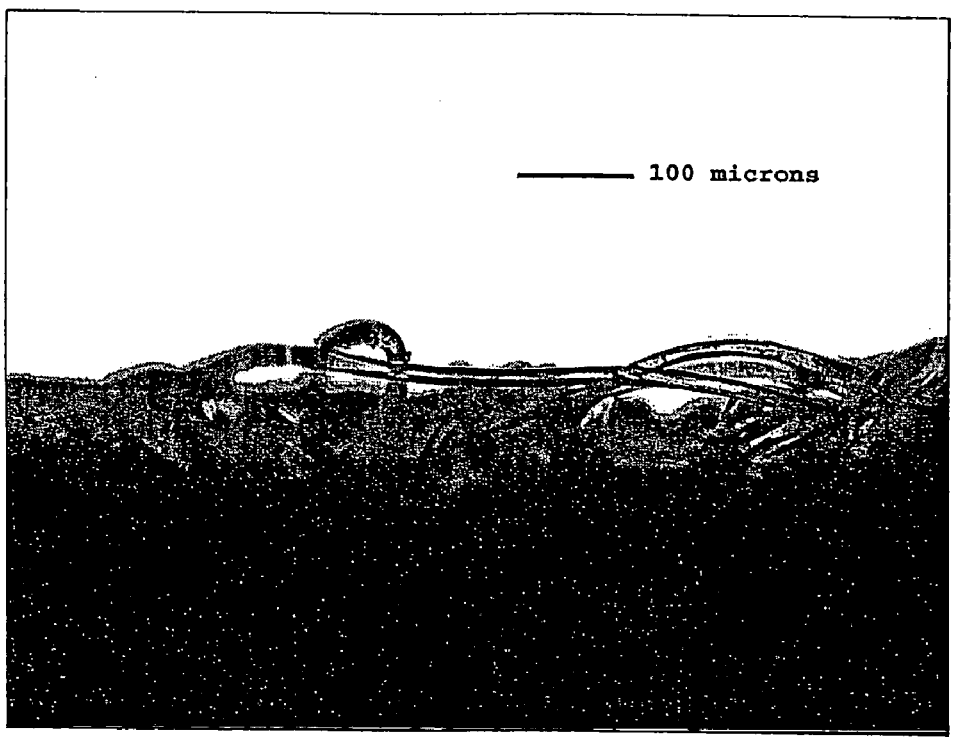
Figure 19E:
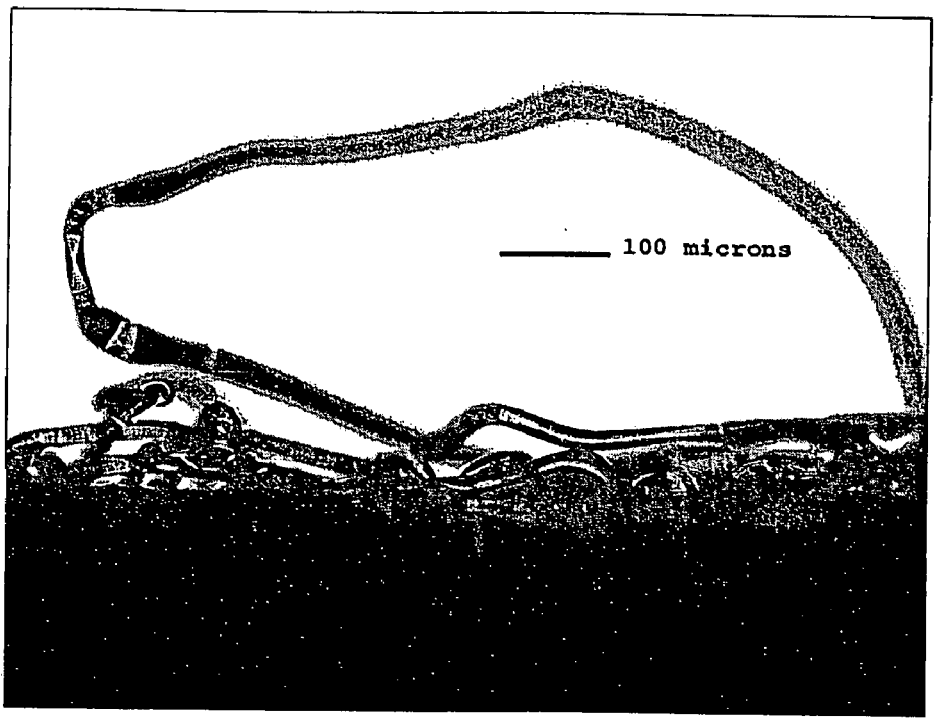
Figure 19F:
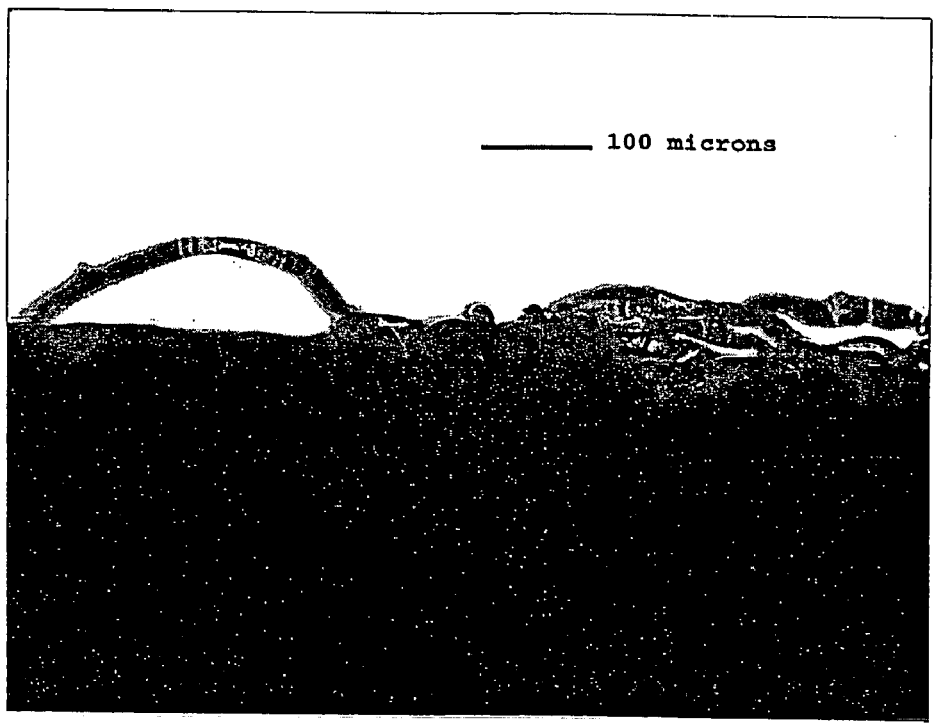

FIGS. 13A-C depicts some additional examples of foam layer fastening systems 40 based on the sandwich concept for improved fastener security. FIG. 13A shows a foam layer 44 joined to a landing material 54 with a covering 55 over the foam layer 44 such that the foam layer 44 is sandwiched and thus partly restrained from buckling away from the landing layer 54. FIG. 13B shows a landing layer 54 sandwiched between two foam layers 44 and 44'. FIG. 13C shows a landing layer 54 sandwiched between a cover 55 and a foam layer 44. The cover 55 may comprise another landing layer 54, may be integral with the landing layer 54 (e.g., a portion that is folded back to define the cover), or may not be a landing layer 54 or not be a foam layer 44, but may be a film or other web.

EXAMPLE 5

Good attachment with a layer of the BASOTECT® foam material was observed for an 0.8 osy nonwoven web manufactured by Kimberly-Clark Corporation, located in Houston, Tex., and comprising an elastomeric meltblown basesheet made of Arnitel® copolyester elastomer made by DSM Engineering Plastics, located in Evansville, Ind., joined to a bicomponent spunbond web by hydroentanglement. The bicomponent spunbond web was made of bicomponent splittable polyester/polyethylene fibers. The nonwoven web had a soft, fuzzy feel and engaged well with the foam layer.

EXAMPLE 6

To provide insight into the attachment mechanisms of the present invention, optical microscopy was applied to several materials to better understand their surface structure. A melamine foam material and several other nonwoven materials were examined in profile view with backlighting to demonstrate and compare the respective structures. Samples of the foam material and nonwoven materials were prepared by folding the foam material or nonwoven material 180 degrees over the sharp edge of a single edged razor blade that was coated with thin double sided tape. The edge of each foam and nonwoven material was digitally imaged using an Olympus AX-70 light microscope and backlighting to produce a silhouette of the edge. A number of photos were taken of each foam and nonwoven material. All photos were taken at identical magnification using a 10× objective and a 100-micron scale bar is imprinted on each photo. The microscopist taking the images provided images from several distinct portions of the foam and nonwoven materials to provide a relatively representative sampling of the surface structures.

FIGS. 14A-F are micrographs of melamine foam material taken from a thin layer sliced from a MR. CLEAN® Magic Eraser commercially available from Procter & Gamble, located in Cincinnati, Ohio. Here free-standing struts may be seen having lengths of about 10 to 130 microns.

FIGS. 15A-F are micrographs of Sample B in Example 3, a spunlace web with microfibers, having a trade designation of Code DE-153 from Polymer Group, Inc. This sample of the spunlace web, which was effective in engaging melamine foam layers, had a significant amount of elevated fibrous loops on the surface.

FIGS. 16A-F are micrographs of a white polypropylene meltblown web that proved effective in engaging melamine foam layers.

FIGS. 17A-F are micrographs of a pink polypropylene meltblown web made on the same machine and with the same materials as the white web of FIGS. 16A-F, but under conditions that gave a more tightly bonded surface. The pink meltblown web was ineffective in engaging melamine foam layers.

FIGS. 18A-E are micrographs of a spunlace web with microfibers made by PGI having microfibers and provided with an array of openings about 5 mm long and 2 or 3 mm wide, said to be from the PGI CLC-248-NOB spunlace series. The spunlace web was effective in engaging melamine foam material. (Due to limited sample quantity, only five images were obtained.)

FIGS. 19A-F are micrographs of the spunbond landing layer in commercial HUGGIES® diapers (Step 4 size, June 2004, United States). The spunbond landing layer was not effective in engaging melamine foam material.

EXAMPLE 7

Micrographs

To illustrate details of a foam structure suitable for the present invention, optical and SEM photomicrographs were obtained for portions of foam materials of a BASOTECT® foam pad distributed by Procter & Gamble, located in Cincinnati, Ohio, as a MR. CLEAN® Magic Eraser.

Figure 20:
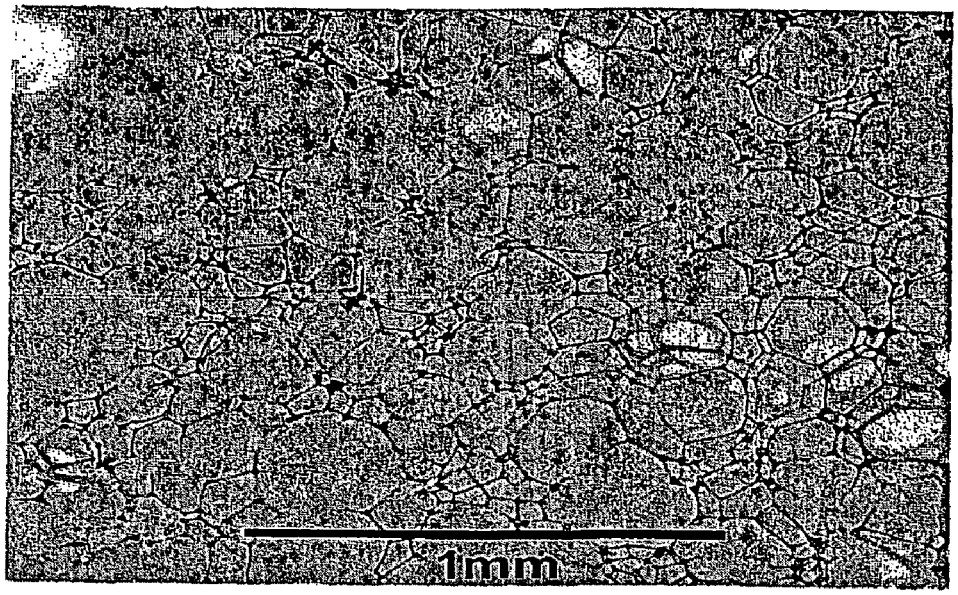
FIG. 20 is an optical photomicrograph at 80× magnification of a commercial melamine-based foam sample.

Examination at low magnification with reflected light and transmitted light microscopy of both the outer surfaces and of a cross-section of the foam material cut in half show that the foam material is a substantially uniform block of semi-rigid foam material with an open cell structure. For example, FIG. 20 was taken at 80× magnification in transmitted light showing a razor-cut cross-sectional surface of the MR. CLEAN® Magic Eraser. The foam material was cut in half through its center. All surfaces of the foam material, inside and outside, appear substantially as shown in FIG. 20, showing a network of interconnected filaments serving as struts in an open-celled foam network that appeared to be substantially uniform throughout.

Foam material samples were prepared for SEM analysis by cutting out a cube ½" on a side with a razor blade. Thinner segments of the foam material were cut from the cube and mounted onto a 1" diameter flat disc holder with double-stick tape. The mounted foam material samples were metallized with gold using a vacuum sputter coater to approximately 250 angstroms thickness. SEM analysis was performed with a JSM-840 electron microscope available from Jeol USA Inc., located in Peabody, Me., with an accelerating voltage of 5 kV, a beam current of 300 picoAmps, a working distance of 36 to 12 millimeters, and magnification of 30× to 15,000×.

Figure 21:
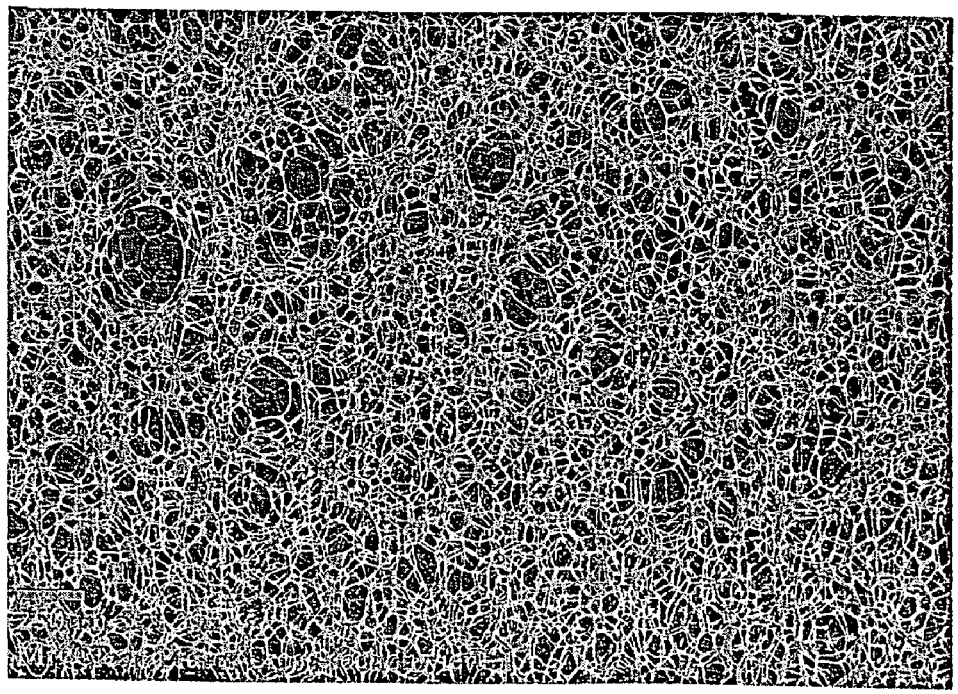
FIG. 21 is an SEM photomicrograph at 30× magnification of a razor-cut cross-sectional surface of a commercial melamine-based foam sample.

FIG. 21 is an SEM photomicrograph at 30× magnification of a razor-cut cross-sectional surface of a commercial melamine-based foam sample showing a substantially uniform network of interconnected filaments.

Figure 22:
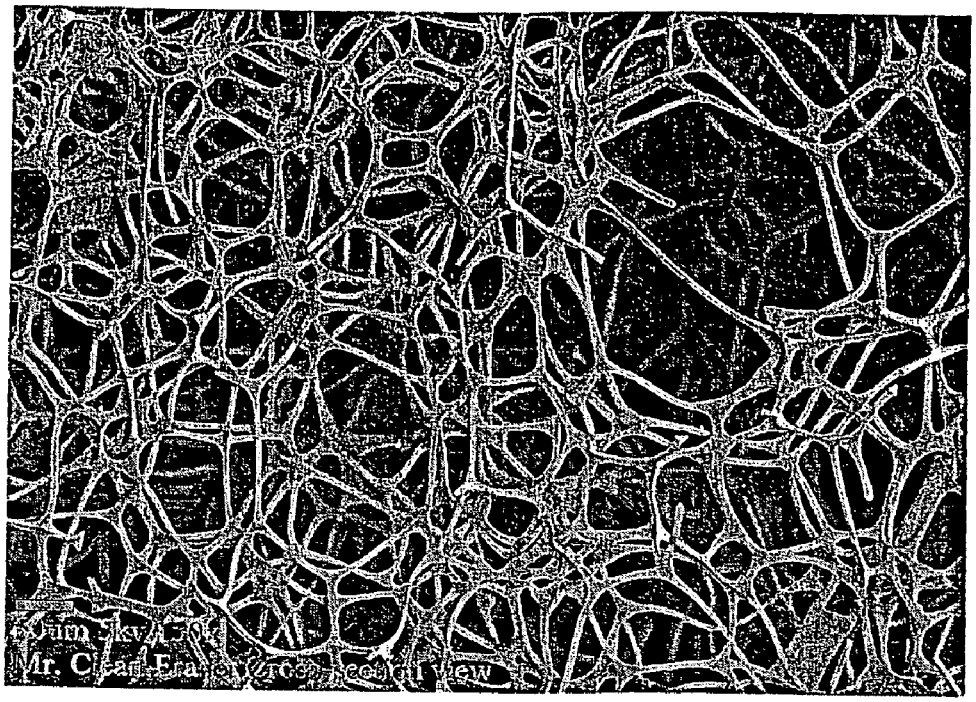
FIG. 22 is an SEM photomicrograph at 150× magnification of a razor-cut cross-sectional surface of a commercial melamine-based foam sample.

FIG. 22 is an SEM photomicrograph at 150× magnification of a razor-cut cross-sectional surface of a commercial melamine-based foam sample.

Figure 23:
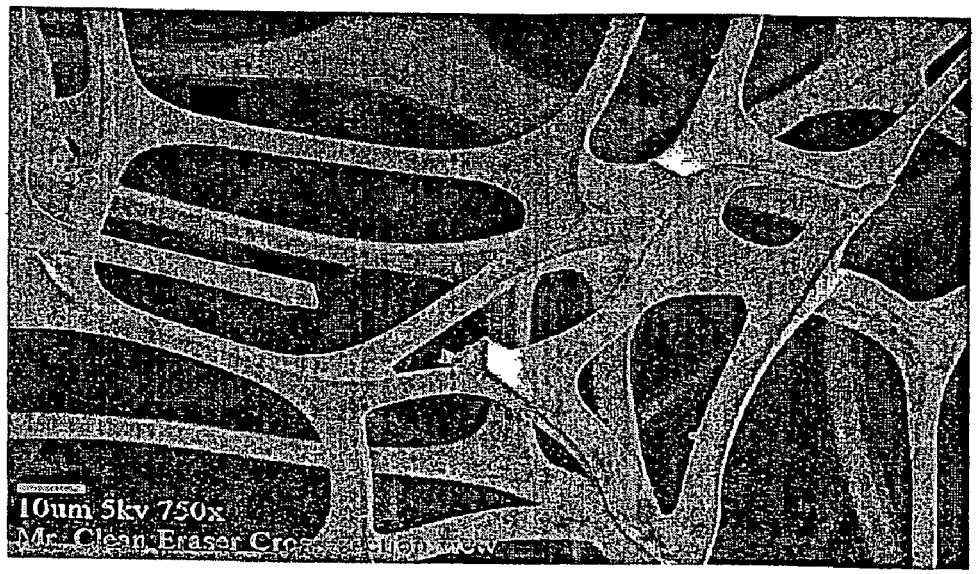
FIG. 23 is an SEM photomicrograph at 750× magnification of a razor-cut cross-sectional surface of a commercial melamine-based foam sample.

FIG. 23 is an SEM photomicrograph at 750× magnification of a razor-cut cross-sectional surface of a commercial melamine-based foam sample. Broken struts can be seen.

EXAMPLE 8

Air Permeability

To illustrate the highly breathable and air permeable nature of the foam layers of the present invention, BASOTECT® foam layers of varying thickness were evaluated for air permeability using the FX 3300 Air Permeability device manufactured by Textest AG (Zürich, Switzerland), set to a pressure of 125 Pa (0.5 inches of water) with the normal 7-cm diameter opening (38 square centimeters), operating in a Tappi conditioning room (73° F., 50% relative humidity). Foam layer samples cut to about 40 cm squares or larger were tested, with three regions of each foam layer sample (or stack of foam layer samples when two layers of foam material were used) being averaged to give the reported values in cubic feet per minute (CFM), as shown in Table 2. The standard deviation of the three measurements are also shown, as is the basis weight (dry mass of the foam material divided by the plan area of the foam material).

TABLE 2

Air permeability results for melamine foam samples.

| Sample | CFM | St. Dev. | Basis Weight (g/m$^2$) |
|---|---|---|---|
| 2-mm thick layer of BASOTECT ® 2011 | 872 | 5.9 | 17.2 |
| Two layers of 2-mm thick BASOTECT ® 2011 | 494 | 2.3 | 34.4 |
| 2-mm thick layer of BASOTECT ® 3012 | 815 | 7.8 | 18.8 |
| Two layers of 2-mm thick BASOTECT ® 3012 | 467 | 6.2 | 37.5 |
| 9-mm thick layer of BASOTECT ® 2011 | 265 | 3.5 | 107.7 |

In general, a foam layer for any application of the present invention may have an air permeability of any of the following: about 100 CFM (cubic feet per minute) or greater, about 200 CFM or greater, about 300 CFM or greater, about 500 CFM or greater, or about 700 CFM or greater, such as from about 250 CFM to about 1500 CFM, or from about 150 CFM to about 1000 CFM, or from about 100 CFM to about 800 CFM, or from about 100 CFM to about 500 CFM. Alternatively, the air permeability of the foam layer may be about 400 CFM or less. The foam layer may have a thickness of about 9 mm or less, such as about 3 mm or less or about 2 mm or less, and may have a basis weight of about, 150 g/m$^2$ or less, about 100 g/m$^2$ or less, about 50 g/m$^2$ or less, and about 40 g/m$^2$ or less, such as from about 10 g/m$^2$ to about 80 g/m$^2$, or from about 15 g/m$^2$ to about 55 g/m$^2$.

EXAMPLE 9

Forming Reinforced Foam Layers on a Pilot Line

A set of reinforced foam layers according to the present invention were made by laminating layers of melamine-based foam material to reinforcing layers using a hot melt adhesive material applied on a pilot meltblown device. Two different kinds of reinforcing layers were used, a commercial VIVA® paper towel web, commercially available from Kimberly-Clark Corp., located in Dallas, Tex. and an 0.55 ounce per square yard (osy) polypropylene spunbond web, commercially available from Kimberly-Clark Corp., Lexington Mill, located in Lexington, Ky. Sliced melamine foam material samples were manually taped onto a moving carrier fabric (a spunbond web that was not to be joined to the foam material, but served merely as a carrier for application of the adhesive) traveling at a speed of about 50 feet per minute. The moving fabric brought the foam material samples beneath a meltblown nozzle through which a fine spray of a polypropylene-based hot melt adhesive material comprising Eastman P1023 Polypropylene made by Eastman Chemical Company, located in Kingsport, Tenn., and about 10% DPX 584 elastomer from Dexco Polymers of Exxon Mobil Chemical Company, located in Houston, Tex. The hot melt adhesive material was applied at a basis weight of about 20 grams per square meter for joining to VIVA® paper towel web and 10 grams per square meter for joining to the spunbond web. After the meltblown hotmelt adhesive material was applied to the foam material, the adhesive-treated side was immediately joined to the reinforcing layer deployed from a roll, and contact was secured by passing both into an unloaded nip between two rotating rolls that brought the two materials into contact under mild pressure to avoid damage to the foam material.

To produce thin layers of melamine-based foam material, a commercial block of BASOTECT® foam pad available from BASF, located in Ludwigshafen, Germany, was obtained through the purchase of a MR. CLEAN® Magic Eraser, appearing to be a formaldehyde-melamine-sodium bisulfite copolymer. This melamine-based foam material appears to be BASOTECT® 3012, which has been densified under load at elevated temperature to a density of about 0.009 g/cc (9 kg/m$^3$). The block of foam material was cut into strips of thin slices (typically 2 mm thick) using a commercial meat slicer, Chef's Choice VariTilt Model 632, commercially available from EdgeCraft Corp., located in Avondale, Pa., and having a UPC No. of 087877632008.

Figure 24:
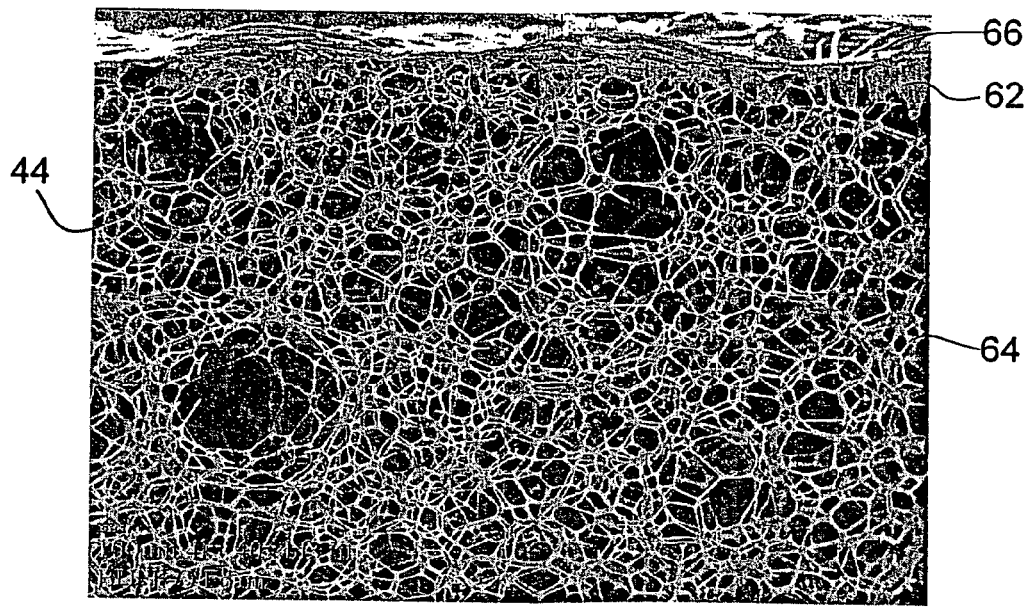
FIG. 24 is a 40× SEM view of a cross-section of a reinforced foam layer comprising melamine foam and a spunbond web.
Figure 25:
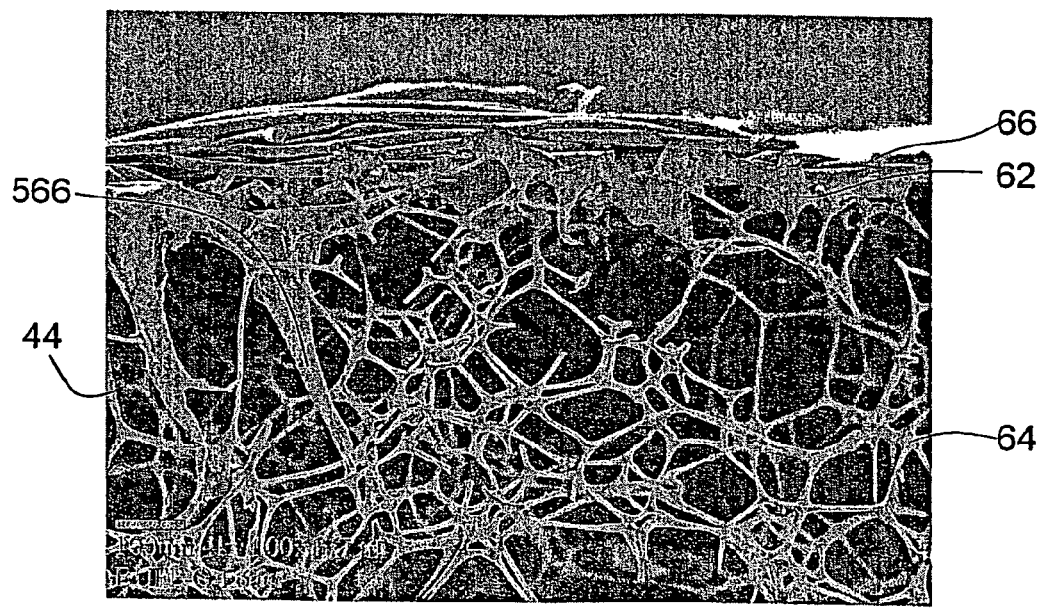
FIG. 25 shows the same foam material as in FIG. 24 but at 100× magnification.

The foam material strips cut from the MR. CLEAN® product had the same planar dimensions as the product itself, 2.5 inches×4.75 inches. In making the foam material samples, the major axis of the foam material (the direction spanning 4.75 inches) was aligned with the machine direction of the reinforcing layer. The thickness of the foam layers typically ranged from 2 mm to about 8 mm, though other thickness ranges are to be considered within the scope of some versions of the present invention. FIG. 24 shows a 40× SEM view of a cross-section of a reinforced foam layer 44 comprising melamine foam material 64 from the MR. CLEAN® product joined to a spunbond web reinforcing layer 66 with meltblown adhesive material 62. FIG. 25 shows the same foam material sample at 100× magnification. In FIG. 25, some portions of the adhesive material 62 form "stringers" 566 that extend into the foam material 64 by a distance greater than the characteristic cell size of the foam material 64 (here the penetration depth is roughly 1.5 to 2 times a typical cell size).

Figure 26:
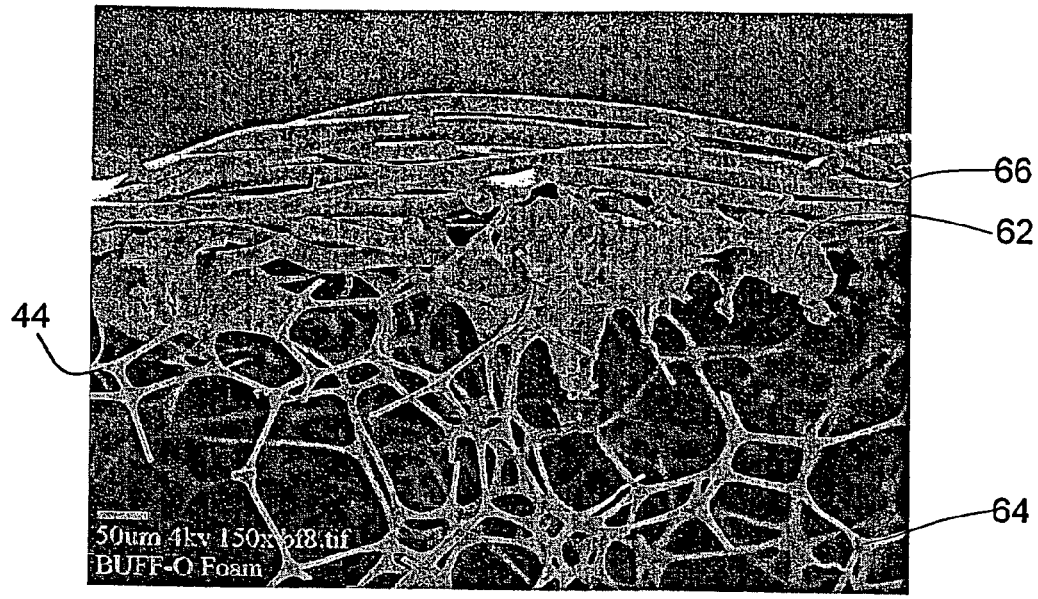
FIG. 26 is a 100× SEM view of a cross-section of another reinforced foam layer comprising melamine foam and a spunbond web.
Figure 27:
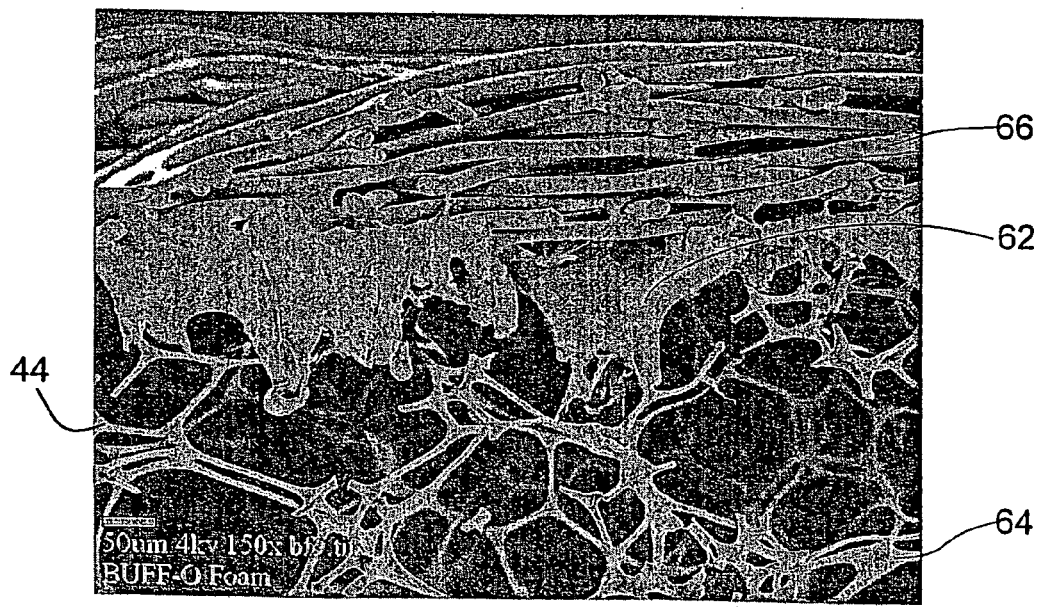
FIG. 27 is a 100× SEM view of a cross-section of another reinforced foam layer comprising melamine foam and a spunbond web.

FIGS. 26 and 27 show similar samples at 150× magnification.

The foam material samples, each having dimensions of 4.75 inches×2.5 inches and an area of 11.9 square inches, were then tested according to the Zwick Flexibility test. The materials of the reinforcing layer unbonded to foam layer were also tested, as were slices of the MR. CLEAN® foam material unbonded to the reinforcing layer and 2-mm thick slices of BASOTECT® 2011 foam material. All samples were conditioned at 23° C. and 50% relative humidity for a minimum of 4 hours prior to testing. Results are shown in Table 3 below. Note that the addition of the spunbond reinforcing layer, which by itself is too drapable to yield a measurable flexibility modulus, gave a significant increase in Zwick Flexibility Modulus (E) of the foam material when the two are joined. The adhesive material contributes to the flexibility. It is believed that even lower bending stiffness values of the composite material (foam material plus reinforcing layer) could be obtained by using less adhesive material or a more flexible or elastomeric adhesive material, or by using other bonding methods such as application of adhesive material in a spaced-apart pattern, sewing, ultrasonic bonding with a spunbond web in a spaced apart pattern, etc.

TABLE 3

Zwick Flexibility properties of foam layers bonded to reinforcing layers.

| Sample ID | Weight (g) | Caliper 0.05 psi (mm) | Density g/cc | Peak Load (g) | Max Slope (g/mm) | Slope (N/m) | Modulus E (KPa) | E (psi) | Bending Stiffness (Nm) | Basis Weight gsm |
|---|---|---|---|---|---|---|---|---|---|---|
| MR. CLEAN ® Slices | 0.13 | 1.93 | 0.009 | 12 | 7 | 69 | 1829 | 265 | 0.0011 | 17 |
| 2 mm thick | 0.13 | 1.96 | 0.009 | 12 | 7 | 69 | 1746 | 253 | 0.0011 | 17 |
| (BASOTECT ® 3012) | 0.13 | 1.93 | 0.009 | 11 | 6 | 59 | 1577 | 229 | 0.0009 | 17 |
| | 0.13 | 1.94 | 0.009 | 10 | 6 | 59 | 1544 | 224 | 0.0009 | 17 |
| | 0.14 | 2.09 | 0.009 | 13 | 7 | 69 | 1460 | 212 | 0.0011 | 18 |
| Mean | 0.13 | 1.97 | 0.009 | 12 | 7 | 65 | 1631 | 237 | 0.0010 | 17 |
| Standard Deviation | 0.00 | 0.06 | 0.000 | 1 | 1 | 5 | 152 | 22 | 0.0001 | 1 |
| MR. CLEAN ® + VIVA ® | 0.83 | 2.67 | 0.041 | 47 | 22 | 216 | 2185 | 317 | 0.0035 | 108 |
| VIVA ® side up | 0.83 | 2.61 | 0.042 | 48 | 22 | 216 | 2339 | 339 | 0.0035 | 108 |
| | 0.84 | 2.73 | 0.040 | 57 | 25 | 245 | 2322 | 337 | 0.0039 | 110 |
| | 0.84 | 2.77 | 0.040 | 57 | 25 | 245 | 2223 | 322 | 0.0039 | 110 |
| | 0.84 | 2.78 | 0.039 | 60 | 26 | 255 | 2287 | 332 | 0.0041 | 110 |
| Mean | 0.84 | 2.71 | 0.040 | 54 | 24 | 235 | 2271 | 329 | 0.0038 | 109 |
| Standard Deviation | 0.01 | 0.07 | 0.001 | 6 | 2 | 18 | 66 | 10 | 0.0003 | 1 |
| MR. CLEAN ® + VIVA ® | 0.83 | 2.67 | 0.041 | 33 | 13 | 128 | 1291 | 187 | 0.0020 | 108 |
| VIVA ® side down | 0.83 | 2.61 | 0.042 | 33 | 13 | 128 | 1382 | 200 | 0.0020 | 108 |
| | 0.84 | 2.73 | 0.040 | 33 | 13 | 128 | 1208 | 175 | 0.0020 | 110 |
| | 0.84 | 2.77 | 0.040 | 35 | 14 | 137 | 1245 | 181 | 0.0022 | 110 |
| | 0.84 | 2.78 | 0.039 | 35 | 14 | 137 | 1232 | 179 | 0.0022 | 110 |
| Mean | 0.84 | 2.71 | 0.040 | 34 | 13 | 131 | 1271 | 184 | 0.0021 | 109 |
| Standard Deviation | 0.01 | 0.07 | 0.001 | 1 | 1 | 5 | 69 | 10 | 0.0001 | 1 |
| MR. CLEAN ® + Spnbd. | 0.35 | 2.04 | 0.022 | 53 | 30 | 294 | 6679 | 969 | 0.0047 | 46 |
| Spunbond side up | 0.36 | 2.00 | 0.023 | 55 | 33 | 324 | 7796 | 1131 | 0.0052 | 47 |
| | 0.34 | 1.93 | 0.023 | 43 | 28 | 275 | 7361 | 1068 | 0.0044 | 44 |
| | 0.34 | 2.02 | 0.022 | 50 | 29 | 284 | 6650 | 964 | 0.0046 | 44 |
| | 0.38 | 2.23 | 0.022 | 59 | 32 | 314 | 5454 | 791 | 0.0050 | 50 |
| Mean | 0.35 | 2.04 | 0.023 | 52 | 30 | 298 | 6788 | 985 | 0.0048 | 46 |
| Standard Deviation | 0.02 | 0.11 | 0.001 | 6 | 2 | 20 | 888 | 129 | 0.0003 | 2 |
| MR. CLEAN ® + Spnbd. | 0.36 | 2.00 | 0.023 | 29 | 15 | 147 | 3544 | 514 | 0.0024 | 47 |
| Spunbond side down | 0.34 | 1.93 | 0.023 | 32 | 15 | 147 | 3944 | 572 | 0.0024 | 44 |
| | 0.34 | 2.02 | 0.022 | 29 | 14 | 137 | 3210 | 466 | 0.0022 | 44 |
| | 0.38 | 2.23 | 0.022 | 30 | 14 | 137 | 2386 | 346 | 0.0022 | 50 |
| Mean | 0.36 | 2.05 | 0.023 | 42 | 19 | 142 | 3271 | 474 | 0.0023 | 46 |
| Standard Deviation | 0.02 | 0.13 | 0.001 | 1 | 1 | 6 | 662 | 96 | 0.0001 | 2 |
| VIVA ® | 0.50 | 0.75 | 0.087 | 2 | 1 | 10 | 4480 | 650 | 0.0002 | 65 |
| (wire side up, as on wipe) | 0.51 | 0.78 | 0.085 | 2 | 1 | 10 | 3983 | 578 | 0.0002 | 67 |
| | 0.49 | 0.76 | 0.084 | 2 | 1 | 10 | 4306 | 624 | 0.0002 | 64 |
| | 0.49 | 0.77 | 0.083 | 2 | 1 | 10 | 4140 | 600 | 0.0002 | 64 |
| | 0.48 | 0.77 | 0.081 | 2 | 1 | 10 | 4140 | 600 | 0.0002 | 63 |
| Mean | 0.49 | 0.77 | 0.084 | 2 | 1 | 10 | 4210 | 611 | 0.0002 | 64 |
| Standard Deviation | 0.01 | 0.01 | 0.002 | 0 | 0 | 0 | 189 | 27 | 0.0000 | 1 |
| Spunbond | 0.12 | 0.06 | 0.261 | 1 | NA | NA | NA | NA | NA | 16 |
| | 0.12 | 0.06 | 0.261 | 1 | NA | NA | NA | NA | NA | 16 |
| | 0.13 | 0.07 | 0.242 | 1 | NA | NA | NA | NA | NA | 17 |
| | 0.13 | 0.07 | 0.242 | 1 | NA | NA | NA | NA | NA | 17 |
| | 0.13 | 0.07 | 0.242 | 1 | NA | NA | NA | NA | NA | 17 |
| Mean | 0.13 | 0.07 | 0.250 | 1 | NA | NA | NA | NA | NA | 16 |
| Standard Deviation | 0.01 | 0.01 | 0.010 | 0 | NA | NA | NA | NA | NA | 1 |
| BASOTECT ® 2011 | 0.12 | 1.75 | 0.009 | 5 | 3 | 29 | 1058 | 153 | 0.0005 | 16 |
| 2 mm thick | 0.12 | 1.74 | 0.009 | 5 | 3 | 29 | 1076 | 156 | 0.0005 | 16 |
| | 0.12 | 1.84 | 0.009 | 7 | 4 | 39 | 1214 | 176 | 0.0006 | 16 |
| | 0.14 | 1.78 | 0.010 | 7 | 4 | 39 | 1341 | 194 | 0.0006 | 18 |
| | 0.15 | 1.84 | 0.011 | 8 | 4 | 39 | 1214 | 176 | 0.0006 | 20 |
| Mean | 0.13 | 1.79 | 0.009 | 6 | 4 | 35 | 1180 | 171 | 0.0006 | 17 |
| Standard Deviation | 0.01 | 0.05 | 0.001 | 1 | 1 | 5 | 116 | 17 | 0.0001 | 2 |

In Table 3, results are shown for the overall density of the article sample under a load of about 0.05 psi. The article sample density may range from about 0.01 to about 0.1 g/cc, such as from about 0.02 to about 0.08 g/cc. The basis weight of the combined article sample (foam material, adhesive material, and reinforcing layer) ranged from about 40 gsm to about 110 gsm in the article samples that were tested, though much broader ranges are within the scope of the present invention. For example, the basis weight could range from about 15 gsm to about 400 gsm, or from about 25 gsm to about 300 gsm, or from about 25 gsm to about 250 gsm, or from about 25 gsm to 200 gsm, or from about 30 gsm to about 150 gsm. Higher basis weights may be achieved by using a heavier reinforcing layer, such as two layers of VIVA® towel web joined together, or a heavier foam layer, or using additional components such as adhesive material or other additives. Basis weight is typically measured in a dry state under TAPPI conditions (23° C. and 50% relative humidity).

The bending stiffness values of the article samples, measured according to the Zwick Flexibility test, range from about 0.002 Nm to about 0.005 Nm for the reinforced foam layers having a reinforcing layer joined to a 2-mm thick layer of foam material. Given the expected relationship between bending stiffness and thickness, it is believed that substantially thicker article samples still within the scope of the present invention may have significantly higher bending stiffness values, such as up to about 0.4 Nm or about 0.05 Nm and still be effective for many cleaning purposes. Further, increased bending stiffness could be achieved by using a heavier basis weight of adhesive material or a stiffer reinforcing layer.

The article samples were also tested for tensile properties, again after being conditioned at 23° C. and 50% relative humidity for at least four hours. Mean tensile results are shown in Table 4, which also includes mean stiffness results from the Zwick Flexibility tests previously described. Tensile testing was conducted on an MTS Alliance RT/1 tensile tester, available from the MTS Corp., located in Eden Prairie, Minn., running with TestWorks® 4 Universal Testing Software for Electromechanical Systems, also available from MTS Corporation. For tensile testing, a 1-inch wide sample was mounted between 1.5-inch wide jaws with a 2-inch jaw span (gage length). The crosshead speed was 10 inches per minute. The strips were cut in the machine direction. In wet tensile testing, the article sample was gently bent to form a loop in the center that was dipped in deionized water, such that a central region about 1-inch long was immersed. Excess water was removed by gentle blotting, and then the article sample was mounted between the jaws with the wetted region of the article sample roughly centered between the jaws, followed by tensile testing.

less. In some embodiments of the present invention, it is believed that the combination of high wet tensile strength (about 800 grams or greater, for a 1-inch wide strip) coupled with a low bending stiffness such as about 0.05 Nm or less, or 0.01 Nm or less, may result in a reinforced foam layer with good durability in use and with excellent flexibility for repeated attachment and release or for good comfort when worn on the body under a variety of body positions.

EXAMPLE 10

Hand-Made Reinforced Foam Layers

Pads similar to those of Example 9 were made, but using a aerosol spray adhesive material instead of a meltblown adhesive material. The spray adhesive material was 3M™ Hi-Strength Spray 90, commercially available from 3M Corp., located in Minneapolis, Minn. The pad samples were prepared by applying spray onto a surface of the foam material and the pressing it against the reinforcing layer, a tissue web or spunbond web, that had also been sprayed with the adhesive material and cutting the resulting laminate to size. The pad samples were made using BASOTECT® 2011 foam material (treated by the manufacturer to be hydrophilic) with thicknesses of 2 mm, 3 mm, 5 mm, and 8 mm. The pad samples were also made using slices cut from the foam material of the MR. CLEAN® product with a variety of thicknesses (1 mm, 2 mm, and 3 mm). Foam layers from both sources were then adhesively attached to a variety of substrates such as creped tissue, and spunbond webs serving as reinforcing layers for the foam layers. A partial listing of specific examples made is set forth below, along with other hand-made examples using other attachment means.

TABLE 4

Summary of physical properties of various foam layers according to the present invention.

| Sample ID | Basis Wt. gsm | Bending Stiffness Nm | Caliper 0.05 psi mm | Density g/cc | Tensile Wet/Dry % | Tensile Dry gm/1" | Tensile Wet gm/1" | % Stretch Dry | % Stretch Wet |
|---|---|---|---|---|---|---|---|---|---|
| MR. CLEAN ® Slices, 2 mm (BASOTECT ®.3012) | 17 | 0.0010 | 1.97 | 0.0086 | 90 | 525 | 475 | 21.0 | 22.0 |
| MR. CLEAN ® + VIVA ® | | | | | 60 | 1683 | 1003 | 29.6 | 29.3 |
| VIVA ® side up | 109 | 0.0038 | 2.71 | 0.0402 | | | | | |
| VIVA ® side down | 109 | 0.0021 | 2.71 | 0.0402 | | | | | |
| MR. CLEAN ® + Spunbond | | | | | 85 | 3015 | 2566 | 31.2 | 28.2 |
| Spunbond side up | 46 | 0.0048 | 2.04 | 0.0225 | | | | | |
| Spunbond side down | 46 | 0.0023 | 2.05 | 0.0224 | | | | | |
| VIVA ® | 64 | 0.0002 | 0.77 | 0.0831 | 53 | 360 | 192 | 18.6 | 17.7 |
| Spunbond | 16 | — | 0.07 | 0.2286 | 103 | 1883 | 1941 | 27.2 | 35.5 |
| BASOTECT ® 2011, 2 mm | 17 | 0.0006 | 1.79 | 0.0095 | 117 | 168 | 197 | 10.7 | 13.4 |

The results in Table 4 indicate that in the reinforced foam layers of the present invention, only a small portion of overall tensile strength came from the foam layer. The combination of the adhesive material plus the reinforcing layer may significantly strengthen the reinforced foam layer relative to a foam layer alone, especially for thin foam layers. The overall dry or wet tensile strength of a foam layer (reinforced or not) tested in a 1-inch strip with a 2-inch jaw span may be about 600 grams or greater, such as about 800 grams or greater, about 1000 g or greater, about 1500 grams or greater, about 2000 grams or greater, or about 2500 grams or greater. Wet and dry tensile strength may also be below about 10,000 grams (when tested for a 1-inch strip with a 2-inch jaw span), such as about 7,000 grams or less or about 5,000 grams or BASOTECT® 2011 foam layers were cut to dimensions of 95 mm×133 mm×2 mm and joined to an 0.5 osy spunbond web using a light application of 3M™ Hi-Strength Spray Adhesive 90. Other cleaning wipe articles were made with foam layers having dimensions of 50 mm×50 mm×3 mm and 102 mm×102 mm×3 mm. In these examples, the reinforcing layer had the same dimensions as the foam layer and was coextensive therewith.

A layer of BASOTECT® foam material available from BASF, pre-treated to be hydrophilic, was also used. It was cut to dimensions of 95 mm×133 mm×5 mm and joined to the 0.5 osy spunbond web with 3M™ Hi-Strength Spray Adhesive 90.

A layer of BASOTECT® foam material having dimensions of 432 mm×254 mm×3 mm was joined to a VIVA® paper towel of the same dimensions using KOSA® (Charlotte, N.C.) bicomponent binder fibers with a nominal length of 6 mm. An airlaid handsheet former was used to apply the binder fibers uniformly to the paper towel. The foam material was placed thereon, and the collection was heated at 172° C. for 30 minutes under a load of 0.02 psi to activate the binder fibers thereby forming a bonded composite of the KOSA® bicomponent binder fiber, VIVA® paper towel web, and foam material. After cooling, the bonded composite was cut to form six wipes having planar dimensions of 133 mm×95 mm.

A layer of BASOTECT® 2011 foam material with dimensions of 124 mm×133 mm×2 mm was joined to a VIVA® paper towel of the same dimensions using a Pellon® Wonder-Under Transfer Web #805, available from Pellon Consumer Products Division, Freudenberg Nonwovens, located in Durham, N.C., to form a composite of the foam material and the VIVA® paper towel web. The adhesive transfer web was activated by ironing the composite with a handheld 1200 Watt Sunbeam iron (Model 3953-006) on the wool setting.

In one embodiment of the present invention, a 3-mm thick layer of BASOTECT® 2011 foam material was cut to yield a foam layer with dimensions of 102 mm×102 mm×3 mm. The foam layer was joined with a conventional hotmelt adhesive material and hotmelt adhesive applicator on a pilot line to an 0.5 ounce-per-square-yard (osy) polypropylene spunbond web.

EXAMPLE 11

Curved Shear Attachment Strength

Figure 29:
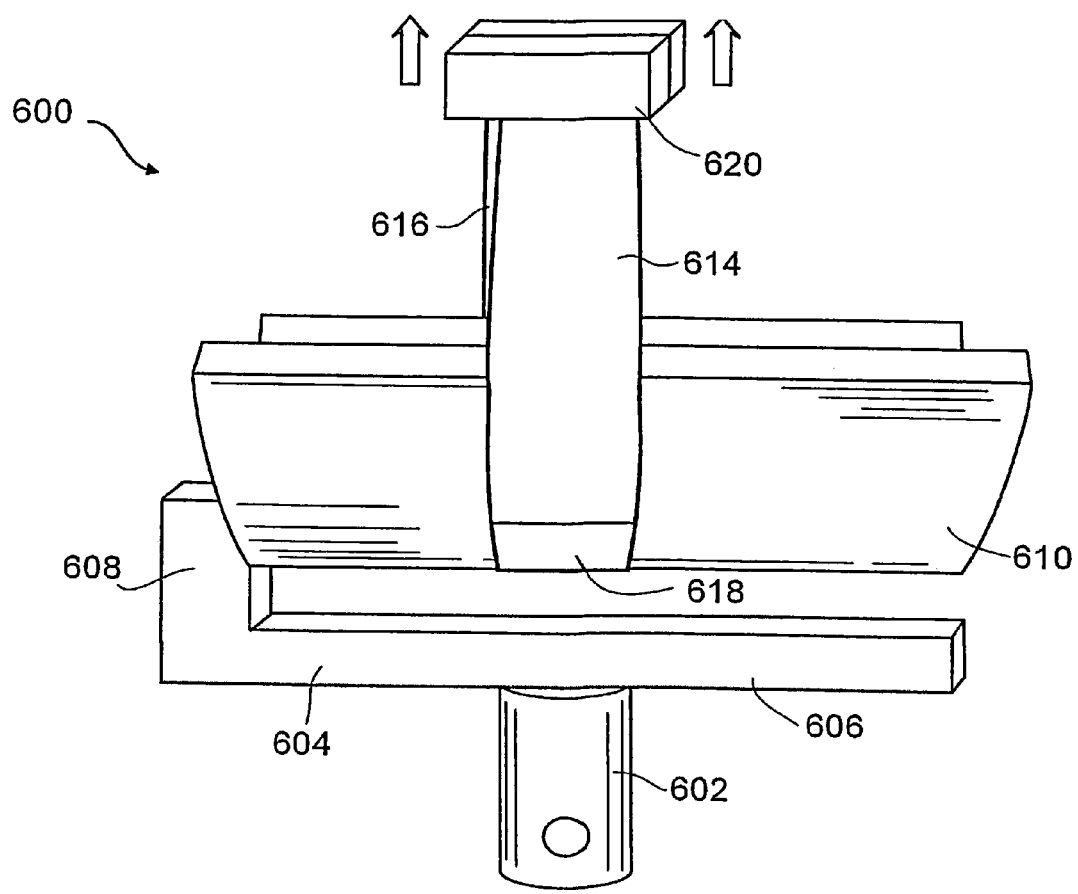
FIG. 29 depicts apparatus used for the Curved Shear Attachment Strength test.
Figure 3:
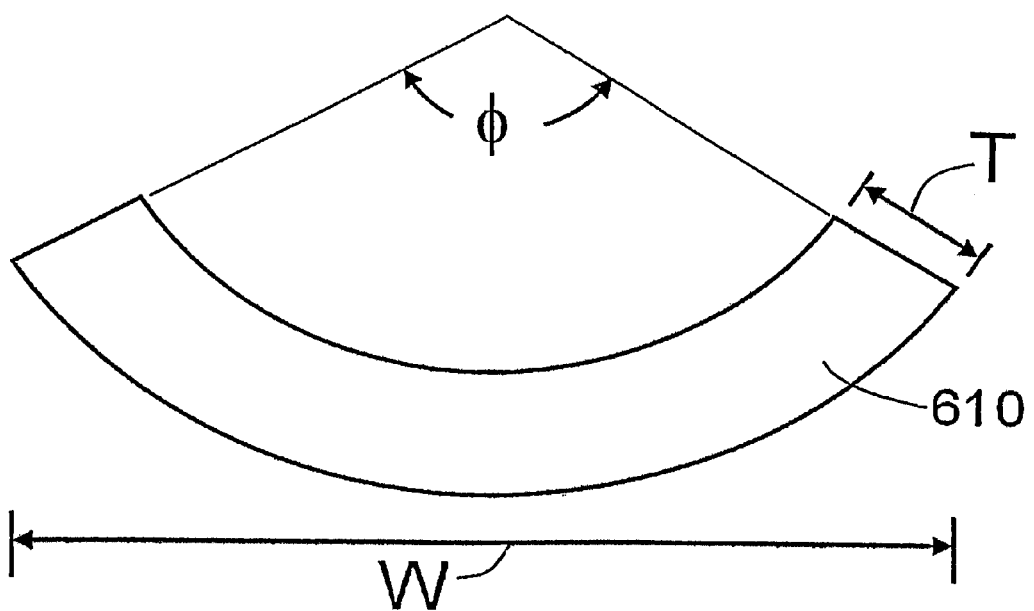

A measure of the strength of attachment of foam layers to landing layers of the present invention was obtained using a universal testing machine, an MTS Alliance RT/1 testing machine (commercially available from the MTS Systems Corp., located at Eden Prairie, Minn.) running with TestWorks® 4 software, version 4.04c, with a 100 N load cell. For the test procedure, an upper clamp was used with rubber-lined jaws that are pneumatically loaded for good grasping of test samples. Into the lower mount of the test device was placed a special rig as shown in FIG. 29 which provided a curved surface against which an overlapping region of a foam layer and landing layer could be subject to tensile force. In FIG. 29, the test rig 600 comprises a cylindrical base 602 adapted for mounting into the lower mount of the universal testing machine (not shown), joined to a an attachment section 604 comprising a horizontal beam 606 and a vertical beam 608 which is bolted into a curved section 610.

Further details about the geometry of the curved section 610 are shown in the cross-sectional view of FIG. 30, which shows that the curved section 610 represents a circular arc subtending an angle φ of 110 degrees, has a thickness T of 0.5 inches, and a width W of 4.5 inches. The length of the curved section 610, the distance it extends into the plane of the paper in FIG. 30 (the left-to-right distance spanned by the curved section 610 in FIG. 29) is 8 inches. The curved section 610 made of rigid nylitron and has a smooth surface finish (a shape turned finish) of 32 microinches in roughness (a "32 finish") as measured with a Microfinish Comparator (Gar Electroforming, Danbury, Conn.).

Figure 31:
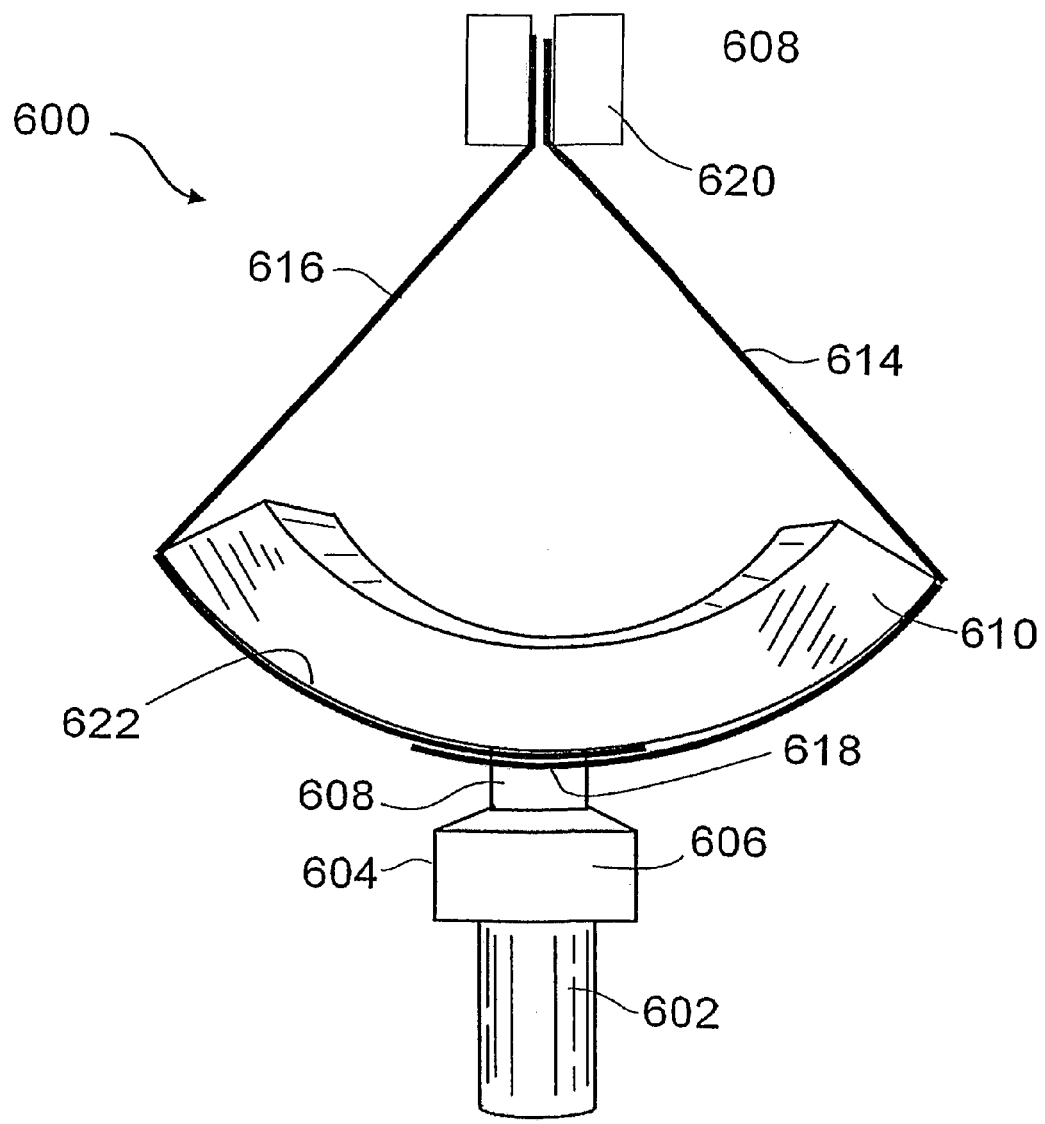
FIG. 31 shows another view of the apparatus used for the Curved Shear Attachment Strength test.

As shown in FIG. 29 and also in a side view in FIG. 31, the curved section 610 is used to hold a length of a two-inch wide foam layer strip 614 and a length of a three-inch wide landing layer strip 616 that overlap and are joined in an attachment zone 618 while the remote ends of the foam layer strip 614 and the landing layer strip 616 are also held in an upper clamp 620 connected to the movable head (not shown) of the universal testing machine (not shown). The foam layer and landing layer strips 614 and 616, respectively, are 1-inch wide unless otherwise specified. The joining of the foam layer and landing layer strips 614 and 616, respectively, in the attachment zone 618 is carried out by superposing the laterally centered, aligned foam layer and landing layer strips 614 and 616, respectively, to from an overlap region 612 and then applying a load to ensure good contact. Unless otherwise specified, the load was provided by a brass laboratory roller having a mass of 7.0 kilograms, which was slowly rolled over the attachment zone 618 twice (forward and then back). After attaching the foam layer and landing layer strips 614 and 616, respectively, the attachment zone 618 is then centered on the lower portion of the curved section 610 and the ends of the foam layer and landing layer strips 614 and 616, respectively, remote from the attachment zone 618 are then placed in the jaw of the upper clamp 620. The lower surface of the upper clamp 620 is 3 inches above the upper surface of the curved section 610 before the test procedure begins. There is negligible tension yet no significant slack in the foam layer and landing layer strips 614 and 616, respectively, before the test procedure begins.

A measure of the strength of the attachment in the overlap region 612 may be obtained by running the universal test machine as if a tensile test were being carried out and measuring the peak load at failure. The test procedure is executed by moving the upper mount upwards at a crosshead speed of 10 inches per minute until there is failure, which may be failure of the attachment zone 618 or, in some cases, breaking of one of the foam layer and landing layer strips 614 and 616, respectively, elsewhere. The peak load before failure is the attachment strength.

The following materials were used in attachment strength testing:
BASOTECT® 2011 melamine foam material commercially available from BASF (located at Ludwigshafen, Germany). Thickness: 2 mm+/−0.15 mm.
BASOTECT® 3012, Melamine foam material commercially available from BASF. Thickness: 2 mm+/−0.15 mm.
FOAMEX® Z60B polyurethane foam made by G. D. Foamex (located at Eddystone, Pa.). Thickness about ⅛", nominal pore size: 60.
GRAB-IT™ Dry Cloths with "Improved; Deeper Pockets" commercially from S.C. Johnson & Sons, (located at Racine, Wis.) under the UPC: 046500663284 and purchased at Wal-Mart in Appleton, Wis., in June 2004.
SWIFFER® Disposable Cloths "Texture 3D" commercially available from Proctor & Gamble (located at Cincinnati, Ohio) under the UPC: 037000318212 and purchased at Wal-Mart in Appleton, Wis., in June 2004.
TURTLE WAX® Professional Cleaning Cloth MC1 commercially from Turtle Wax Inc. (located at Chicago, Ill.) under the UPC: 076063056995.
Lemon Frost Rainbow Felt (a square of felt material) commercially available from Kunin Felt/a Foss Mfg. Co. Inc. (located at Hampton, N.H.) under the UPC: 028981921985 and purchased at Wal-Mart in Appleton, Wis., in June 2004.
Fall Microsuede, Olive, 100% polyester woven microfiber textile made in South Korea under the trade designation of 664-9099 and purchased at JoAnn Fabrics in Appleton, Wis., in June 2004.
CLC-424, spunlace nonwoven web, manufactured by Polymer Group Inc. (PGI, located in North Charleston, S.C.). Basis weight 2.0 ounces per square yard, "No Image," 30% PET/35% Tencel/35% Rayon.

An elastomeric meltblown web having a basis weight of about 0.45 ounces per square yard (osy) comprising 50% by volume of TICONA CELANEX® PBT 2008 polybutylene terephthalate (PBT) manufactured by Ticona (Celanese AG) (located in Kelsterbach, Germany) and 50% by volume of Kraton® G2755 elastomer formed on a meltblowing pilot line at a speed of about 127 feet per minute. The bicomponent material was made substantially according to commonly owned co-pending U.S. patent application Ser. No. 10/743860, filed by Lassig et al. on Dec. 22, 2003, the disclosure of which is herein incorporated by reference to the extent that it is non-contradictory herewith.

In a first series of tests, with the two-inch wide foam layer strip 614 centered on the three-inch wide landing layer strip 616, formation of a two-inch long attachment zone 618 was accomplished without the use of the metal roller by simply lightly pressing the foam layer and landing layer strips 614 and 616, respectively, together by hand, with an estimated load of about 300 grams of force. The foam layer strip 614 was the 2-mm thick BASOTECT® 2011 foam material and the landing layer strip 616 was the elastomeric meltblown web comprising 50%/50% (by volume) TICONA CELANEX® PBT 2008 polybutylene terephthalate (PBT) manufactured by Ticona (Celanese AG) (located in Kelsterbach, Germany) and 50% Kraton® G2755 elastomer (commercially available from Kraton Polymers located at Houston, Tex.). The area of contact in the attachment zone 618 was 4 square inches. The foam layer strip 614 was next to the curved section 610 in the attachment zone 618, a configuration termed "foam in", when the foam layer and landing layer strips 614 and 616, respectively, were placed in the test rig 600. During execution of the test procedure, the foam layer strip 614 broke in each of three repeat runs at an average peak load of 1466 grams of force, corresponding to 366 gf/in$^2$ or 56.7 gf/cm$^2$ over the area of the attachment zone 618. The test procedure was then repeated using the FOAMEX® Z60B polyurethane foam material as the landing layer strip 616. The landing layer strip 616 (the elastomeric meltblown web) broke at a peak load of 2156 grams of force (gf), corresponding to 539 gf/in$^2$ or 83.5 gf/cm$^2$ over the area of the attachment zone 618.

The first test with the BASOTECT® 2011 foam material and the elastomeric meltblown web was then repeated, but with a two-inch wide adhesive packing tape added as a reinforcing layer to one side (the non-contact side) of both the foam layer strip 614 and the landing layer strip 616 to prevent premature failure of the foam layer and landing layer strips 614 and 616, respectively, in order to better estimate the actual attachment strength in the attachment zone 618. But with the reinforcing tape in pace, the attachment zone 618 did not fail before the load cell reached its maximum range (force greater than 100 Newtons).

It was hypothesized that edge effects on the upper corners of the curved section 610 might lead to inflated strength measurements because of friction in that region. To mitigate edge effects, a lightweight smooth steel cylinder 4.75 inches in diameter was placed over the curved section 610 of the test rig 600, and the first test with the BASOTECT® 2011 foam material and the elastomeric meltblown web was repeated (no reinforcing tape was used). Over the course of three more repeat runs, the foam layer strip 614 broke in each test at an average peak load of 1796 gf, corresponding to 449 gf/in$^2$ or 69.6 gf/cm$^2$ over the area of the attachment zone 618. Based on these runs, it did not appear that edge effects played a dominant role in the high peak loads being obtained. The metal cylinder over the curved section 610 was then removed in all subsequent test runs.

The length of the attachment zone 618 was then decreased to 1 inch instead of 2 inches for this and all subsequent "curved shear" tests on the curved section 610. The first test was then repeated with the reduced attachment zone 618 in the "foam in" configuration (the foam layer strip 614 was adjacent to the curved section 610 in the attachment zone 618). The test gave foam layer strip 614 breakage at a peak load of 1795 gf, corresponding to 898 gf/in$^2$ or 139 gf/cm$^2$ over the area of the attachment zone 618. The test procedure was repeated again in the "foam out" configuration (the landing layer strip 616 was adjacent to the curved section 610 in the attachment zone 618), giving a peak load at detachment (not breakage of the landing layer strip 616) of 921 gf, corresponding to 461 gf/in$^2$ or 71.4 gf/cm$^2$ over the area of the attachment zone 618.

Thus, the Curved Shear Attachment value for a foam layer fastening system of the present invention may be about 5 gf/cm$^2$ or greater, such at least any of the following values: abpit 10 gf/cm$^2$, about 20 gf/cm$^2$, about 40 gf/cm$^2$, about 60 gf/cm$^2$, about 80 gf/cm$^2$, about 100 gf/cm$^2$, and about 140 gf/cm$^2$, with exemplary ranges of from about 5 gf/cm$^2$ to about 170 gf/cm$^2$, or from about 10 gf/cm$^2$ to about 120 gf/cm$^2$. Alternatively, the Curved Shear Attachment value may be than about 95 gf/cm$^2$ or less.

Testing was then conducted using the same procedures (1-inch long attachment zone) for a variety of additional combinations of materials. Results are shown in Table 5. Combinations of interest include the first run that used melamine foam material as both the foam layer strip 614 and the landing layer strip 616 (or rather, two self-attaching strips). Among the highest attachment strength combinations was the melamine foam material with the TURTLEWAX® cloth, a microfiber cleaning fabric. For some materials, such as the yellow "Lemon Felt" cloth, better attachment occurred with the coarser polyurethane foam material than with the melamine foam material.

TABLE 5

Curved Shear Attachment Strength Values.

| Foam Type | Landing Material | Con-fig. | Peak Load, gf Avg. | Peak Load, gf St.Dev. | Load/area gf/cm$^2$ | N |
|---|---|---|---|---|---|---|
| B. 2011 | B. 2011 | | 256.4 | 76.2 | 19.9 | 3 |
| Foamex ® | Foamex ® | | 719.7 | 100.9 | 55.8 | 3 |
| B. 2011 | TurtleWax ® Cloth | foam in | 1483.6 | 254.6 | 115.0 | 2 |
| B. 2011 | TurtleWax ® Cloth | foam out | Foam Broke | | 183.2 | 2 |
| Foamex ® | TurtleWax ® Cloth | foam in | 1538.3 | 26.3 | 119.2 | 2 |
| Foamex ® | TurtleWax ® Cloth | foam out | 2056 | 49.1 | 159.3 | 2 |
| B. 2011 | Fall Microsuede | foam in | Foam Broke | | 138.8 | 1 |
| B. 2011 | Fall Microsuede | foam out | 1304.2 | 118.1 | 101.1 | 3 |
| Foamex ® | Fall Microsuede | foam in | 546.5 | 127.8 | 42.3 | 3 |
| Foamex ® | Fall Microsuede | foam out | 211.1 | 74.7 | 16.4 | 2 |
| B. 2011 | Grab-It ® | foam in | 223.8 | 71.1 | 17.3 | 3 |
| B. 2011 | Grab-It ® | foam out | 411.4 | 108.7 | 31.9 | 3 |

TABLE 5-continued

Curved Shear Attachment Strength Values.

| Foam Type | Landing Material | Con-fig. | Peak Load, gf Avg. | St.Dev. | Load/area gf/cm² | N |
|---|---|---|---|---|---|---|
| Foamex® | Grab-It® | foam in | 402 | 70.2 | 31.2 | 3 |
| Foamex® | Grab-It® | foam out | 378.8 | 47.2 | 29.4 | 3 |
| B. 2011 | Swiffer® | foam in | 462.4 | 48.2 | 35.8 | 3 |
| B. 2011 | Swiffer® | foam out | 425.2 | | 33.0 | 1 |
| B. 3012 | Swiffer® | foam in | 435.2 | 16.4 | 33.7 | 3 |
| B. 3012 | Swiffer® | foam out | | | 0.0 | |
| Foamex® | Swiffer® | foam in | 422.1 | 55 | 32.7 | 3 |
| Foamex® | Swiffer® | foam out | 382.4 | | 29.6 | 1 |
| B. 2011 | Lemon Felt | foam in | 91.3 | — | — | 1 |
| B. 2011 | Lemon Felt | foam out | | | 0.0 | |
| Foamex® | Lemon Felt | foam in | 627.5 | 108.4 | 48.6 | 2 |
| Foamex® | Lemon Felt | foam out | 763.2 | 253.2 | 59.1 | 2 |
| B. 2011 | PBT/Kraton MB | foam in | Foam Broke | | 126.5 | 1 |
| B. 2011 | PBT/Kraton MB | foam out | 861.2 | 90 | 66.7 | 3 |
| B. 3012 | PBT/Kraton MB | foam in | Foam Broke | | 120.1 | 1 |
| B. 3012 | PBT/Kraton MB | foam out | 817.8 | 253.8 | 63.4 | 4 |
| Foamex® | PBT/Kraton MB | foam in | 1430 | 111.7 | 110.8 | 1 |
| Foamex® | PBT/Kraton MB | foam out | 381.2 | — | 29.5 | 1 |
| B. 2011 | CLC-424 (PGI) | foam in | 530.6 | 163.4 | 41.1 | 3 |
| B. 2011 | CLC-424 (PGI) | foam out | 344 | — | 26.7 | 1 |
| Foamex® | CLC-424 (PGI) | foam in | 830.1 | 27.5 | 64.3 | 3 |
| Foamex® | CLC-424 (PGI) | foam out | 494.6 | — | 38.3 | 1 |

EXAMPLE 12

Straight Shear Attachment Strength

Tensile tests were conducted in the universal test machine without the apparatus shown in FIGS. 29-31, but in a suspended form having no support surfaces adjacent to the foam layer and landing layer strips 614 and 616, respectively, the foam layer and landing layer strips 614 and 616, respectively, being arranged in a straight line with clamps holding the top of one strip 614 or 616 and the bottom of the other strip 616 or 614. The overlap region 612 of the foam layer and landing layer strips 614 and 616, respectively, the attachment zone 618, was two inches long (attachment area in the attachment zone 618 was 4 square inches). As in the curved shear tests of Example 11, the foam layer strip 614 was two inches wide and the landing layer strip 616 was three inches wide.

It was found that the application of tensile stress to two attached foam layer and landing layer strips 614 and 616, respectively, that are freely suspended allows instabilities such as buckling to arise at relatively low loads. The buckling may cause premature separate of the foam layer and landing layer strips 614 and 616, respectively, in the attachment zone 618. In contrast, a strip 614 or 616 that is against a solid surface, such as would occur in a fastener on a diaper or other absorbent article, is much more stable and not as prone to instabilities that cause early release under tension. Nevertheless, testing was conducted in straight shear mode using the combination of the BASOTECT® 2011 foam material with the elastomeric meltblown web of Example 11, giving an average peak load at failure (detachment) of 114 gf for 10 samples (standard deviation was 59.1 gf), corresponding to 28.6 gf/in² or 4.43 gf/cm² over the area of the attachment zone 618. The testing was repeated for the combination of FOAMEX® Z60B polyurethane foam material and the elastomeric meltblown web of Example 11, with 10 trials giving an average peak load at failure (detachment) of 245 gf for 10 samples (standard deviation was 101 gf), corresponding to 61.3 gf/in² or 9.5 gf/cm² over the area of the attachment zone 618. Thus, the mean Unsupported Straight Shear Attachment value for a foam layer fastening system of the present invention may be about 3 gf/cm² or greater, such at least any of the following values: about 4 gf/cm², about 5 gf/cm², about 9 gf/cm², about 13 gf/cm², about 20 gf/cm², and about 40 gf/cm², with ranges of from about 3 gf/cm² to about 40 gf/cm², from about 3 gf/cm² to about 30 gf/cm², or from about 4 gf/cm² to about 20 gf/cm². Alternatively, the Unsupported Straight Shear Attachment value may be about 50 gf/cm² or less, or about 15 gf/cm² or less.

Further straight shear tests were conducted for several other materials, giving the results shown in Table 6.

TABLE 6

Straight Shear Attachment Strength values for several combinations of materials.

| Foam Type | Landing Material | Peak Load, gf Avg. | St.Dev. | Load/area gms/cm² | N |
|---|---|---|---|---|---|
| Foamex® | Foamex® | 214.28 | 15.20 | 8.3 | 3 |
| B. 2011 | TurtleWax® Cloth | 422.41 | 16.38 | 16.4 | 3 |
| Foamex® | TurtleWax® Cloth | 499.99 | 29.31 | 19.4 | 3 |
| B. 2011 | Grab-It® | 100.50 | 34.78 | 3.9 | 10 |
| Foamex® | Grab-It® | 120.68 | 12.82 | 4.7 | 5 |
| B. 2011 | Swiffer® | 86.93 | 14.43 | 3.4 | 5 |
| Foamex® | Swiffer® | 176.40 | 37.20 | 6.8 | 5 |
| B. 2011 | PBT/Kraton MB | 114.23 | 59.10 | 4.4 | 10 |
| Foamex® | PBT/Kraton MB | 245.24 | 101.30 | 9.5 | 10 |

EXAMPLE 13

Peel Strength

Figure 32:
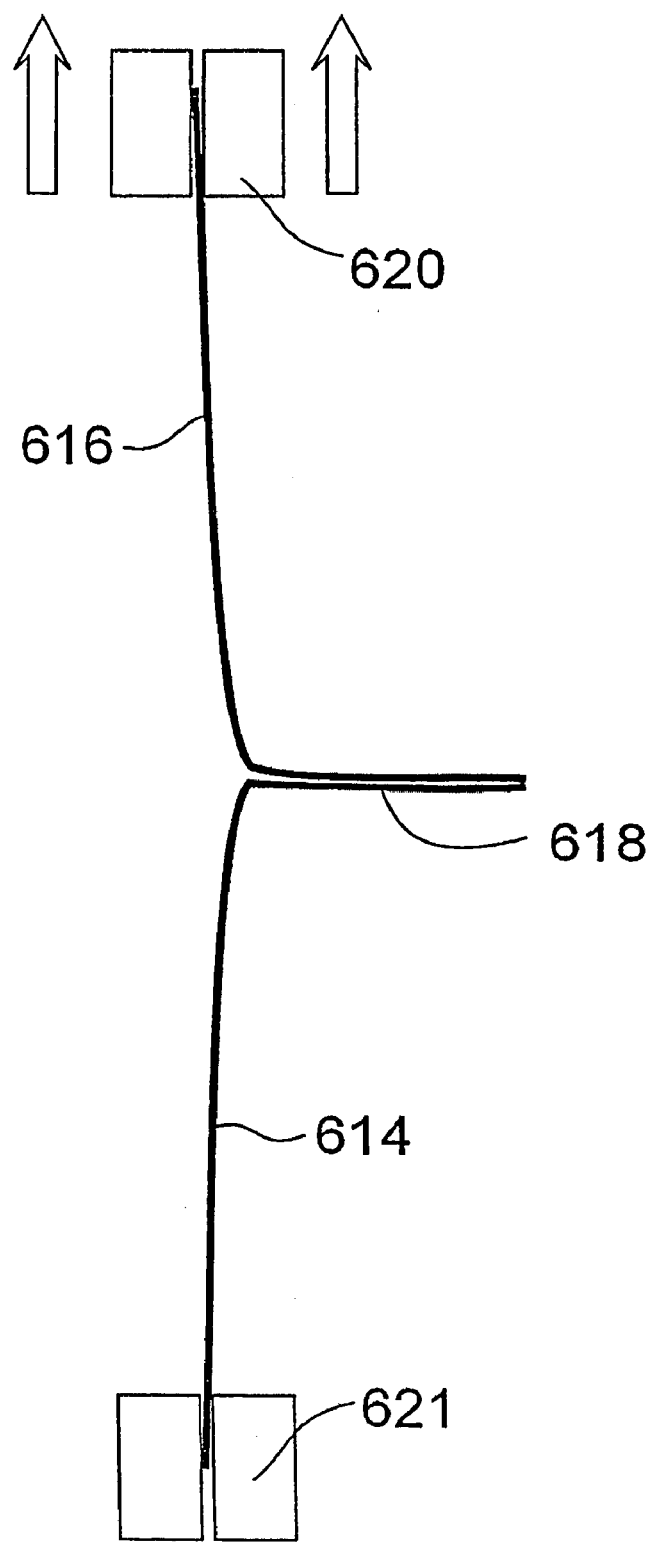
FIG. 32 depicts a configuration of test strips used in measuring peel strength.

Peel tests were conducted with the universal test machine (not shown) using the 180° peel configuration shown in FIG. 32, where the foam layer and landing layer strips 614 and 616, respectively, of a foam material and landing layer material, respectively, are joined in an attachment zone 618 configured to be peeled apart as the remote ends of the strips 614 and 616, respectively, are moved away from each other as they are held in the jaws of an upper clamp 620 and a lower clamp 621 as shown. Using the universal testing machine (not shown) as described in Examples 11 and 12, the force required to peel apart the attached foam layer and landing layer strips 614 and 616, respectively, may be measured. The crosshead speed for the peel testing was 20 inches per minute. The attachment zone 618 had a length (overlap distance) of two inches (4 square inches total overlap area 612). The gauge length (distance between the upper and lower clamps 620 and 621, respectively) for the test set up was 1.5 inches.

The Testworks software used could not generate statistical results for peel values less than 10 grams of force. All sample combinations that were measured in the curved shear tests of Example 11 did not give high enough peel resistance values for the software to process. However, charts of load versus extension for the peel results could be viewed. The highest peel resistance values were with the TURTLEWAX® cloth in combination with the FOAMEX® polyurethane foam material. Over an extension distance of 4 inches, the mean resistance was about 5 gf (corresponding to 2.5 gf/in or about 1 gf/cm over the peel width of 2 inches). One local peak value was nearly 10 gf. The TURTLEWAX® cloth combined with the BASOTECT® 2011 melamine foam material gave peel resistance (averaged over the 4-inch extension distance required to fully separate the two foam layer and landing layer strips 614 and 616) of about 2.5 gf, with local peak values of about 4 gf. The FOAMEX® foam material with the SWIFFER® cloth have a mean peel resistance of about 1.8 gf, with a momentary local peak of about 2.9 gf. Similar results were seen with other combinations. The combination of FOAMEX® foam material with another strip of FOAMEX® foam material gave a peel resistance slightly above 1.

In general, the peak peel resistance over a 4-inch elongation span was about 10 gf or less and typically about 5 gf or less, and the mean peel resistance one version of the 4-inch elongation span (as well as over the first one or two inches of elongation) was typically about 5 gf or less or about 3 gf or less.

The Attachment Force/Peel Force Ratio refers to the ratio of peak force for the Curved Shear Attachment Test (2-inch wide, 1-inch long attachment zone 618, using the foam in or foam out configuration that gives the highest peak force) to the average 180° peel resistance (2-inch wide, 2-inch long attachment zone 618) force. For example, for the combination of the TURTLEWAX® cloth with the FOAMEX® foam material, the ratio would be 159.3/5 for a ratio of about 32, reflecting the high shear strength of the attachment and the low peel forces required for removal. In general, the Attachment Force/Peel Force Ratio for the foam layer fastening systems according to the present invention may have any of the following values: about 5 or greater, about 10 or greater, about 15 or greater, about 20 or greater, about 25 or greater, about 30 or greater, from about 3 to about 100, from about 5 to about 50, from about 10 to about 150, from about 10 to about 35, or from about 15 to about 50.

It should be understood that the present invention includes various modifications that can be made to the embodiments of the absorbent article 90 or the cleaning wipe article 500 as described herein as come within the scope of the appended claims and their equivalents.

We claim:

1. An article having a mechanical fastener and configured to be worn by a user, comprising:
   a body portion configured to be worn by a user and including a landing layer wherein the landing layer comprises a plurality of fibers; and,
   the body portion also including a foam layer, the foam layer having a first surface comprising a plurality of free-standing struts adapted for engaging at least a portion of the plurality of fibers of the landing layer.

2. The article as set forth in claim 1, wherein the plurality of free-standing struts of the foam layer have diameters of about 50 microns or less.

3. The article as set forth in claim 1, wherein the plurality of free-standing struts of the foam layer have heights of about 500 microns or less.

4. The article as set forth in claim 1, wherein the plurality of fibers of the landing layer are selected from the group consisting of natural fibers, synthetic fibers, and mixtures thereof.

5. The article as set forth in claim 1, wherein fibers of the landing layer form loops.

6. The article as set forth in claim 5, wherein at least a portion of the free-standing struts are engageable with at least a portion of the loops in the landing layer.

7. The article as set forth in claim 5, wherein loops in the landing layer have a titer of about 4.5 dtex or less.

8. The article as set forth in claim 1, wherein the fibers of the landing layer form openings.

9. The article as set forth in claim 8, wherein at least a portion of the free-standing struts are engageable with at least a portion of the openings in the landing layer.

10. The article as set forth in claim 8, wherein openings in the landing layer have a diameter of about 0.5 µm or greater.

11. The article as set forth in claim 1, wherein the foam layer comprises a foam material selected from the group consisting essentially of: melamines; polyadehydes; polyurethanes; polylsocyanurites; polyolefins; polyvinylchloride; epoxy foams; ureaformaldehyde; latex foam; silicone foam; fluoropolymer foams; polystyrene foams; and, mixtures thereof.

12. The article as set forth in claim 1, wherein the foam layer comprises an open-celled foam material.

13. The article as set forth in claim 12, wherein the open-celled foam material has a density of about 0.006 g/cc to about 0.1 g/cc.

14. The article as set forth in claim 8, wherein at least a portion of the foam layer comprises a plurality of hooks wherein the plurality of hooks are engageable with the openings of the landing layer.

15. The article as set forth in claim 5, wherein at least a portion of the foam layer comprises a plurality of hooks wherein the plurality of hooks are engageable with the loops of the landing layer.

16. The article asset forth in claim 1, wherein:
    the body portion includes a stretch member extending outwardly therefrom, wherein the stretch member is formed of a necked bonded laminate material; and,
    the stretch member includes a tab member extending outwardly therefrom, wherein the tab member is formed of a spunbond/meltblown/spunbond material, and the foam layer is attached to the spunbond/meltblown/spunbond material.

17. The article as set forth in claim 1, wherein the article is a diaper.

18. The article as set forth in claim 1, wherein the foam layer and landing layer are capable of being engaged with a Shear Resistance of about 100 grams of force or greater per square centimeter.

19. The article as set forth in claim 18, wherein the foam layer and landing layer are further capable of being engaged with a Peel Resistance of about 50 grams or less of force per square centimeter.

20. An article having a mechanical fastener and configured to be worn by a user, comprising:
    a body portion configured to be worn by a user;
    the body portion including a landing layer comprising a plurality of fibers, wherein at least a portion of the fibers form openings in the landing layer; and,
    the body portion also including a foam layer, wherein the foam layer has a first surface comprising a plurality of free-standing struts capable of engaging the plurality of openings of the landing layer.

21. The article as set forth in claim 20, wherein the plurality of free-standing struts of the foam layer have diameters of about 50 microns or less.

22. The article as set fort in claim 20, wherein the plurality of free-standing struts of the foam layer have heights of about 500 microns or less.

23. The article as set forth in claim 20, wherein the plurality of fibers of the landing layer are selected from the group consisting of natural fibers, synthetic fibers, and mixtures thereof.

24. The article as set forth in claim 20, wherein at least a portion of the free-standing struts are engageable with at least a portion of the openings in the landing layer.

25. The article as set forth in claim 20, wherein openings in the landing layer have a diameter of about 0.5 µm or greater.

26. The article as set forth in claim 20, wherein the foam layer comprises a foam material selected from the group consisting essentially of: melamines; polyadehydes; polyurethanes; polyisocyanurites; polyolefins; polyvinylchloride; epoxy foams; ureaformaldehyde; latex foam; silicone foam; fluoropolymer foams; polystyrene foams; and, mixtures thereof.

27. The article as set forth in claim 20, wherein the foam layer comprises an open-celled foam material.

28. The article as set forth in claim 27, wherein the open-celled foam material has a density of about 0.006 g/cc to about 0.1 g/cc.

29. The article as set forth in claim 20, wherein at least a portion of the foam layer comprises a plurality of hooks wherein the plurality of hooks are engageable with the openings of the landing layer.

30. The article as set forth in claim 20, wherein:
the body portion includes stretch member extending outwardly therefrom, the stretch member is formed of a necked bonded laminate material; and,
the stretch member includes a tab member extending outwardly therefrom, wherein the tab member is formed of a spunbond/meltblown/spunbond material, and the foam layer is attached to the spunbond/meltblown/spunbond material.

31. The article as set forth in claim 20, wherein article is a diaper.

* * * * *

UNITED STATES PATENT AND TRADEMARK OFFICE
CERTIFICATE OF CORRECTION

PATENT NO. : 7,608,070 B2  Page 1 of 1
APPLICATION NO. : 10/956613
DATED : October 27, 2009
INVENTOR(S) : Chen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1010 days.

Signed and Sealed this

Twelfth Day of October, 2010

David J. Kappos
*Director of the United States Patent and Trademark Office*